United States Patent
Witschel et al.

(10) Patent No.: US 7,030,063 B1
(45) Date of Patent: Apr. 18, 2006

(54) CYCLOHEXENONQUINOLINOYL-DERIVATIVES AS HERBICIDAL AGENTS

(75) Inventors: Matthias Witschel, Ludwigshafen (DE); Ulf Misslitz, Neustadt (DE); Ernst Baumann, Dudenhofen (DE); Wolfgang von Deyn, Neustadt (DE); Klaus Langemann, Worms (DE); Guido Mayer, Neustadt (DE); Ulf Neidlein, Mannheim (DE); Roland Götz, Neulussheim (DE); Norbert Götz, Worms (DE); Michael Rack, Heidelberg (DE); Stefan Engel, Nieder-Olm (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/763,704

(22) PCT Filed: Aug. 27, 1999

(86) PCT No.: PCT/EP99/06322

§ 371 (c)(1),
(2), (4) Date: Feb. 26, 2001

(87) PCT Pub. No.: WO00/14069

PCT Pub. Date: Mar. 16, 2000

(30) Foreign Application Priority Data

Sep. 8, 1998 (DE) ................................ 198 40 799

(51) Int. Cl.
*A01N 43/42* (2006.01)
*C07D 401/08* (2006.01)
(52) U.S. Cl. ............... 504/247; 546/152; 546/173
(58) Field of Classification Search .......... 546/146, 546/152, 173; 514/311, 314; 504/247
See application file for complete search history.

(56) References Cited

U.S. PATENT DOCUMENTS 5,426,091 A * 6/1995 Barton et al. ............ 504/279
6,479,436 B1 * 11/2002 Otten et al. ............. 504/247

FOREIGN PATENT DOCUMENTS

| CA | 2266526 | 3/1998 |
| EP | 0 283 261 | 9/1988 |
| WO | WO 98/12180 | 3/1998 |

OTHER PUBLICATIONS

Nicolaescu et. al., "Radical-Induced Oxidative Transformation of Quinoline", J. Phys. Chem. A, 2003, 107, 427-433.*
Bundgaard, et. al., Design of Prodrugs, 1985, pp. 3-6.*
CA Reference 110:95273, "Preparation and testing of (heterocyclecarbonyl)cyclohexanediones and -triones as herbicides", Barton et. al., US Patent 5041681.*

* cited by examiner

Primary Examiner—Celia Chang
(74) Attorney, Agent, or Firm—Novak Druce & Quigg

(57) ABSTRACT

Cyclohexenonequinolinoyl derivatives of the formula I

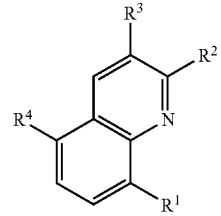

where:
$R^1$ is hydrogen, nitro, halogen, cyano, alkyl, haloalkyl, alkoxyiminomethyl, alkoxy, haloalkoxy, alkylthio, $C_1$–$C_6$-haloalkylthio, alkylsulfinyl, haloalkylsulfinyl, alkylsulfonyl, haloalkylsulfonyl, unsubstituted or substituted amino sulfonyl, unsubstituted or substituted sulfonyl amino, unsubstituted or substituted phenoxy, unsubstituted or substituted heterocyclyloxy, unsubstituted or substituted phenylthio or unsubstituted or substituted heterocyclylthio;
$R^2$, $R^3$ are hydrogen, alkyl, haloalkyl or halogen;
$R^4$ is substituted (3-oxo-1-cyclohexen-2-yl)carbonyl or substituted (1,3-dioxo-2-cyclohexyl)methylidene;
and their agriculturally useful salts;
processes for preparing the cyclohexenonequinolinoyl derivatives; compositions comprising them, and the use of these derivatives or compositions comprising them for controlling undesirable plants are described.

23 Claims, No Drawings

CYCLOHEXENONQUINOLINOYL-DERIVATIVES AS HERBICIDAL AGENTS

The present invention relates to novel cyclohexenonequinolinoyl derivatives of the formula I,

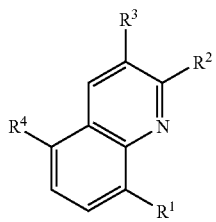

where:
$R^1$ is hydrogen, nitro, halogen, cyano, $C_1$–$C_6$-alkyl, $C_1$–$C_6$-haloalkyl, $C_1$–$C_6$-alkoxyiminomethyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N—($C_1$–$C_6$-alkyl)aminosulfonyl, N,N-di-($C_1$–$C_6$-alkyl)aminosulfonyl, N—($C_1$–$C_6$-alkylsulfonyl)amino, N—($C_1$–$C_6$-haloalkylsulfonyl)amino, N—($C_1$–$C_6$-alkyl)-N-($C_1$–$C_6$-alkylsulfonyl)amino, N—($C_1$–$C_6$-alkyl)-N-($C_1$–$C_6$-haloalkylsulfonyl) amino, phenoxy, heterocyclyloxy, phenylthio or heterocyclylthio, where the four last-mentioned radicals may be partially or fully halogenated and/or may carry one to three of the following substituents:
nitro, cyano, $C_1$–$C_4$-alkyl, $C_1$–$C_4$-haloalkyl, $C_1$–$C_4$-alkoxy or $C_1$–$C_4$-haloalkoxy;
$R^2$, $R^3$ are hydrogen, $C_1$–$C_6$-alkyl, $C_1$–$C_6$-haloalkyl or halogen;
$R^4$ is a compound IIa or IIb

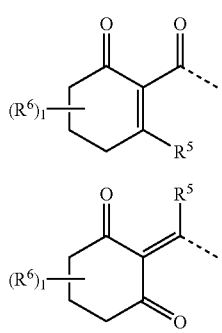

where
$R^5$ is halogen, $OR^7$, $SR^7$, $SOR^8$, $SO_2R^8$, $OSO_2R^8$, $POR^8R^9$, $OPR^8R^9$, $OPOR^8R^9$, $OPSR^8R^9$, $NR^{10}R^{11}$, $ONR^{11}R^{12}$, N-linked heterocyclyl or O—(N-linked heterocyclyl), where the heterocyclyl radical of the two last-mentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^6$ is nitro, halogen, cyano, $C_1$–$C_6$-alkyl, $C_1$–$C_6$-haloalkyl, di-($C_1$–$C_6$-alkoxy)methyl, di-($C_1$–$C_6$-alkylthio)methyl, ($C_1$–$C_6$-alkoxy)($C_1$–$C_6$-alkylthio)methyl, hydroxy, $C_1$–$C_6$-alkoxy, $C_1$–$C_6$-haloalkoxy, $C_1$–$C_6$-alkoxycarbonyloxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl;
or
two radicals $R^6$, which are linked to the same carbon, together form an —O—$(CH_2)_m$—, —O—$(CH_2)_m$—S—, —S—$(CH_2)_m$—S—, —O—$(CH_2)_n$— or —S—$(CH_2)_n$— chain which may be substituted by one to three radicals from the following group:
halogen, cyano, $C_1$–$C_4$-alkyl, $C_1$–$C_4$-haloalkyl or $C_1$–$C_4$-alkoxycarbonyl;
or
two radicals $R^6$, which are linked to the same carbon, together form a —$(CH_2)_p$ chain which may be interrupted by oxygen or sulfur and/or may be substituted by one to four radicals from the following group:
halogen, cyano, $C_1$–$C_4$-alkyl, $C_1$–$C_4$-haloalkyl or $C_1$–$C_4$-alkoxycarbonyl;
or
two radicals $R^6$, which are linked to the same carbon, together form a methylidene group which may be substituted by one or two radicals from the following group:
halogen, hydroxyl, formyl, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;
or
two radicals $R^6$, which are linked to the same carbon, together with this carbon form a carbonyl group;
or
two radicals $R^6$, which are linked to different carbons, together form a —$(CH_2)_n$ chain which may be substituted by one to three radicals from the following group:
halogen, $C_1$–$C_6$-alkyl, $C_1$–$C_6$-alkoxy, hydroxyl or $C_1$–$C_6$-alkoxycarbonyl;
$R^7$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, $C_1$–$C_{20}$-alkylcarbonyl, $C_2$–$C_6$-alkenylcarbonyl, $C_2$–$C_6$-alkynylcarbonyl, $C_3$–$C_6$-Cycloalkylcarbonyl, $C_1$–$C_6$-alkoxycarbonyl, $C_3$–$C_6$-alkenyloxycarbonyl, $C_3$–$C_6$-alkynyloxycarbonyl, ($C_1$–$C_{20}$-alkylthio)carbonyl, $C_1$–$C_6$-alkylaminocarbonyl, $C_3$–$C_6$-alkenylaminocarbonyl, $C_3$–$C_6$-alkynylaminocarbonyl, N, N-di-($C_1$–$C_6$-alkyl)aminocarbonyl, N—($C_3$–$C_6$-alkenyl)-N-($C_1$–$C_6$-alkyl)aminocarbonyl, N—($C_3$–$C_6$-alkynyl)-N-($C_1$–$C_6$-alkyl)aminocarbonyl, N—($C_1$–$C_6$-alkoxy)-N-($C_1$–$C_6$-alkyl)aminocarbonyl, N—($C_3$–$C_6$-alkenyl)—N—($C_1$–$C_6$-alkoxy) aminocarbonyl, N—($C_3$–$C_6$-alkynyl)-N-($C_1$–$C_6$-alkoxy)aminocarbonyl, di-($C_1$–$C_6$-alkyl)-aminothiocarbonyl, $C_1$–$C_6$-alkylcarbonyl-$C_1$–$C_6$-alkyl, $C_1$–$C_6$-alkoxyimino-$C_1$–$C_6$-alkyl, N—($C_1$–$C_6$-alkylamino)imino-$C_1$–$C_6$-alkyl or N,N-di-($C_1$–$C_6$-alkylamino)imino-$C_1$–$C_6$-alkyl, where the abovementioned alkyl, cycloalkyl and alkoxy radicals may be partially or fully halogenated and/or may carry one to three of the following groups:
cyano, $C_1$–$C_4$-alkoxy, $C_1$–$C_4$-alkylthio, di-($C_1$–$C_4$alkyl) amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl) amino-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, heterocyclyloxycarbonyl, phenoxythiocarbonyl, heterocyclyloxythiocarbonyl, phenoxy-$C_1$–$C_6$-alkylcarbonyl, heterocyclyloxy-$C_1$–$C_6$-alkylcarbonyl, phenylaminocarbonyl, N—($C_1$–$C_6$-alkyl)-N-(phenyl) aminocarbonyl, heterocyclylaminocarbonyl, N—($C_1$–$C_6$-alkyl)-N-(heterocyclyl) aminocarbonyl, phenyl-$C_2$–$C_6$-alkenylcarbonyl or heterocyclyl-$C_2$–$C_6$-alkenylcarbonyl, where the phenyl and the heterocyclyl radical of the 20 last-mentioned substituents may be partially or fully halogenated and/or may carry one to three of the following radicals:

nitro, cyano, $C_1$–$C_4$ alkyl, $C_1$–$C_4$-haloalkyl, $C_1$–$C_4$-alkoxy or $C_1$–$C_4$-haloalkoxy;

$R^8$, $R^9$ are $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-Cycloalkyl, hydroxyl, $C_1$–$C_6$-alkoxy, amino, $C_1$–$C_6$-alkylamino, $C_1$–$C_6$-haloalkylamino, di-($C_1$–$C_6$alkyl)amino or di-($C_1$–$C_6$-haloalkyl)amino, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, di-($C_1$–$C_4$alkyl) amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{10}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di-($C_1$–$C_6$-alkyl) amino or $C_1$–$C_6$-alkylcarbonylamino, where the abovementioned alkyl, cycloalkyl and alkoxy radicals may be partially or fully halogenated and/or may carry one to three radicals from the following group:

cyano, $C_1$–$C_4$-alkoxy, $C_1$–$C_4$-alkylthio, di-($C_1$–$C_4$-alkyl) amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl; phenyl, heterocyclyl, phenyl-$C_1$–$C_6$-alkyl or heterocyclyl-$C_1$–$C_6$-alkyl, where the phenyl or heterocyclyl radical of the four last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{11}$, $R^{12}$ are $C_1$–$C_6$-alkyl, $C_3$–$C_6$-alkenyl, $C_3$–$C_6$-alkynyl or $C_1$–$C_6$-alkylcarbonyl;

l is 0 to 6;
m is 2 to 4;
n is 1 to 5;
p is 2 to 5;

and their agriculturally useful salts.

Moreover, the invention relates to processes for preparing compounds of the formula I, to compositions comprising them and to the use of these derivatives or the compositions comprising them for controlling harmful plants.

The literature, for example WO 98/12 180 and EP-A 283 261, discloses quinolinoyl or fused phenyl derivatives which are linked to an unsubstituted or substituted (1-hydroxy-3-oxo-cyclohex-1-en-2-yl)carbonyl radical. However, the herbicidal properties of the prior art compounds and their compatibility with crop plants are not entirely satisfactory.

It is an object of the present invention to provide other biologically, in particular herbicidally, active compounds.

We have found that this object is achieved by the cyclohexenonequinolinoyl derivatives of the formula I and their herbicidal action.

Furthermore, we have found herbicidal compositions which comprise the compounds I and have very good herbicidal action. Moreover, we have found processes for pr paring these compositions and methods for controlling undesirable vegetation using the compounds I.

Depending on the substitution pattern, the compounds of the formula I may contain one or more chiral centers, in which case they are present as enantiomers or mixtures of diastereomers. The invention provides both the pure enantiomers or diastereomers and their mixtures.

The compounds of the formula I may also be present in the form of their agriculturally useful salts, where the type of salt is usually immaterial. In general, the salts of those cations and the acid addition salts of those acids are suitable whose cations and anions, respectively, do not negatively affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, where, if desired, one to four hydrogen atoms may be replaced by $C_1$–$C_4$-alkyl, hydroxy-$C_1$–$C_4$-alkyl, $C_1$–$C_4$-alkoxy-$C_1$–$C_4$-alkyl, hydroxy-$C_1$–$C_4$-alkoxy-$C_1$–$C_4$-alkyl, phenyl or benzyl, preferably ammonium, dimethylammonium, diisopropylammonium, tetramethylammonium, tetrabutylammonium, 2-(2-hydroxyeth-1-oxy)eth-1-ylammonium, di(2-hydroxyeth-1-yl) ammonium, trimethylbenzylammonium, furthermore phosphonium ions, sulfonium ions, preferably tri($C_1$–$C_4$-alkyl) sulfonium and sulfoxonium ions, preferably tri($C_1$–$C_4$-alkyl)sulfoxonium.

Anions of useful acid addition salts are primarily chloride, bromide, fluoride, hydrogen sulfate, sulfate, dihydrogen phosphate, hydrogen phosphate, nitrate, hydrogen carbonate, carbonate, hexafluorosilicate, hexafluorophosphate, benzoate and also the anions of $C_1$–$C_4$-alkanoic acids, preferably formate, acetate, propionate and butyrate.

The organic moieties mentioned for the substituents $R^1$–$R^{12}$ or as radicals on phenyl and heterocyclyl radicals are collective terms for individual enumerations of the particular group members. All hydrocarbon chains, i.e. all alkyl, haloalkyl, alkoxy, haloalkoxy, alkylthio, haloalkylthio, alkylsulfynyl, haloalkylsulfynyl, alkylsulfonyl, haloalkylsulfonyl, N-alkylaminosulfonyl, N,N-dialkylaminosulfonyl, N-alkylamino, N,N-dialkylamino, N-haloalkylamino, N-alkoxyamino, N-alkoxy-N-alkylamino, N-alkylcarbonylamino, N-alkylsulfonylamino, N-haloalkylsulfonylamino, N-alkyl-N-alkylsulfonylamino, N-alkyl-N-haloalkylsulfonylamino, alkylcarbonyl, haloalkylcarbonyl, alkoxycarbonyl, haloalkoxycarbonyl, alkylthiocarbonyl, alkylcarbonyloxy, alkylaminocarbonyl, dialkylaminocarbonyl, dialkylaminothiocarbonyl, alkoxyalkyl, dialkoxymethyl, dialkylthiomethyl, (alkoxy)(alkylthio)methyl, alkylcarbonylalkyl, alkoxyiminomethyl, alkoxyiminoalkyl, N-(alkylamino)iminoalkyl, N-(dialkylamino)iminoalkyl, phenylalkenylcarbonyl, heterocyclylalkenylcarbonyl, phenoxyalkylcarbonyl, heterocyclyloxyalkylcarbonyl, N-alkoxy-N-alkylaminocarbonyl, N-alkyl-N-phenylaminocarbonyl, N-alkyl-N-heterocyclylaminocarbonyl, alkoxycarbonyloxy, phenylalkyl, heterocyclylalkyl, phenylcarbonylalkyl, heterocyclylcarbonylalkyl, dialkylaminoalkoxycarbonyl, alkoxyalkoxycarbonyl, alkenylcarbonyl, alkenyloxycarbonyl, alkenylaminocarbonyl, N-alkenyl-N-alkylaminocarbonyl, N-alkenyl-N-alkoxyaminocarbonyl, alkynylcarbonyl, alkynyloxycarbonyl, alkynylaminocarbonyl, N-alkynyl-N-alkylaminocarbonyl, N-alkynyl-N-alkoxyaminocarbonyl, alkenyl, alkynyl, haloalkenyl, haloalkynyl, alkenyloxy, alkynyloxy and alkoxyalkoxy moieties, may be straight-chain or branched. Unless indicated otherwise, halogenated substituents preferably carry one to five identical or different halogen atoms. The term "halogen" in each case represents fluorine, chlorine, bromine or iodine.

Examples of other meanings are:

$C_1$–$C_4$-alkyl: for example methyl, ethyl, propyl, 1-methylethyl, butyl, 1-methylpropyl, 2-methylpropyl or 1,1-dimethylethyl;

$C_1$–$C_6$-alkyl, and the alkyl moieties of $C_1$–$C_6$-alkoxyimino-$C_1$–$C_6$-alkyl, N—($C_1$–$C_6$-alkylamino)imino-$C_1$–$C_6$-alkyl, N-(di-$C_1$–$C_6$-alkylamino)imino-$C_1$–$C_6$-alkyl, N—($C_1$–$C_6$-alkoxy)-N-($C_1$–$C_6$-alkyl)-aminocarbonyl, N—($C_3$–$C_6$-alkenyl)-N-($C_1$–$C_6$-alkyl) aminocarbonyl, ($C_3$–$C_6$-alkynyl)-N-($C_1$–$C_6$-alkyl) aminocarbonyl, N—($C_1$–$C_6$-alkyl)-N-phenylaminocarbonyl, N—($C_1$–$C_6$-alkyl)-N-heterocyclylaminocarbonyl, phenyl-1-$C_6$-alkyl, N—($C_1$–$C_6$-alkyl)-N-($C_1$–$C_6$-alkylsulfonyl)amino, N—($C_1$–$C_6$-alkyl)-N($C_1$–$C_6$-haloalkylsulfonyl)amino, heterocyclyl-$C_1$–$C_6$-alkyl, phenylcarbonyl-$C_1$–$C_6$-alkyl, heterocyclylcarbonyl-$C_1$–$C_6$-alkyl: $C_1$–$C_4$-alkyl as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_6$-haloalkyl, and the haloalkyl moieties of N—$C_1$–$C_6$-haloalkylamino: $C_1$–$C_4$-haloalkyl, as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl or dodecafluorohexyl;

$C_1$–$C_4$-alkoxy: for example methoxy, ethoxy, propoxy, 1-methylethoxy, butoxy, 1-methylpropoxy, 2-methylpropoxy or 1,1-dimethylethoxy;

$C_1$–$C_6$-alkoxy, and the alkoxy moieties of N—$C_1$–$C_6$-alkoxyamino, di-($C_1$–$C_6$-alkoxy)methyl, ($C_1$–$C_6$-alkoxy)($C_1$–$C_6$-alkylthio)-methyl, $C_1$–$C_6$-alkoxyiminomethyl, $C_1$–$C_6$-alkoxyimino-$C_1$–$C_6$-alkyl, N—($C_1$–$C_6$-alkoxy)-N-($C_1$–$C_6$-alkyl) aminocarbonyl, N—($C_3$–$C_6$-alkenyl)-N-($C_1$–$C_6$-alkoxy)aminocarbonyl and N—($C_3$–$C_6$-alkynyl)-N-($C_1$–$C_6$-alkoxy)aminocarbonyl: $C_1$–$C_4$-alkoxy as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_6$-haloalkoxy: $C_1$–$C_4$-haloalkoxy as mentioned above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy or dodecafluorohexoxy;

$C_1$–$C_4$-alkylthio: for example methylthio, ethylthio, propylthio, 1-methylethylthio, butylthio, 1-methylpropylthio, 2-methylpropylthio or 1,1-dimethylethylthio;

$C_1$–$C_6$-alkylthio, and the alkylthio moieties of ($C_1$–$C_6$-alkylthio)carbonyl, di-($C_1$–$C_6$-alkylthio)methyl and ($C_1$–$C_6$-alkoxy)-($C_1$–$C_6$-alkylthio)methyl: $C_1$–$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio;

$C_1$–$C_{20}$-alkylthio as alkylthio radical of ($C_1$–$C_{20}$-alkylthio)carbonyl: $C_1$–$C_6$-alkylthio as mentioned above, and also, for example, heptylthio, octylthio, hexadecylthio or octadecylthio;

$C_1$–$C_4$-haloalkylthio: a $C_1$–$C_4$-alkylthio radical as mentioned above which is partially or fully substituted by fluorine, chlorine, bromine and/or iodine, i.e., for example, fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio or nonafluorobutylthio;

$C_1$–$C_6$-haloalkylthio: $C_1$–$C_4$-haloalkylthio, as mentioned above, and also, for example, 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio or dodecafluorohexylthio;

$C_1$–$C_6$-alkylsulfinyl ($C_1$–$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl;

$C_1$–$C_6$-haloalkylsulfinyl: a $C_1$–$C_6$-alkylsulfinyl radical as mentioned above which is partially or fully substituted by fluorine, chlorine, bromine and/or iodine, i.e., for example, fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl;

$C_1$–$C_6$-alkylsulfonyl ($C_1$–$C_6$-alkyl-S(=O)$_2$—), and the alkylsulfonyl radicals of N—($C_1$–$C_6$-alkylsulfonyl)amino and N—($C_1$–$C_6$-alkyl)-N-($C_1$–$C_6$-alkylsulfonyl)amino: for example, methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl;

$C_1$–$C_6$-haloalkylsulfonyl, and the haloalkylsulfonyl radicals of N—($C_1$–$C_6$-haloalkylsulfonyl)amino and N—($C_1$–$C_6$-alkyl)-N-($C_1$–$C_6$-haloalkylsulfonyl)amino: a $C_1$–$C_6$-alkylsulfonyl radical as mentioned above which is partially or fully substituted by fluorine, chlorine, bromine and/or iodine, i.e., for example, fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl, nonafluorobutylsulfonyl, 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl or dodecafluorohexylsulfonyl;

$C_1$–$C_6$-alkylamino, and the alkylamino radicals of N—($C_1$–$C_6$-alkylamino)imino-$C_1$–$C_6$-alkyl: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

($C_1$–$C_4$-alkylamino)sulfonyl: for example methylaminosulfonyl, ethylaminosulfonyl, propylaminosulfonyl, 1-methylethylaminosulfonyl, butylaminosulfonyl, 1-methylpropylaminosulfonyl, 2-methylpropylaminosulfonyl or 1,1-dimethylethylaminosulfonyl;

($C_1$–$C_6$-alkylamino)sulfonyl: ($C_1$–$C_4$-alkylamino)sulfonyl, as mentioned above, and also, for example, pentylaminosulfonyl, 1-methylbutylaminosulfonyl, 2-methylbutylaminosulfonyl, 3-methylbutylaminosulfonyl, 2,2-dimethylpropylaminosulfonyl, 1-ethylpropylaminosulfonyl, hexylaminosulfonyl, 1,1-dimethylpropylaminosulfonyl, 1,2-dimethylpropylaminosulfonyl, 1-methylpentylaminosulfonyl, 2-methylpentylaminosulfonyl, 3-methylpentylaminosulfonyl, 4-methylpentylaminosulfonyl, 1,1-dimethylbutylaminosulfonyl, 1,2-dimethylbutylaminosulfonyl, 1,3-dimethylbutylaminosulfonyl, 2,2-dimethylbutylaminosulfonyl, 2,3-dimethylbutylaminosulfonyl, 3,3-dimethylbutylaminosulfonyl, 1-ethylbutylaminosulfonyl, 2-ethylbutylaminosulfonyl, 1,1,2-trimethylpropylaminosulfonyl, 1,2,2-trimethylpropylaminosulfonyl, 1-ethyl-1-methylpropylaminosulfonyl or 1-ethyl-2-methylpropylaminosulfonyl;

di-($C_1$–$C_4$-alkyl)aminosulfonyl: for example N,N-dimethylaminosulfonyl, N,N-diethylaminosulfonyl, N,N-di-(1-methylethyl)aminosulfonyl, N,N-dipropylaminosulfonyl, N,N-dibutylaminosulfonyl, N,N-di-(1-methylpropyl)aminosulfonyl, N,N-di-(2-methylpropyl)aminosulfonyl, N,N-di-(1,1-dimethylethyl)aminosulfonyl, N-ethyl-N-methylaminosulfonyl, N-methyl-N-propylaminosulfonyl, N-methyl-N-(1-methylethyl)aminosulfonyl, N-butyl-N-methylaminosulfonyl, N-methyl-N-(1-methylpropyl)aminosulfonyl, N-methyl-N-(2-methylpropyl)aminosulfonyl, N-(1,1-dimethylethyl)-N-methylaminosulfonyl, N-ethyl-N-propylaminosulfonyl, N-ethyl-N-(1-methylethyl)aminosulfonyl, N-butyl-N-ethylaminosulfonyl, N-ethyl-N-(1-methylpropyl)aminosulfonyl, N-ethyl-N-(2-methylpropyl)aminosulfonyl, N-ethyl-N-(1,1-dimethylethyl)aminosulfonyl, N-(1-methylethyl)-N-propylaminosulfonyl, N-butyl-N-propyl aminosulfonyl, N-(1-methylpropyl)-N-propylaminosulfonyl, N-(2-methylpropyl)-N-propylaminosulfonyl, N-(1,1-dimethylethyl)-N-propylaminosulfonyl, N-butyl-N-(1-methylethyl)aminosulfonyl, N-(1-methylethyl)-N-(1-methylpropyl)aminosulfonyl, N-(1-methylethyl)-N-(2-methylpropyl)aminosulfonyl, N-(1,1-dimethylethyl)-N-(1-methylethyl)aminosulfonyl, N-butyl-N-(1-methylpropyl)aminosulfonyl, N-butyl-N-(2-methylpropyl)aminosulfonyl, N-butyl-N-(1,1-dimethylethyl)aminosulfonyl, N-(1-methylpropyl)-N-(2-methylpropyl)aminosulfonyl, N-(1,1-dimethylethyl)-N-(1-methylpropyl)aminosulfonyl or N-(1,1-dimethylethyl)-N-(2-methylpropyl)aminosulfonyl;

di-($C_1$–$C_6$-alkyl)aminosulfonyl: di-($C_1$–$C_4$-alkyl)aminosulfonyl, as mentioned above, and also, for example, N-methyl-N-pentylaminosulfonyl, N-methyl-N-(1-methylbutyl)aminosulfonyl, N-methyl-N-(2-methylbutyl)aminosulfonyl, N-methyl-N-(3-methylbutyl)aminosulfonyl, N-methyl-N-(2,2-dimethylpropyl)aminosulfonyl, N-methyl-N-(1-ethylpropyl)aminosulfonyl, N-methyl-N-hexylaminosulfonyl, N-methyl-N-(1,1-dimethylpropyl)aminosulfonyl, N-methyl-N-(1,2-dimethylpropyl)aminosulfonyl, N-methyl-N-(1-methylpentyl)aminosulfonyl, N-methyl-N-(2-methylpentyl)aminosulfonyl, N-methyl-N-(3-methylpentyl)aminosulfonyl, N-methyl-N-(4-methylpentyl)aminosulfonyl, N-methyl-N-(1,1-dimethylbutyl)aminosulfonyl, N-methyl-N-(1,2-dimethylbutyl)aminosulfonyl, N-methyl-N-(1,3-dimethylbutyl)aminosulfonyl, N-methyl-N-(2,2-dimethylbutyl)aminosulfonyl, N-methyl-N-(2,3-dimethylbutyl)aminosulfonyl, N-methyl-N-(3,3-dimethylbutyl)aminosulfonyl, N-methyl-N-(1-ethylbutyl)aminosulfonyl, N-methyl-N-(2-ethylbutyl)aminosulfonyl, N-methyl-N-(1,1,2-trimethylpropyl)aminosulfonyl, N-methyl-N-(1,2,2-trimethylpropyl)aminosulfonyl, N-methyl-N-(1-ethyl-1-methylpropyl)aminosulfonyl, N-methyl-N-(1-ethyl-2-methylpropyl)aminosulfonyl, N-ethyl-N-pentylaminosulfonyl, N-ethyl-N-(1-methylbutyl)aminosulfonyl, N-ethyl-N-(2-methylbutyl)aminosulfonyl, N-ethyl-N-(3-methylbutyl)aminosulfonyl, N-ethyl-N-(2,2-dimethypropyl)aminosulfonyl, N-ethyl-N-(1,1-ethylpropyl)aminosulfonyl, N-ethyl-N-hexylaminosulfonyl, N-ethyl-N-(1,1-dimethylpropyl)aminosulfonyl, N-ethyl-N-(1,2-dimethyl propyl)aminosulfonyl, N-ethyl-N-(1-methylpentyl)aminosulfonyl, N-ethyl-N-(2-methylpentyl)aminosulfonyl, N-ethyl-N-(3-methylpentyl)aminosulfonyl, N-ethyl-N-(4-methylpentyl)aminosulfonyl, N-ethyl-N-(1,1-methylbutyl)aminosulfonyl, N-ethyl-N-(1,2-dimethylbutyl)aminosulfonyl, N-ethyl-N-(1,3-dimethylbutyl)aminosulfonyl, N-ethyl-N-(2,2-dimethylbutyl)aminosulfonyl, N-ethyl-N-(2,3-dimethylbutyl)aminosulfonyl, N-ethyl-N-(3,3-dimethylbutyl)aminosulfonyl, N-ethyl-N-(1-ethylbutyl)aminosulfonyl, N-ethyl-N-(2-ethylbutyl)aminosulfonyl, N-ethyl-N-(1,1,2-trimethylpropyl)aminosulfonyl, N-ethyl-N-(1,2,2-trimethyl propyl)aminosulfonyl, N-ethyl-N-(1-ethyl-1-meth ylpropyl)aminosulfonyl, N-ethyl-N-(1-ethyl-2-methylpropyl)aminosulfonyl, N-propyl-N-pentylaminosulfonyl, N-butyl-N-pentylaminosulfonyl, N,N-dipentylaminosulfonyl, N-propyl-N-hexylaminosulfonyl, N-butyl-N-hexylaminosulfonyl, N-pentyl-N-hexylaminosulfonyl or N,N-dihexylaminosulfonyl;

di-($C_1$–$C_4$-alkyl)amino and the dialkylamino radicals of: di-($C_1$–$C_4$-alkyl)amino-$C_1$–$C_4$-alkoxycarbonyl and N-(di-$C_1$–$C_4$-alkylamino)imino-$C_1$–$C_6$-alkyl for example N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-

N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di-($C_1$–$C_6$-alkyl)amino, and the dialkylamino radicals of di-($C_1$–$C_6$-alkyl)amino-imino-$C_1$–$C_6$-alkyl: di-($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

$C_1$–$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl;

$C_1$–$C_6$-alkylcarbonyl, and the alkylcarbonyl radicals of phenoxy-$C_1$–$C_6$-alkylcarbonyl, heterocyclyloxy-$C_1$–$C_6$-alkylcarbonyl, $C_1$–$C_6$-alkylcarbonylamino, $C_1$–$C_6$-alkylcarbonyl-$C_1$–$C_6$-alkyl: $C_1$–$C_4$-alkylcarbonyl, as mentioned above, and also, for example, pentylcarbonyl, 1-methylbutylcarbonyl, 2-methylbutylcarbonyl, 3-methylbutylcarbonyl, 2,2-dimethylpropylcarbonyl, 1-ethylpropylcarbonyl, hexylcarbonyl, 1,1-dimethylpropylcarbonyl, 1,2-dimethylpropylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl or 1-ethyl-2-methylpropylcarbonyl;

$C_1$–$C_{20}$-alkylcarbonyl: $C_1$–$C_6$-alkylcarbonyl, as mentioned above, and also heptylcarbonyl, octylcarbonyl, pentadecylcarbonyl or heptadecylcarbonyl;

$C_1$–$C_6$-haloalkylcarbonyl: a $C_1$–$C_6$-alkylcarbonyl radical as mentioned above which is partially or fully substituted by fluorine, chlorine, bromine and/or iodine, i.e., for example, chloroacetyl, dichloroacetyl, trichloroacetyl, fluoroacetyl, difluoroacetyl, trifluoroacetyl, chlorofluoroacetyl, dichlorofluoroacetyl, chlorodifluoroacetyl, 2-fluoroethylcarbonyl, 2-chloroethylcarbonyl, 2-bromoethylcarbonyl, 2-iodoethylcarbonyl, 2,2-difluoroethylcarbonyl, 2,2,2-trifluoroethylcarbonyl, 2-chloro-2-fluoroethylcarbonyl, 2-chloro-2,2-fluoroethylcarbonyl, 2,2-dichloro-2-fluoroethylcarbonyl, 2,2,2-trichloroethylcarbonyl, pentafluoroethylcarbonyl, 2-fluoropropylcarbonyl, 3-fluoropropylcarbonyl, 2,2-difluoropropylcarbonyl, 2,3-difluoropropylcarbonyl, 2-chloropropylcarbonyl, 3-chloropropylcarbonyl, 2,3-dichloropropylcarbonyl, 2-bromopropylcarbonyl, 3-bromopropylcarbonyl, 3,3,3-trifluoropropylcarbonyl, 3,3,3-trichloropropylcarbonyl, 2,2,3,3,3-pentafluoropropylcarbonyl, heptafluoropropylcarbonyl, 1-(fluoromethyl)-2-fluoroethylcarbonyl, 1-(chloromethyl)-2-chloroethylcarbonyl, 1-(bromomethyl)-2-bromoethylcarbonyl, 4-fluorobutylcarbonyl, 4-chlorobutylcarbonyl, 4-bromobutylcarbonyl, nonafluorobutylcarbonyl, 5-fluoropentylcarbonyl, 5-chloropentylcarbonyl, 5-bromopentylcarbonyl, Perfluoropentylcarbonyl, 6-fluorohexylcarbonyl, 6-chlorohexylcarbonyl, 6-bromohexylcarbonyl or Perfluorohexylcarbonyl;

$C_1$–$C_4$-alkoxycarbonyl, and the alkoxycarbonyl moieties of di-($C_1$–$C_4$-alkyl)amino-$C_1$–$C_4$-alkoxycarbonyl, for example methoxycarbonyl, ethoxycarbonyl, propoxycarbonyl, 1-methylethoxycarbonyl, butoxycarbonyl, 1-methylpropoxycarbonyl, 2-methylpropoxycarbonyl or 1,1-dimethylethoxycarbonyl;

($C_1$–$C_6$-alkoxy)carbonyl, and the alkoxycarbonyl moieties of $C_1$–$C_6$-alkoxycarbonyloxy: ($C_1$–$C_4$-alkoxy)carbonyl, as mentioned above, and also, for example, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl or 1-ethyl-2-methylpropoxycarbonyl;

$C_1$–$C_6$-haloalkoxycarbonyl: a $C_1$–$C_6$-alkoxycarbonyl radical as mentioned above which is partially or fully substituted by fluorine, chlorine, bromine and/or iodine, i.e., for example, fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromethoxycarbonyl, 4-fluorobutoxycarbonyl, 4-chlorobutoxycarbonyl, 4-bromobutoxycarbonyl, 4-iodobutoxycarbonyl, 5-fluoropentoxycarbonyl, 5-chloropentoxycarbonyl, 5-bromopentoxycarbonyl, 6-fluorohexoxycarbonyl, 6-chlorohexoxycarbonyl or 6-bromohexoxycarbonyl;

($C_1$–$C_4$-alkyl)carbonyloxy: acetyloxy, ethylcarbonyloxy, propylcarbonyloxy, 1-methylethylcarbonyloxy, butylcarbonyloxy, 1-methylpropylcarbonyloxy, 2-methylpropylcarbonyloxy or 1,1-dimethylethylcarbonyloxy;

($C_1$–$C_4$-alkylamino)carbonyl: for example methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl or 1,1-dimethylethylaminocarbonyl;

($C_1$–$C_6$-alkylamino)carbonyl: ($C_1$–$C_4$-alkylamino)carbonyl, as mentioned above, and also, for example, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl or 1-ethyl-2-methylpropylaminocarbonyl;

di-($C_1$–$C_4$-alkyl)aminocarbonyl: for example N,N-dimethylaminocarbonyl, N,N-diethylaminocarbonyl, N,N-di-(1-methylethyl)aminocarbonyl, N,N-dipropylaminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl) aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl;

di-($C_1$–$C_6$-alkyl)aminocarbonyl: di-($C_1$–$C_4$-alkyl)aminocarbonyl as mentioned above, and also, for example, N-methyl-N-pentylaminocarbonyl, N-methyl-N-(1-methylbutyl)aminocarbonyl, N-methyl-N-(2-methylbutyl)aminocarbonyl, N-methyl-N-(3-methylbutyl)aminocarbonyl, N-methyl-N-(2,2-dimethylpropyl)aminocarbonyl, N-methyl-N-(1-ethylpropyl)aminocarbonyl, N-methyl-N-hexylaminocarbonyl, N-methyl-N-(1,1-dimethylpropyl)aminocarbonyl, N-methyl-N-(1,2-dimethylpropyl)aminocarbonyl, N-methyl-N-(1-methylpentyl)aminocarbonyl, N-methyl-N-(2-methylpentyl)aminocarbonyl, N-methyl-N-(3-methylpentyl)aminocarbonyl, N-methyl-N-(4-methylpentyl)aminocarbonyl, N-methyl-N-(1,1-dimethylbutyl)aminocarbonyl, N-methyl-N-(1,2-dimethylbutyl)aminocarbonyl, N-methyl-N-(1,3-dimethylbutyl)aminocarbonyl, N-methyl-N-(2,2-dimethylbutyl)aminocarbonyl, N-methyl-N-(2,3-dimethylbutyl)aminocarbonyl, N-methyl-N-(3,3-dimethylbutyl)aminocarbonyl, N-methyl-N-(1-ethylbutyl)aminocarbonyl, N-methyl-N-(2-ethylbutyl)aminocarbonyl, N-methyl-N-(1,1,2-trimethylpropyl)aminocarbonyl, N-methyl-N-(1,2,2-trimethylpropyl)aminocarbonyl, N-methyl-N-(1-ethyl-1-methylpropyl)aminocarbonyl, N-methyl-N-(1-ethyl-2-methylpropyl)aminocarbonyl, N-ethyl-N-pentylaminocarbonyl, N-ethyl-N-(1-methylbutyl)aminocarbonyl, N-ethyl-N-(2-methylbutyl)aminocarbonyl, N-ethyl-N-(3-methylbutyl)aminocarbonyl, N-ethyl-N-(2,2-dimethylpropyl)aminocarbonyl, N-ethyl-N-(1-ethylpropyl)aminocarbonyl, N-ethyl-N-hexylaminocarbonyl, N-ethyl-N-(1,1-dimethylpropyl)aminocarbonyl, N-ethyl-N-(1,2-dimethylpropyl)aminocarbonyl, N-ethyl-N-(1-methylpentyl)aminocarbonyl, N-ethyl-N-(2-methylpentyl)aminocarbonyl, N-ethyl-N-(3-methylpentyl)aminocarbonyl, N-ethyl-N-(4-methylpentyl)aminocarbonyl, N-ethyl-N-(1,1-dimethylbutyl)aminocarbonyl, N-ethyl-N-(1,2-dimethylbutyl)aminocarbonyl, N-ethyl-N-(1,3-dimethylbutyl)aminocarbonyl, N-ethyl-N-(2,2-dimethylbutyl)aminocarbonyl, N-ethyl-N-(2,3-dimethylbutyl)aminocarbonyl, N-ethyl-N-(3,3-dimethylbutyl)aminocarbonyl, N-ethyl-N-(1-ethylbutyl)aminocarbonyl, N-ethyl-N-(2-ethylbutyl)aminocarbonyl, N-ethyl-N-(1,1,2-trimethylpropyl)aminocarbonyl, N-ethyl-N-(1,2,2-trimethylpropyl)aminocarbonyl, N-ethyl-N-(1-ethyl-1-methylpropyl)aminocarbonyl, N-ethyl-N-(1-ethyl-2-methylpropyl)aminocarbonyl, N-Propyl-N-pentylaminocarbonyl, N-butyl-N-pentylaminocarbonyl, N,N-dipentylaminocarbonyl, N-Propyl-N-hexylaminocarbonyl, N-butyl-N-hexylaminocarbonyl, N-pentyl-N-hexylaminocarbonyl or N,N-dihexylaminocarbonyl;

di-($C_1$–$C_6$-alkyl)aminothiocarbonyl: for example N,N-dimethylaminothiocarbonyl, N,N-diethylaminothiocarbonyl, N,N-di-(1-methylethyl)aminothiocarbonyl, N,N-dipropylaminothiocarbonyl, N,N-dibutylaminothiocarbonyl, N,N-di-(1-methylpropyl)aminothiocarbonyl, N,N-di-(2-methylpropyl)aminothiocarbonyl, N,N-di-(1,1-dimethylethyl)aminothiocarbonyl, N-ethyl-N-methylaminothiocarbonyl, N-methyl-N-propylaminothiocarbonyl, N-methyl-N-(1,1-methylethyl)aminothiocarbonyl, N-butyl-N-methylaminothiocarbonyl, N-methyl-N-(1-methyipropyl)aminothiocarbonyl, N-methyl-N-(2-methyipropyl)aminothiocarbonyl, N-(1,1-dimethylethyl)-N-methylaminothiocarbonyl, N-ethyl-N-propylaminothiocarbonyl, N-ethyl-N-(1-methylethyl)aminothiocarbonyl, N-butyl-N-ethylaminothiocarbonyl, N-ethyl-N-(1-methylpropyl)aminothiocarbonyl, N-ethyl-N-(2-ethylpropyl)-aminothiocarbonyl, N-ethyl-N-(1,1-dimethylethyl)-aminothiocarbonyl, N-(1,1-methylethyl)N-propylaminothiocarbonyl, N-butyl-N-propylaminothiocarbonyl, N-(1-methylpropyl)-N-propylaminothiocarbonyl, N-(2-methylpropyl)-N-propylaminothiocarbonyl, N-(1,1-dimethylethyl)-N-propylaminothiocarbonyl, N-butyl-N-(1,1-methylethyl)aminothiocarbonyl, N-(1-methylethyl)-N-(1-methylpropyl)aminothiocarbonyl, N-(1-methylethyl)-N-(2-methylpropyl) aminothiocarbonyl, N-(1,1-dimethylethyl)-N-(1-methylethyl)aminothiocarbonyl, N-butyl-N-(1-methylpropyl) aminothiocarbonyl, N-butyl-N-(2-methylpropyl)aminothiocarbonyl, N-butyl-N-(1,1-dimethylethyl)aminothiocarbonyl, N-(1-methylpropyl)-N-(2-methylpropyl)aminothiocarbonyl, N-(1,1-dimethylethyl)-N-(1-methylpropyl)aminothiocarbonyl, N-(1,1-dimethylethyl)-N-(2-methylpropyl)aminothiocarbonyl, N-methyl-N-pentylaminothiocarbonyl, N-methyl-N-(1-methylbutyl)aminothiocarbonyl, N-methyl-N-(2-methylbutyl) aminothiocarbonyl, N-methyl-N-(3-methylbutyl)aminothiocarbonyl, N-methyl-N-(2,2-dimethylpropyl)aminothiocarbonyl, N-methyl-N-(1-ethylpropyl)aminothiocarbonyl, N-methyl-N-hexylaminothiocarbonyl, N-methyl-N-(1,1-dimethyipropyl) aminothiocarbonyl, N-methyl-N-(1,2-dimethylpropyl)aminothiocarbonyl, N-methyl-N-(1-methylpentyl) aminothiocarbonyl, N-methyl-N-(2-methylpentyl)aminothiocarbonyl, N-methyl-N-(3-methylpentyl)aminothiocarbonyl, N-methyl-N-(4-methylpentyl)aminothiocarbonyl, N-methyl-N-(1,1-dimethylbutyl)aminothiocarbonyl, N-methyl-N-(1,2-dimethylbutyl)aminothiocarbonyl, N-methyl-N-(1,3-dimethylbutyl)aminothiocarbonyl, N-methyl-N-(2,2-dimethylbutyl)aminothiocarbonyl, N-methyl-N-(2,3-dimethylbutyl) aminothiocarbonyl, N-methyl-N-(3,3-dimethylbutyl)aminothiocarbonyl, N-methyl-N-(1-ethylbutyl)aminothiocarbonyl, N-methyl-N-(2-ethylbutyl)aminothiocarbonyl, N-methyl-N-ethyl-N-(1,1,2-trimethylpropyl)aminothiocarbonyl, N-methyl-N-(1,2,2-trimethylpropyl)aminothiocarbonyl, N-methyl-N-(1-ethyl-1-methylpropyl)aminothiocarbonyl, N-methyl-N-(1-ethyl-2-methylpropyl)aminothiocarbonyl, N-ethyl-N-pentylaminothiocarbonyl, N-ethyl-N-(1-methylbutyl)aminothiocarbonyl, N-ethyl-N-(2-methylbutyl)aminothiocarbonyl, N-ethyl-N-(3-methylbutyl)aminothiocarbonyl, N-ethyl-N-(2,2-dimethylpropyl)aminothiocarbonyl, N-ethyl-N-(1-ethylpropyl)aminothiocarbonyl, N-ethyl-N-hexylaminothiocarbonyl, N-ethyl-N-(1,1-dimethylpropyl)aminothiocarbonyl, N-ethyl-N-(1,2-dimethylpropyl)aminothiocarbonyl, N-ethyl-N-(1-methylpentyl)aminothiocarbonyl, N-ethyl-N-(2-methylpentyl)aminothiocarbonyl, N-ethyl-N-(3-methylpentyl)aminothiocarbonyl, N-ethyl-N-(4-methylpentyl)aminothiocarbonyl, N-ethyl-N-(1,1-dimethylbutyl)aminothiocarbonyl, N-ethyl-N-(1,2-dimethylbutyl)aminothiocarbonyl, N-ethyl-N-(1,3-dimethylbutyl)aminothiocarbonyl, N-ethyl-N-(2,2-dimethylbutyl)aminothiocarbonyl, N-ethyl-N-(2,3-dimethylbutyl)aminothiocarbonyl, N-ethyl-N-(3,3-dimethylbutyl)aminothiocarbonyl, N-ethyl-N-(1-ethylbutyl)aminothiocarbonyl, N-ethyl-N-(2-ethylbutyl)aminothiocarbonyl, N-ethyl-N-(1,1,2-trimethylpropyl)aminothiocarbonyl, N-ethyl-N-(1,2,2-trimethylpropyl)aminothiocarbonyl, N-ethyl-N-(1-ethyl-1-methylpropyl)aminothiocarbonyl, N-ethyl-N-(1-ethyl-2-methylpropyl)aminothiocarbonyl, N-Propyl-N-pentylaminothiocarbonyl, N-butyl-N-pentylaminothiocarbonyl, N,N-dipentylaminothiocarbonyl, N-Propyl-N-hexylaminothiocarbonyl, N-butyl-N-hexylaminothiocarbonyl, N-pentyl-N-hexylaminothiocarbonyl or N,N-dihexylaminothiocarbonyl;

$C_1$–$C_4$-alkoxy-$C_1$–$C_4$-alkyl: $C_1$–$C_4$-alkyl which is substituted by $C_1$–$C_4$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(propoxy)ethyl, 2-(1-methylethoxy)ethyl, 2-(butoxy)ethyl, 2-(1-methylpropoxy)ethyl, 2-(2-methylpropoxy)ethyl, 2-(1,1-dimethylethoxy)ethyl, 2-(methoxy)-propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy)propyl, 3-(1-methylethoxy)propyl, 3-(butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl or 4-(1,1-dimethylethoxy)butyl;

$C_1$–$C_4$-alkoxy-$C_1$–$C_4$-alkoxy, and the alkoxyalkoxy moieties of $C_1$–$C_4$-alkoxy-$C_1$–$C_4$-alkoxycarbonyl: $C_1$–$C_4$-alkoxy which is substituted by $C_1$–$C_4$-alkoxy as mentioned above, i.e., for example, methoxymethoxy, ethoxymethoxy, propoxymethoxy, (1-methylethoxy)methoxy, butoxymethoxy, (1-methylpropoxy)methoxy, (2-methylpropoxy)methoxy, (1,1-dimethylethoxy)methoxy, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy or 4-(1,1-dimethylethoxy)butoxy;

$C_3$–$C_6$-alkenyl, and the alkenyl moieties of $C_3$–$C_6$-alkenylcarbonyl, $C_3$–$C_6$-alkenyloxy, $C_3$–$C_6$-alkenyloxycarbonyl, $C_3$–$C_6$-alkenylaminocarbonyl, N—($C_3$–$C_6$-alkenyl)-N-($C_1$–$C_6$alkyl) aminocarbonyl, N—($C_3$–$C_6$-alkenyl)-N-($C_1$–$C_6$-alkoxy)aminocarbonyl: for example prop-2-en-1-yl, but-1-en-4-yl, 1-methyl-prop-2-en-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-ethylpent-3-en-1-yl, 4-ethylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 2,3-ethylbut-2-en-1-yl, 1-ethylbut-3-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkenyl, and the alkenyl moieties of $C_2$–$C_6$-alkenylcarbonyl, phenyl-$C_2$–$C_6$-alkenylcarbonyl and heterocyclyl-$C_2$–$C_6$-alkenylcarbonyl: $C_3$–$C_6$-alkenyl as mentioned above, and also ethenyl;

$C_3$–$C_6$-haloalkenyl: a $C_3$–$C_6$-alkenyl radical as mentioned above which is partially or fully substituted by fluorine, chlorine, bromine and/or iodine, i.e., for example, 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl, and the alkyinyl moieties of $C_3$–$C_6$-alkynylcarbonyl, $C_3$–$C_6$-alkynyloxy, $C_3$–$C_6$-alkynyloxycarbonyl, $C_3$–$C_6$-alkynylaminocarbonyl, N—($C_3$–$C_6$-alkynyl)-N-($C_1$–$C_6$-alkyl)aminocarbonyl, N—($C_3$–$C_6$-alkynyl)-N-($C_1$–$C_6$-alkoxyaminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methyl-but-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl, and the alkynyl moieties of $C_2$–$C_6$alkynylcarbonyl: $C_3$–$C_6$-alkynyl as mentioned above, and also ethynyl;

$C_3$–$C_6$-haloalkynyl: a $C_3$–$C_6$-alkynyl radical as mentioned above which is partially or fully substituted by fluorine, chlorine, bromine and/or iodine, i.e., for example, 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_3$–$C_6$-cycloalkyl, and the cycloalkyl moieties of $C_3$–$C_6$-cycloalkylcarbonyl: for example cyclopropyl, cyclobutyl, cyclopentyl or cyclohexyl;

heterocyclyl, and the heterocyclyl moieties of heterocyclylcarbonyl, heterocyclyl-$C_1$–$C_6$-alkyl, heterocyclyloxy, heterocyclylthio, heterocyclyloxyalkylcarbonyl, heterocyclyloxycarbonyl, heterocyclyloxythiocarbonyl, heterocyclylcarbonyl-$C_1$–$C_6$-alkyl, N—($C_1$–$C_6$-alkyl)-N-(heterocyclyl)aminocarbonyl, heterocyclylaminocarbonyl: a saturated, partially saturated or unsaturated 5- or 6-membered heterocyclic ring which is attached via a carbon and has one to four identical or different hetero atoms selected from the following group: oxygen, sulfur or nitrogen, i.e., for example, 5-membered rings having a hetero atom such as, for example: tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl or pyrrol-3-yl;

5-membered rings having two hetero atoms such as, for example, tetrahydropyrazol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl or thiazol-5-yl;

5-membered rings having 3 hetero atoms such as, for example, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$- oxadiazolin-3-yl, 1,2,4-Δ³-oxadiazolin-5-yl, 1,3,4-Δ²-oxadiazolin-2-yl, 1,3,4-Δ²-oxadiazolin-5-yl, 1,3,4-Δ³-oxadiazolin-2-yl, 1,3,4-oxadiazolin-2-yl, 1,2,4-Δ⁴-thiadiazolin-3-yl, 1,2,4-Δ⁴-thiadiazolin-5-yl, 1,2,4-Δ³-thiadiazolin-3-yl, 1,2,4-Δ³-thiadiazolin-5-yl, 1,2,4-Δ²-thiadiazolin-3-yl, 1,2,4-Δ²-thiadiazolin-5-yl, 1,2,4-Δ²-thiadiazolin-2-yl, 1,3,4-Δ²-thiadiazolin-5-yl, 1,3,4-Δ³-thiadiazolin-2-yl, 1,3,4-thiadiazolin-2-yl, 1,3,2-dioxathiolan-4-yl, 1,2,3-Δ²-triazolin-4-yl, 1,2,3-Δ²-triazolin-5-yl, 1,2,3-Δ²-triazolin-3-yl, 1,2,4-Δ²-triazolin-5-yl, 1,2,4-Δ³-triazolin-3-yl, 1,2,4-Δ³-triazolin-5-yl, 1,2,4-Δ¹-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl or 1,2,4-triazol-3-yl;

5-membered rings having 4 hetero atoms such as, for example, tetrazol-5-yl, 6-membered rings having 1 hetero atom such as, for example:

tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydropyran-5-yl, 2H-5,6-dihydrothiopyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl or pyridin-4-yl;

6-membered rings having 2 hetero atoms such as, for example, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin- 2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl, pyridazin-3-yl, pyridazin-4-yl, pyrimidin-2-yl, pyrimidin-4-yl, pyrimidin-5-yl or pyrazin-2-yl;

6-membered rings having 3 hetero atoms such as, for example,
1,3,5-triazin-2-yl, 1,2,4-triazin-3-yl, 1,2,4-triazin-5-yl or 1,2,4-triazin-6-yl;

6-membered rings having 4 hetero atoms such as, for example,
1,2,4,5-tetrazin-3-yl;

where, if appropriate, the sulfur of the abovementioned heterocycles may be oxidized to S=o or S(=O)$_2$;

and where a bicyclic ring system may be formed with a fused-on phenyl ring or with a $C_3$–$C_6$-carbocycle or with another 5- to 6-membered heterocycle.

N-linked heterocyclyl: a saturated, partially saturated or unsaturated 5- or 6-membered heterocyclic ring which is attached via nitrogen and which contains at least one nitrogen and optionally one to three identical or different hetero atoms selected from the following group: oxygen, sulfur or nitrogen, i.e., for example, 5-membered rings having 1 hetero atom which are linked by a nitrogen, such as, for example,
tetrahydropyrrol-1-yl, 2,3-dihydro-1H-pyrrol-1-yl, 2,5-dihydro-1H-pyrrol-1-yl or pyrrol-1-yl;

5-membered rings having 2 hetero atoms which are linked by a nitrogen such as, for example,
tetrahydropyrazol-1-yl, tetrahydroisoxazol-2-yl, tetrahydroisothiazol-2-yl, tetrahydroimidazol-1-yl, tetrahydroooxazol-3-yl, tetrahydrothiazol-3-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, pyrazol-1-yl or imidazol-1-yl;

5-membered rings having 3 hetero atoms which are linked by a nitrogen such as, for example,
1,2,4-Δ$^4$-oxadiazolin-2-yl, 1,2,4-Δ$^2$-oxadiazolin-4-yl, 1,2,4-Δ$^3$-oxadiazolin-2-yl, 1,3,4-Δ$^2$-oxadiazolin-4-yl, 1,2,4-Δ$^2$-thiadiazolin-2-yl, 1,2,4-Δ$^3$-thiadiazolin-2-yl, 1,2,4-Δ$^2$-thiadiazolin-4-yl, 1,3,4-Δ$^2$-thiadiazolin-4-yl, 1,2,3-Δ$^2$-triazolin-1-yl, 1,2,4-Δ$^2$-triazolin-1-yl, 1,2,4-Δ$^2$-triazolin-4-yl, 1,2,4-Δ$^3$-triazolin-1-yl, 1,2,4-Δ$^1$-triazolin-4-yl, 1,2,3-triazol-1-yl or 1,2,4-triazol-1-yl;

5-membered rings having 4 hetero atoms which are linked by a nitrogen such as, for example,
tetrazol-1-yl;

and 6-membered rings having 1 hetero atom which are linked by a nitrogen, such as, for example
piperidin-1-yl, 1,2,3,4-tetrahydropyridin-1-yl, 1,2,5,6-tetrahydropyridin-1-yl, 1,4-dihydropyridin-1-yl or 1,2-dihydropyridin-1-yl;

6-membered rings having 2 hetero atoms which are linked by a nitrogen such as, for example,
hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl, and also cyclic imides which are linked via nitrogen, such as: phthalimide, tetrahydrophthalimide, succinimide, maleimide or glutarimide, and also 4-oxo-1,4-dihydropyridin-1-yl.

All phenyl rings or heterocyclyl radicals, and also all phenyl components in phenyl-$C_1$–$C_6$-alkyl, phenylcarbonyl-$C_1$–$C_6$-alkyl, phenoxy, phenylthio, phenylcarbonyl, phenylalkenylcarbonyl, phenoxycarbonyl, phenoxyalkylcarbonyl, phenylaminocarbonyl and N—($C_1$–$C_6$-alkyl)-N-phenylaminocarbonyl or heterocyclyl components in heterocyclyl-$C_1$–$C_6$-alkyl, heterocyclylcarbonyl-$C_1$–$C_6$-alkyl, heterocyclyloxy, heterocyclylthio, heterocyclylcarbonyl, heterocyclylalkenylcarbonyl, heterocyclyloxyalkylcarbonyl, heterocyclyloxycarbonyl, heterocyclylaminocarbonyl and N—($C_1$–$C_6$-alkyl)-N-heterocyclylaminocarbonyl are, unless stated otherwise, preferably unsubstituted, or they carry one to three halogen atoms and/or one nitro group, one cyano radical and/or one or two methyl, trifluoromethyl, methoxy or trifluoromethoxy substituents.

The compounds of the formula I according to the invention where $R^4$=IIa are referred to as compounds of the formula Ia, and compounds of the formula I where $R^4$=IIb are referred to as Ib.

The compounds of the formula I should be particularly emphasized, where $R^7$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-Cycloalkyl, $C_1$–$C_{20}$-alkylcarbonyl, $C_2$–$C_6$-alkenylcarbonyl, $C_2$–$C_6$-alkynylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di-($C_1$–$C_6$-alkyl)-aminocarbonyl, N—($C_3$–$C_6$-alkenyl)-N-($C_1$–$C_6$-alkyl) aminocarbonyl, N—($C_3$–$C_6$-alkynyl)-N-($C_1$–$C_6$-alkyl) aminocarbonyl, N—($C_1$–$C_6$-alkoxy)-N-($C_1$–$C_6$-alkyl) aminocarbonyl, N—($C_3$–$C_6$-alkenyl)-N-($C_1$–$C_6$-alkoxy) aminocarbonyl, N—($C_3$–$C_6$-alkynyl)-N-($C_1$–$C_6$-alkoxy)-aminocarbonyl, di-($C_1$–$C_6$-alkyl)aminothiocarbonyl, $C_1$–$C_6$-alkylcarbonyl-$C_1$–$C_6$-alkyl, $C_1$–$C_6$-alkoxyimino-$C_1$–$C_6$-alkyl, N—($C_1$–$C_6$-alkylamino)imino-$C_1$–$C_6$-alkyl or N,N-di-($C_1$–$C_6$-alkylamino)imino-$C_1$–$C_6$-alkyl, where the alkyl, cycloalkyl and alkoxy radicals mentioned may be partially or fully halogenated and/or may carry one to thre of the following groups:

cyano, $C_1$–$C_4$-alkoxy, $C_1$–$C_4$-alkylthio, di-($C_1$–$C_4$-alkyl) amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl) amino-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, heterocyclyloxycarbonyl, phenoxythiocarbonyl, heterocyclyloxythiocarbonyl, phenoxy-$C_1$–$C_6$-alkylcarbonyl, heterocyclyloxy-$C_1$–$C_6$alkylcarbonyl, phenylaminocarbonyl, N—($C_1$–$C_6$-alkyl)-N-(phenyl) aminocarbonyl, heterocyclylaminocarbonyl, N—($C_1$–$C_6$-alkyl)-N-(heterocyclyl)aminocarbonyl, phenyl-$C_2$–$C_6$-alkenylcarbonyl or heterocyclyl-$C_2$–$C_6$-alkenylcarbonyl, where the phenyl and the heterocyclyl radical of the 20 last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

With a view to the use of the compounds of the formula I according to the invention as herbicides, the variables preferably have the following meanings, in each case on their own or in combination:

$R^1$ is nitro, halogen, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfonyl or $C_1$–$C_6$-haloalkylsulfonyl;

$R^2$, $R^3$ are hydrogen, $C_1$–$C_6$-alkyl or halogen;

$R^4$ is a compound of IIa or IIb

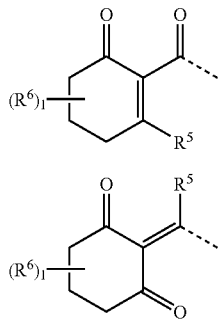

IIa

IIb where $R^5$ is halogen, $OR^7$, $SR^7$, $SO_2R^8$, $OSO_2R^8$, $OPOR^8R^9$, $OPR^8R^9$, $OPSR^8R^9$, $NR^{10}R^{11}$, $ONR^{11}R^12$, N-linked heterocyclyl or O—(N-linked heterocyclyl), where the heterocyclyl radical of the two last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^6$ is halogen, cyano, $C_1$–$C_6$-alkyl, $C_1$–$C_6$-haloalkyl, di-($C_1$–$C_6$-alkoxy)methyl, di-($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkoxycarbonyloxy, $C_1$–$C_6$-alkylthio, $C_1$–$C_6$-haloalkylthio, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl;

or two radicals $R^6$, which are linked to the same carbon, together form an —O—$(CH_2)_m$—O—, —O—$(CH_2)_m$—S—, —S—$(CH_2)_m$—S—, —O—$(CH_2)_n$- or —S—$(CH_2)_n$-chain which may be substituted by one to three radicals from the following group:

halogen, cyano, $C_1$–$C_4$-alkyl, $C_1$–$C_4$-haloalkyl or $C_1$–$C_4$-alkoxycarbonyl;

or two radicals $R^6$, which are linked to the same carbon, together form a-$(CH_2)_p$ chain which may be interrupted by oxygen or sulfur and/or may be substituted by one to four radicals from the following group:

halogen, cyano, $C_1$–$C_4$-alkyl, $C_1$–$C_4$-haloalkyl or $C_1$–$C_4$-alkoxycarbonyl;

or two radicals $R^6$, which are linked to the same carbon, together with this carbon form a carbonyl group;

or two radicals $R^6$, which are linked to different carbons, together form a-$(CH_2)_n$ chain which may be substituted by one to three radicals from the following group:

halogen, $C_1$–$C_6$-alkyl, $C_1$–$C_6$-alkoxy, hydroxyl or $C_1$–$C_6$-alkoxycarbonyl;

$R^7$ is $C_1$–$C_6$-alkyl, $C_3$–$C_6$-alkenyl, $C_3$–$C_6$-haloalkenyl, $C_3$–$C_6$-alkynyl, $C_1$–$C_{20}$-alkylcarbonyl, $C_2$–$C_6$-alkenylcarbonyl, $C_3$–$C_6$-cycloalkylcarbonyl, $C_1$–$C_6$-alkoxycarbonyl, $C_3$–$C_6$-alkenyloxycarbonyl, $C_3$–$C_6$-alkynyloxycarbonyl, ($C_1$–$C_{20}$-alkylthio)carbonyl (particularly preferably ($C_1$–$C_6$-alkylthio)carbonyl), $C_1$–$C_6$-alkylaminocarbonyl, $C_3$–$C_6$-alkenylaminocarbonyl, $C_3$–$C_6$-alkynylaminocarbonyl, N,N-di-($C_1$–$C_6$-alkyl)aminocarbonyl, N—($C_3$–$C_6$-alkenyl)-N-($C_1$–$C_6$-alkyl) aminocarbonyl, N—($C_3$–$C_6$-alkynyl)-N-($C_1$–$C_6$-alkyl)aminocarbonyl, N—($C_1$–$C_6$-alkoxy)-N-($C_1$–$C_6$-alkyl)aminocarbonyl, N—($C_3$–$C_6$-alkenyl)-N-($C_1$–$C_6$-alkoxy) aminocarbonyl, N—($C_3$–$C_6$-alkynyl)-N-($C_1$–$C_6$-alkoxy) aminocarbonyl, di-($C_1$–$C_6$-alkyl)aminothiocarbonyl, $C_1$–$C_6$-alkylcarbonyl-$C_1$–$C_6$-alkyl, $C_1$–$C_6$-alkoxyimino-$C_1$–$C_6$-alkyl, N—($C_1$–$C_6$-alkylamino)imino-$C_1$–$C_6$-alkyl or N,N-di-($C_1$–$C_6$-alkylamino)imino-$C_1$–$C_6$-alkyl, where the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;

phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, heterocyclyloxycarbonyl, phenoxythiocarbonyl, heterocyclyloxythiocarbonyl, phenoxy-$C_1$–$C_6$-alkylcarbonyl, heterocyclyloxy-$C_1$–$C_6$-alkylcarbonyl, phenyl-$C_2$–$C_6$-alkenylcarbonyl or heterocyclyl-$C_2$–$C_6$-alkenylcarbonyl, where the phenyl and the heterocyclyl radical of the 16 last mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^8$, $R^9$ are $C_1$–$C_6$-alkyl, $C_3$–$C_6$-alkenyl, $C_3$–$C_6$-haloalkenyl, $C_3$–$C_6$-cycloalkyl, hydroxy, $C_1$–$C_6$-alkoxy, di-$C_1$–$C_6$- alkylamino, or di-($C_1$–$C_6$-haloalkyl)amino, where the abovementioned alkyl, cycloalkyl and alkoxy radicals may be partially or fully halogenated and/or may carry one to three of the following groups:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;
phenyl, heterocyclyl, phenyl-$C_1$–$C_6$-alkyl, heterocyclyl-$C_1$–$C_6$-alkyl, phenoxy, heterocyclyloxy, where the phenyl- and the heterocyclyl radical of the last-mentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^{10}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy, $C_3$–$C_6$-alkenyloxy or di-($C_1$–$C_6$-alkyl)amino, where the abovementioned alkyl, cycloalkyl and alkoxy radicals may be partially or fully halogenated and/or may carry one to three radicals from the following group:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;
phenyl, heterocyclyl, phenyl-$C_1$–$C_6$-alkyl or heterocyclyl-$C_1$–$C_6$-alkyl, where the phenyl or heterocyclyl radical of the four last-mentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^{11}$, $R^{12}$ are $C_1$–$C_6$-alkyl or $C_3$–$C_6$-alkenyl;
l 0 to 6;
m 2 to 4;
n 1 to 5;
p 2 to 5.

Particular preference is given to compounds of the formula I where the variables have the following meanings, either on their own or in combination:
$R^1$ is halogen, $C_1$–$C_6$-alkyl, $C_1$–$C_6$-haloalkyl, $C_1$–$C_6$-alkoxy, $C_1$–$C_6$-alkylthio or $C_1$–$C_6$-alkylsulfonyl; in particular halogen, such as fluorine or chlorine, $C_1$–$C_6$-alkyl, such as methyl or ethyl, $C_1$–$C_6$-haloalkyl, such as difluoromethyl or trifluoromethyl; particularly preferably fluorine, chlorine, methyl, difluoromethyl or trifluoromethyl;
$R^2$ is hydrogen or $C_1$–$C_6$-alkyl, such as methyl or ethyl; in particular hydrogen or methyl;
$R^3$ is hydrogen or $C_1$–$C_6$-alkyl; in particular hydrogen;
$R^4$ is a compound IIa or IIb

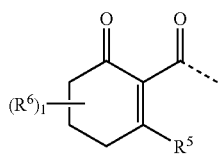

IIa

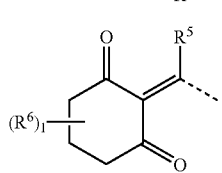

IIb where
$R^5$ is halogen, $OR^7$, $SR^7$, $SO_2R^8$, $OSO_2R^8$, $NR^{10}R^{11}$, $ONR^{11}R^{12}$, N-linked heterocyclyl or O—(N-linked heterocyclyl), where the heterocyclyl radical of the two last-mentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^6$ is halogen, cyano, $C_1$–$C_6$-alkyl, $C_1$–$C_6$-haloalkyl, di-($C_1$–$C_6$-alkoxy)methyl, di-($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkoxycarbonyloxy, $C_1$–$C_6$-alkylthio or $C_1$–$C_6$-haloalkylthio;
or
two radicals $R^6$, which are linked to the same carbon, together with this carbon form a carbonyl group;
$R^7$ is $C_1$–$C_6$-alkyl, $C_3$–$C_6$-alkenyl, $C_3$–$C_6$-haloalkenyl, $C_3$–$C_6$-alkynyl, $C_1$–$C_{20}$-alkylcarbonyl, $C_3$–$C_6$-cycloalkylcarbonyl, $C_1$–$C_6$-alkoxycarbonyl, $C_3$–$C_6$-alkenyloxycarbonyl, $C_1$–$C_6$-alkylaminocarbonyl, $C_3$–$C_6$-alkenylaminocarbonyl, N,N-di-($C_1$–$C_6$-alkyl)aminocarbonyl, N—($C_3$–$C_6$-alkenyl)-N-($C_{1-6}$-alkyl)aminocarbonyl, N—($C_1$–$C_6$-alkoxy)-N-($C_1$–$C_6$-alkyl) aminocarbonyl, N—($C_3$–$C_6$-alkenyl)-N-($C_1$–$C_6$-alkoxy) aminocarbonyl, di-($C_1$–$C_6$-alkyl) aminothiocarbonyl or abovementioned alkyl, cycloalkyl and alkoxy radicals may be partially or fully halogenated and/or may carry one to three of the following groups: cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;
phenyl, heterocyclyl, phenyl-$C_1$–$C_6$-alkyl, heterocyclyl-$C_1$–$C_6$-alkyl, phenylcarbonyl-$C_1$–$C_6$-alkyl, heterocyclylcarbonyl-$C_1$–$C_6$-alkyl, phenylcarbonyl, heterocyclylcarbonyl, phenoxycarbonyl, heterocyclyloxycarbonyl, phenoxythiocarbonyl, heterocyclyloxythiocarbonyl, phenoxy-$C_1$–$C_6$-alkylcarbonyl or heterocyclyloxy-$C_1$–$C_6$-alkylcarbonyl, where the phenyl and the heterocyclyl radical of the 14 last-mentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^8$ is $C_1$–$C_6$-alkyl, $C_3$–$C_6$-alkenyl, $C_3$–$C_6$-haloalkenyl, $C_3$–$C_6$-cycloalkyl, hydroxyl, $C_1$–$C_6$-alkoxy, di-$C_1$–$C_6$-alkylamino or di-($C_1$–$C_6$-haloalkyl)amino, where the abovementioned alkyl, cycloalkyl and alkoxy radicals may be partially or fully halogenated and/or may carry one to three of the following groups:
cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;
phenyl, heterocyclyl, phenyl-$C_1$–$C_6$-alkyl, heterocyclyl-$C_1$–$C_6$-alkyl, phenoxy, heterocyclyloxy, where the phenyl and the heterocyclyl radical of the last-mentioned substituents may be partially or fully halogenated and/or may carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^{10}$ is $C_1$–$C_6$-alkyl, $C_3$–$C_6$-alkenyl, $C_3$–$C_6$-haloalkenyl, $C_3$–$C_6$-cycloalkyl, $C_1$–$C_6$-alkoxy, $C_3$–$C_6$-alkenyloxy or di-($C_1$–$C_6$-alkyl)amino, where the abovementioned alkyl, cycloalkyl and alkoxy radicals may be partially or fully halogenated and/or may carry one to three radicals from the following group:

cyano, $C_1$–$C_4$-alkoxy, $C_1$–$C_4$-alkylthio, $C_1$–$C_4$-alkylcarbonyl, $C_1$–$C_4$-alkoxycarbonyl, hydroxycarbonyl, di-($C_1$–$C_4$-alkyl)aminocarbonyl, $C_1$–$C_4$-alkylcarbonyloxy or $C_3$–$C_6$-cycloalkyl;

phenyl, heterocyclyl, phenyl-$C_1$–$C_6$-alkyl or heterocyclyl-$C_1$–$C_6$-alkyl, where the phenyl or heterocyclyl radical of the four last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{11}$, $R^{12}$ are $C_1$–$C_6$-alkyl or $C_3$–$C_6$-alkenyl; is 0 to 6.

Particular preference is also given to the compounds of the formula I where the variables have the following meaning, on their own or in combination:

$R^1$ is halogen, $C_1$–$C_6$-alkyl, $C_1$–$C_6$-haloalkyl, $C_1$–$C_6$-alkoxy, $C_1$–$C_6$-alkylthio, heterocyclyloxy or phenylthio, where the two last-mentioned radicals may be partially or fully halogenated and/or may carry one to three of the substituents mentioned below:

nitro, cyano, $C_1$–$C_4$-alkyl, $C_1$–$C_4$-haloalkyl, $C_1$–$C_4$-alkoxy or $C_1$–$C_4$-haloalkoxy; particularly preferably halogen, $C_1$–$C_6$-alkyl or $C_1$–$C_6$-alkylthio;

$R^2$ is hydrogen, $C_1$–$C_6$-alkyl or $C_1$–$C_6$-haloalkyl; particularly preferably hydrogen;

$R^3$ is hydrogen;

$R^5$ is halogen, $OR^7$, $SR^7$, $SOR^8$, $SO_2R^8$, $OSO_2R^8$, $OPR^8R^9$, $OPOR^8R^9$, $OPSR^8R^9$, $NR^{10}R^{11}$ or N-bonded heterocyclyl which may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

particularly preferably halogen, $OR^7$, $NR^{10}R^{11}$ or N-bonded heterocyclyl which may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

particularly preferably fluorine, $OR^7$, $NR^{10}R^{11}$ or N-bonded heterocyclyl selected from the group consisting of 4-morpholinyl or 4-oxo-1,4-dihydropyrid-1-yl;

$R^6$ is $C_1$–$C_6$-alkyl or two radicals $R^6$ which are attached to the same carbon form, together with this carbon, a carbonyl group;

$R^7$ is $C_1$–$C_6$-alkyl, $C_1$–$C_{20}$-alkylcarbonyl, $C_1$–$C_6$-alkoxycarbonyl, ($C_1$–$C_{20}$-alkylthio)carbonyl, N,N-di-($C_1$–$C_6$-alkyl)aminocarbonyl, phenyl, phenylcarbonyl or phenoxy-$C_1$–$C_6$-alkylcarbonyl, where the phenyl radical of the three last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy; particularly preferably $C_1$–$C_6$-alkyl, $C_1$–$C_{20}$-alkylcarbonyl, $C_1$–$C_6$-alkoxycarbonyl, ($C_1$–$C_6$-alkylthio)carbonyl, N,N-di-($C_1$–$C_6$-alkyl)aminocarbonyl, phenyl, phenylcarbonyl or phenoxy-$C_1$–$C_6$-alkylcarbonyl, where the phenyl radical of the three last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy; particularly preferably $C_1$–$C_{20}$-alkylthiocarbonyl; most preferably $C_1$–$C_6$-alkylthiocarbonyl;

$R^8$, $R^9$ are $C_1$–$C_6$-alkyl, $C_1$–$C_6$-alkoxy, di-($C_1$–$C_6$-alkyl)amino or phenyl, where the last-mentioned radical may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{10}$ is $C_1$–$C_6$-alkyl or $C_1$–$C_6$-alkoxy;

$R^{11}$ is $C_1$–$C_6$-alkyl;

l is from 0 to 6; particularly preferably from 4 to 6; in particular 6.

Particular preference is also given to compounds of the formula I where $R^6$ is nitro, halogen, cyano, $C_1$–$C_6$-alkyl, $C_1$–$C_6$-haloalkyl, di-($C_1$–$C_6$-alkoxy)methyl, di-($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkoxycarbonyloxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl;

or two radicals $R^6$, which are linked to the same carbon, together form an —O—$(CH_2)_m$—O—, —O—$(CH_2)_m$—O—, —O—$(CH_2)_m$—S—, —S—$(CH_2)_m$—S—, —O—$(CH_2)_n$— or —S—$(CH_2)_n$— chain which may be substituted by one to three radicals from the following group:

halogen, cyano, $C_1$–$C_4$-alkyl, $C_1$–$C_4$-haloalkyl or $C_1$–$C_4$-alkoxycarbonyl;

or two radicals $R^6$, which are linked to the same carbon, form a —$(CH_2)_p$ chain which may be interrupted by oxygen or sulfur and/or which may be substituted by one to four radicals from the following group:

halogen, cyano, $C_1$–$C_4$-alkyl, $C_1$–$C_4$-haloalkyl or $C_1$–$C_4$-alkoxycarbonyl;

or two radicals $R^6$, which are linked to the same carbon, together with this carbon form a carbonyl group.

Particular preference is given to compounds of the formula I here $R^6$ is nitro, halogen, cyano, $C_1$–$C_6$-alkyl, $C_1$–$C_6$-haloalkyl, di-($C_1$–$C_6$-alkoxy)methyl, di-($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkoxycarbonyloxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl;

or two radicals $R^6$, which are linked to the same carbon, together with this carbon form a carbonyl group.

Particular preference is also given to the compounds of the formula I where $R^5$ is halogen or ($C_1$–$C_{20}$-alkylthio)carbonyloxy; particularly preferably fluorine or ($C_1$–$C_6$-alkylthio)carbonyloxy;

Particular preference is also given to the compounds of the formula I where $R^5$ is $NR^{10}R^{11}$ or N-linked heterocyclyl which may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

Particular preference is also given to the compounds of the formula I where $R^4$ has the following meanings:
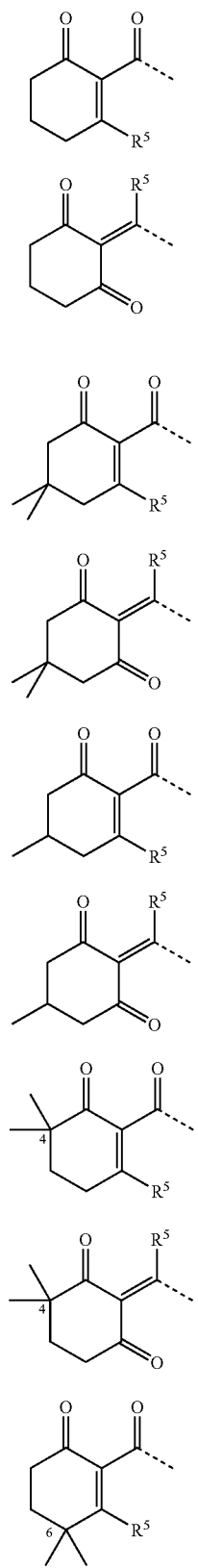
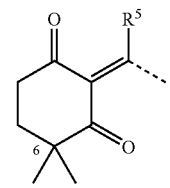

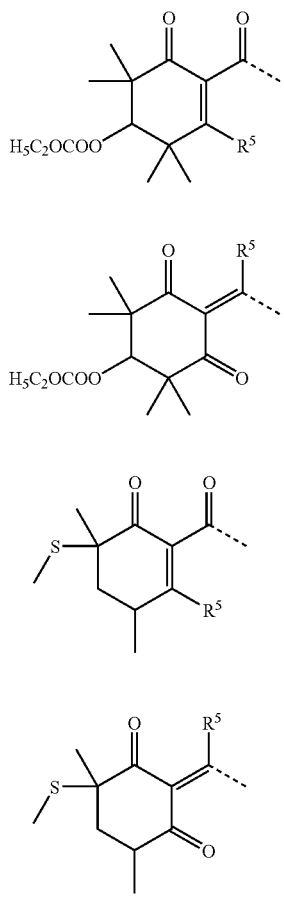

Very particular preference is given to the compounds of the formula I where

R⁵ is NR¹⁰R¹¹ or tetrahydropyrrol-1-yl, 2,3-dihydro-1H-pyrrol-1-yl, 2,5-dihydro-1H-pyrrol-1-yl, pyrrol-1-yl, tetrahydropyrazol-1-yl, tetrahydroisoxazol-2-yl, tetrahydrothiazol-2-yl, tetrahydroimidazol-1-yl, tetrahydrooxazol-3-yl, tetrahydrothiazol-3-yl, pyrazol-1-yl, imidazol-1-yl, 1,2,4-triazol-1-yl, tetrazol-1-yl, piperidin-1-yl, 4-oxo-1,4-dihydro-1-pyridyl, hexahydropyrimidin-1-yl, hexahydropyrazin-1-yl, tetrahydro-1,4-oxazin-4-yl, tetrahydro-1,2-oxazin-2-yl, succinimide, maleimide or glutarimide, where the abovementioned heterocycles may be partially or fully halogenated and/or may carry one to three of the following radicals:

nitro, cyano, $C_1$–$C_4$-alkyl, such as methyl or ethyl, $C_1$–$C_4$-haloalkyl such as chloromethyl, difluoromethyl or trifluoromethyl, $C_1$–$C_4$-alkoxy, such as methoxy or ethoxy or $C_1$–$C_4$-haloalkoxy such as difluoromethoxy or trifluoromethoxy;

$R^{10}$ $C_1$–$C_6$-alkoxy

Extraordinary preference is given to compounds of the formula Ia1 and Ib1 (≡I where l=0), in particular to the compounds Ia1.1 to Ia1.456 and the compounds Ib1.1 to Ib1.456, where the radical definitions $R^1$ to $R^5$ and l have a preferred meaning for the compounds according to the invention not only in combination with each other, but in each case also on their own.

TABLE 1

| No. | $R^1$ | $R^2$ | $R^3$ | $R^5$ |
|---|---|---|---|---|
| Ia1.1 or Ib1.1 | CH₃ | H | H | F |
| Ia1.2 or Ib1.2 | CH₃ | H | H | Cl |
| Ia1.3 or Ib1.3 | CH₃ | H | H | Br |
| Ia1.4 or Ib1.4 | CH₃ | H | H | I |
| Ia1.5 or Ib1.5 | CH₃ | H | H | SCH₃ |
| Ia1.6 or Ib1.6 | CH₃ | H | H | SCH₂CH₃ |
| Ia1.7 or Ib1.7 | CH₃ | H | H | SCO(N(CH₃)₂)₂ |
| Ia1.8 or Ib1.8 | CH₃ | H | H | SO₂CH₃ |
| Ia1.9 or Ib1.9 | CH₃ | H | H | SO₂CH₂CH₃ |
| Ia1.10 or Ib1.10 | CH₃ | H | H | SC₆H₅ |
| Ia1.11 or Ib1.11 | CH₃ | H | H | S(4-CH₃—C₆H₄) |
| Ia1.12 or Ib1.12 | CH₃ | H | H | S(4-Cl—C₆H₄) |
| Ia1.13 or Ib1.13 | CH₃ | H | H | SO₂C₆H₅ |
| Ia1.14 or Ib1.14 | CH₃ | H | H | SO₂(4-CH₃—C₆H₄) |
| Ia1.15 or Ib1.15 | CH₃ | H | H | SO₂(4-Cl—C₆H₄) |
| Ia1.16 or Ib1.16 | CH₃ | H | H | 4-morpholinyl |
| Ia1.17 or Ib1.17 | CH₃ | H | H | 1-pyrrolidinyl |
| Ia1.18 or Ib1.18 | CH₃ | H | H | 1-(1,2,4-triazolyl) |
| Ia1.19 or Ib1.19 | CH₃ | H | H | 1-imidazolyl |
| Ia1.20 or Ib1.20 | CH₃ | H | H | 1-pyrazolyl |
| Ia1.21 or Ib1.21 | CH₃ | H | H | 4-oxo-1,4-dihydro-1-pyridyl |
| Ia1.22 or Ib1.22 | CH₃ | H | H | N(OCH₃)CH₃ |
| Ia1.23 or Ib1.23 | CH₃ | H | H | 2-tetrahydroisoxazolyl |
| Ia1.24 or Ib1.24 | CH₃ | H | H | N(CH₃)N(CH₃)₂ |
| Ia1.25 or Ib1.25 | CH₃ | H | H | N(CH₂CH=CH₂)N(CH₃)₂ |
| Ia1.26 or Ib1.26 | CH₃ | H | H | OPO(OCH₃)₂ |
| Ia1.27 or Ib1.27 | CH₃ | H | H | OPO(OCH₂CH₃)₂ |
| Ia1.28 or Ib1.28 | CH₃ | H | H | OPO(N(CH₃)₂)₂ |
| Ia1.29 or Ib1.29 | CH₃ | H | H | OPO(OC₆H₅)₂ |
| Ia1.30 or Ib1.30 | CH₃ | H | H | OPO(CH₃)₂ |
| Ia1.31 or Ib1.31 | CH₃ | H | H | OPO(CH₂CH₃)₂ |
| Ia1.32 or Ib1.32 | CH₃ | H | H | OPO(C₆H₅)₂ |
| Ia1.33 or Ib1.33 | CH₃ | H | H | OPS(OCH₃)₂ |
| Ia1.34 or Ib1.34 | CH₃ | H | H | OPS(OCH₂CH₃)₂ |
| Ia1.35 or Ib1.35 | CH₃ | H | H | OP(OCH₃)₂ |
| Ia1.36 or Ib1.36 | CH₃ | H | H | OP(OCH₂CH₃)₂ |
| Ia1.37 or Ib1.37 | CH₃ | H | H | PO(OCH₃)₂ |
| Ia1.38 or Ib1.38 | CH₃ | H | H | PO(OCH₂CH₃)₂ |
| Ia1.39 or Ib1.39 | CH₃ | H | H | PO(C₆H₅)₂ |
| Ia1.40 or Ib1.40 | CH₃ | H | H | OCH₃ |
| Ia1.41 or Ib1.41 | CH₃ | H | H | OCH₂CH₃ |
| Ia1.42 or Ib1.42 | CH₃ | H | H | OCH₂C₆H₅ |
| Ia1.43 or Ib1.43 | CH₃ | H | H | OCH₂(2-furyl) |
| Ia1.44 or Ib1.44 | CH₃ | H | H | OCH₂(3-furyl) |
| Ia1.45 or Ib1.45 | CH₃ | H | H | OCOOCH₃ |
| Ia1.46 or Ib1.46 | CH₃ | H | H | OCOOCH₂CH₃ |
| Ia1.47 or Ib1.47 | CH₃ | H | H | OCOOCH(CH₃)₂ |
| Ia1.48 or Ib1.48 | CH₃ | H | H | OCOOC₆H₅ |
| Ia1.49 or Ib1.49 | CH₃ | H | H | OCOOC(CH₃)₃ |
| Ia1.50 or Ib1.50 | CH₃ | H | H | OCSOC₆H₅ |
| Ia1.51 or Ib1.51 | CH₃ | H | H | OCSN(CH₃)₂ |

TABLE 1-continued

Ia1 (structure: cyclohexanone with carbonyl linker to quinoline bearing R1, R2, R3; R5 on cyclohexanone)

Ib1 (structure: cyclohexane-1,3-dione with =C(R5)- linker to quinoline bearing R1, R2, R3)

| No. | R¹ | R² | R³ | R⁵ |
|---|---|---|---|---|
| Ia1.52 or Ib1.52 | CH₃ | H | H | OCON(CH₃)₂ |
| Ia1.53 or Ib1.53 | CH₃ | H | H | OCOSCH₃ |
| Ia1.54 or Ib1.54 | CH₃ | H | H | ON(CH₃)₂ |
| Ia1.55 or Ib1.55 | CH₃ | H | H | O-1-piperidyl |
| Ia1.56 or Ib1.56 | CH₃ | H | H | OCOCH₃ |
| Ia1.57 or Ib1.57 | CH₃ | H | H | OCOCH₂CH₃ |
| Ia1.58 or Ib1.58 | CH₃ | H | H | OCOCH(CH₃)₂ |
| Ia1.59 or Ib1.59 | CH₃ | H | H | OCOC(CH₃)₃ |
| Ia1.60 or Ib1.60 | CH₃ | H | H | OCO(CH₂)₆CH₃ |
| Ia1.61 or Ib1.61 | CH₃ | H | H | OCO(CH₂)₇CH₃ |
| Ia1.62 or Ib1.62 | CH₃ | H | H | OCO(CH₂)₁₆CH₃ |
| Ia1.63 or Ib1.63 | CH₃ | H | H | OCO(CH₂)₁₄CH₃ |
| Ia1.64 or Ib1.64 | CH₃ | H | H | OCOCH₂CH=CH₂ |
| Ia1.65 or Ib1.65 | CH₃ | H | H | OCO(CH₂)₃O(2,4-Cl₂—C₆H₃) |
| Ia1.66 or Ib1.66 | CH₃ | H | H | OCOCH(CH₃)O—(2-CH₃-4-Cl—C₆H₃) |
| Ia1.67 or Ib1.67 | CH₃ | H | H | OCOcyclopropyl |
| Ia1.68 or Ib1.68 | CH₃ | H | H | OCOcyclopentyl |
| Ia1.69 or Ib1.69 | CH₃ | H | H | OCOcyclohexyl |
| Ia1.70 or Ib1.70 | CH₃ | H | H | OCOC₆H₅ |
| Ia1.71 or Ib1.71 | CH₃ | H | H | OCO(2-tetrahydrofuryl) |
| Ia1.72 or Ib1.72 | CH₃ | H | H | OCO(2-furyl) |
| Ia1.73 or Ib1.73 | CH₃ | H | H | OCO(2-thienyl) |
| Ia1.74 or Ib1.74 | CH₃ | H | H | OCO(3-pyridyl) |
| Ia1.75 or Ib1.75 | CH₃ | H | H | OSO₂CH₃ |
| Ia1.76 or Ib1.76 | CH₃ | H | H | OSO₂CH₂CH₃ |
| Ia1.77 or Ib1.77 | F | H | H | F |
| Ia1.78 or Ib1.78 | F | H | H | Cl |
| Ia1.79 or Ib1.79 | F | H | H | Br |
| Ia1.80 or Ib1.80 | F | H | H | I |
| Ia1.81 or Ib1.81 | F | H | H | SCH₃ |
| Ia1.82 or Ib1.82 | F | H | H | SCH₂CH₃ |
| Ia1.83 or Ib1.83 | F | H | H | SCO(N(CH₃)₂)₂ |
| Ia1.84 or Ib1.84 | F | H | H | SO₂CH₃ |
| Ia1.85 or Ib1.85 | F | H | H | SO₂CH₂CH₃ |
| Ia1.86 or Ib1.86 | F | H | H | SC₆H₅ |
| Ia1.87 or Ib1.87 | F | H | H | S(4-CH₃—C₆H₄) |
| Ia1.88 or Ib1.88 | F | H | H | S(4-Cl—C₆H₄) |
| Ia1.89 or Ib1.89 | F | H | H | SO₂C₆H₅ |
| Ia1.90 or Ib1.90 | F | H | H | SO₂(4-CH₃—C₆H₄) |
| Ia1.91 or Ib1.91 | F | H | H | SO₂(4-Cl—C₆H₄) |
| Ia1.92 or Ib1.92 | F | H | H | 4-morpholinyl |
| Ia1.93 or Ib1.93 | F | H | H | 1-pyrrolidinyl |
| Ia1.94 or Ib1.94 | F | H | H | 1-(1,2,4-triazolyl) |
| Ia1.95 or Ib1.95 | F | H | H | 1-imidazolyl |
| Ia1.96 or Ib1.96 | F | H | H | 1-pyrazolyl |
| Ia1.97 or Ib1.97 | F | H | H | 4-oxo-1,4-dihydro-1-pyridyl |
| Ia1.98 or Ib1.98 | F | H | H | N(OCH₃)CH₃ |
| Ia1.99 or Ib1.99 | F | H | H | 2-tetrahydroisoxazolyl |
| Ia1.100 or Ib1.100 | F | H | H | N(CH₃)N(CH₃)₂ |
| Ia1.101 or Ib1.101 | F | H | H | N(CH₂CH=CH₂)N(CH₃)₂ |
| Ia1.102 or Ib1.102 | F | H | H | OPO(OCH₃)₂ |
| Ia1.103 or Ib1.103 | F | H | H | OPO(N(CH₃)₂)₂ |
| Ia1.104 or Ib1.104 | F | H | H | OPO(OCH₂CH₃)₂ |
| Ia1.105 or Ib1.105 | F | H | H | OPO(OC₆H₅)₂ |
| Ia1.106 or Ib1.106 | F | H | H | OPO(CH₃)₂ |
| Ia1.107 or Ib1.107 | F | H | H | OPO(CH₂CH₃)₂ |
| Ia1.108 or Ib1.108 | F | H | H | OPO(C₆H₅)₂ |
| Ia1.109 or Ib1.109 | F | H | H | OPS(OCH₃)₂ |
| Ia1.110 or Ib1.110 | F | H | H | OPS(OCH₂CH₃)₂ |
| Ia1.111 or Ib1.111 | F | H | H | OP(OCH₃)₂ |
| Ia1.112 or Ib1.112 | F | H | H | OP(OCH₂CH₃)₂ |
| Ia1.113 or Ib1.113 | F | H | H | PO(OCH₃)₂ |
| Ia1.114 or Ib1.114 | F | H | H | PO(OCH₂CH₃)₂ |
| Ia1.115 or Ib1.115 | F | H | H | PO(C₆H₅)₂ |
| Ia1.116 or Ib1.116 | F | H | H | OCH₃ |
| Ia1.117 or Ib1.117 | F | H | H | OCH₂CH₃ |
| Ia1.118 or Ib1.118 | F | H | H | OCH₂C₆H₅ |
| Ia1.119 or Ib1.119 | F | H | H | OCH₂(2-furyl) |
| Ia1.120 or Ib1.120 | F | H | H | OCH₂(3-furyl) |
| Ia1.121 or Ib1.121 | F | H | H | OCOOCH₃ |
| Ia1.122 or Ib1.122 | F | H | H | OCOOCH₂CH₃ |
| Ia1.123 or Ib1.123 | F | H | H | OCOOCH(CH₃)₂ |
| Ia1.124 or Ib1.124 | F | H | H | OCOOC₆H₅ |
| Ia1.125 or Ib1.125 | F | H | H | OCOOC(CH₃)₃ |
| Ia1.126 or Ib1.126 | F | H | H | OCSOC₆H₅ |
| Ia1.127 or Ib1.127 | F | H | H | OCSN(CH₃)₂ |
| Ia1.128 or Ib1.128 | F | H | H | OCON(CH₃)₂ |
| Ia1.129 or Ib1.129 | F | H | H | OCOSCH₃ |
| Ia1.130 or Ib1.130 | F | H | H | ON(CH₃)₂ |
| Ia1.131 or Ib1.131 | F | H | H | O-1-piperidyl |
| Ia1.132 or Ib1.132 | F | H | H | OCOCH₃ |
| Ia1.133 or Ib1.133 | F | H | H | OCOCH₂CH₃ |
| Ia1.134 or Ib1.134 | F | H | H | OCOCH(CH₃)₂ |
| Ia1.135 or Ib1.135 | F | H | H | OCOC(CH₃)₃ |
| Ia1.136 or Ib1.136 | F | H | H | OCO(CH₂)₆CH₃ |
| Ia1.137 or Ib1.137 | F | H | H | OCO(CH₂)₇CH₃ |
| Ia1.138 or Ib1.138 | F | H | H | OCO(CH₂)₁₆CH₃ |
| Ia1.139 or Ib1.139 | F | H | H | OCO(CH₂)₁₄CH₃ |
| Ia1.140 or Ib1.140 | F | H | H | OCOCH₂CH=CH₂ |
| Ia1.141 or Ib1.141 | F | H | H | OCO(CH₂)₃O(2,4-Cl₂—C₆H₃) |
| Ia1.142 or Ib1.142 | F | H | H | OCOCH(CH₃)O—(2-CH₃-4-Cl—C₆H₃) |
| Ia1.143 or Ib1.143 | F | H | H | OCOcyclopropyl |
| Ia1.144 or Ib1.144 | F | H | H | OCOcyclopentyl |
| Ia1.145 or Ib1.145 | F | H | H | OCOcyclohexyl |
| Ia1.146 or Ib1.146 | F | H | H | OCOC₆H₅ |
| Ia1.147 or Ib1.147 | F | H | H | OCO(2-tetrahydrofuryl) |
| Ia1.148 or Ib1.148 | F | H | H | OCO(2-furyl) |
| Ia1.149 or Ib1.149 | F | H | H | OCO(2-thienyl) |
| Ia1.150 or Ib1.150 | F | H | H | OCO(3-pyridyl) |
| Ia1.151 or Ib1.151 | F | H | H | OSO₂CH₃ |
| Ia1.152 or Ib1.152 | F | H | H | OSO₂CH₂CH₃ |

TABLE 1-continued

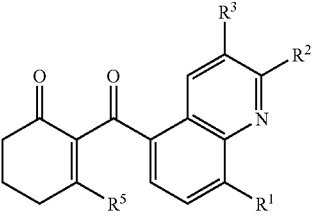

Ia1

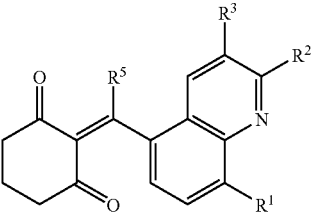

Ib1

| No. | R¹ | R² | R³ | R⁵ |
|---|---|---|---|---|
| Ia1.153 or Ib1.153 | CF₃ | H | H | F |
| Ia1.154 or Ib1.154 | CF₃ | H | H | Cl |
| Ia1.155 or Ib1.155 | CF₃ | H | H | Br |
| Ia1.156 or Ib1.156 | CF₃ | H | H | I |
| Ia1.157 or Ib1.157 | CF₃ | H | H | SCH₃ |
| Ia1.158 or Ib1.158 | CF₃ | H | H | SCH₂CH₃ |
| Ia1.159 or Ib1.159 | CF₃ | H | H | SCO(N(CH₃)₂)₂ |
| Ia1.160 or Ib1.160 | CF₃ | H | H | SO₂CH₃ |
| Ia1.161 or Ib1.161 | CF₃ | H | H | SO₂CH₂CH₃ |
| Ia1.162 or Ib1.162 | CF₃ | H | H | SC₆H₅ |
| Ia1.163 or Ib1.163 | CF₃ | H | H | S(4-CH₃—C₆H₄) |
| Ia1.164 or Ib1.164 | CF₃ | H | H | S(4-Cl—C₆H₄) |
| Ia1.165 or Ib1.165 | CF₃ | H | H | SO₂C₆H₅ |
| Ia1.166 or Ib1.166 | CF₃ | H | H | SO₂(4-CH₃—C₆H₄) |
| Ia1.167 or Ib1.167 | CF₃ | H | H | SO₂(4-Cl—C₆H₄) |
| Ia1.168 or Ib1.168 | CF₃ | H | H | 4-morpholinyl |
| Ia1.169 or Ib1.169 | CF₃ | H | H | 1-pyrrolidinyl |
| Ia1.170 or Ib1.170 | CF₃ | H | H | 1-(1,2,4-triazolyl) |
| Ia1.171 or Ib1.171 | CF₃ | H | H | 1-imidazolyl |
| Ia1.172 or Ib1.172 | CF₃ | H | H | 1-pyrazolyl |
| Ia1.173 or Ib1.173 | CF₃ | H | H | 4-oxo-1,4-dihydro-1-pyridyl |
| Ia1.174 or Ib1.174 | CF₃ | H | H | N(OCH₃)CH₃ |
| Ia1.175 or Ib1.175 | CF₃ | H | H | 2-tetrahydroisoxazolyl |
| Ia1.176 or Ib1.176 | CF₃ | H | H | N(CH₃)N(CH₃)₂ |
| Ia1.177 or Ib1.177 | CF₃ | H | H | N(CH₂CHCH₂)N(CH₃)₂ |
| Ia1.178 or Ib1.178 | CF₃ | H | H | OPO(OCH₃)₂ |
| Ia1.179 or Ib1.179 | CF₃ | H | H | OPO(OCH₂CH₃)₂ |
| Ia1.180 or Ib1.180 | CF₃ | H | H | OPO(N(CH₃)₂)₂ |
| Ia1.181 or Ib1.181 | CF₃ | H | H | OPO(OC₆H₅)₂ |
| Ia1.182 or Ib1.182 | CF₃ | H | H | OPO(CH₃)₂ |
| Ia1.183 or Ib1.183 | CF₃ | H | H | OPO(CH₂CH₃)₂ |
| Ia1.184 or Ib1.184 | CF₃ | H | H | OPO(C₆H₅)₂ |
| Ia1.185 or Ib1.185 | CF₃ | H | H | OPS(OCH₃)₂ |
| Ia1.186 or Ib1.186 | CF₃ | H | H | OPS(OCH₂CH₃)₂ |
| Ia1.187 or Ib1.187 | CF₃ | H | H | OP(OCH₃)₂ |
| Ia1.188 or Ib1.188 | CF₃ | H | H | OP(OCH₂CH₃)₂ |
| Ia1.189 or Ib1.189 | CF₃ | H | H | PO(OCH₃)₂ |
| Ia1.190 or Ib1.190 | CF₃ | H | H | PO(OCH₂CH₃)₂ |
| Ia1.191 or Ib1.191 | CF₃ | H | H | PO(C₆H₅)₂ |
| Ia1.192 or Ib1.192 | CF₃ | H | H | OCH₃ |
| Ia1.193 or Ib1.193 | CF₃ | H | H | OCH₂CH₃ |
| Ia1.194 or Ib1.194 | CF₃ | H | H | OCH₂C₆H₅ |
| Ia1.195 or Ib1.195 | CF₃ | H | H | OCH₂(2-furyl) |
| Ia1.196 or Ib1.196 | CF₃ | H | H | OCH₂(3-furyl) |
| Ia1.197 or Ib1.197 | CF₃ | H | H | OCOOCH₃ |
| Ia1.198 or Ib1.198 | CF₃ | H | H | OCOOCH₂CH₃ |
| Ia1.199 or Ib1.199 | CF₃ | H | H | OCOOCH(CH₃)₂ |
| Ia1.200 or Ib1.200 | CF₃ | H | H | OCOOC₆H₅ |
| Ia1.201 or Ib1.201 | CF₃ | H | H | OCOOC(CH₃)₃ |
| Ia1.202 or Ib1.202 | CF₃ | H | H | OCSOC₆H₅ |
| Ia1.203 or Ib1.203 | CF₃ | H | H | OCSN(CH₃)₂ |
| Ia1.204 or Ib1.204 | CF₃ | H | H | OCON(CH₃)₂ |
| Ia1.205 or Ib1.205 | CF₃ | H | H | OCOSCH₃ |
| Ia1.206 or Ib1.206 | CF₃ | H | H | ON(CH₃)₂ |
| Ia1.207 or Ib1.207 | CF₃ | H | H | O-1-piperidyl |
| Ia1.208 or Ib1.208 | CF₃ | H | H | OCOCH₃ |
| Ia1.209 or Ib1.209 | CF₃ | H | H | OCOCH₂CH₃ |
| Ia1.210 or Ib1.210 | CF₃ | H | H | OCOCHC(CH₃)₂ |
| Ia1.211 or Ib1.211 | CF₃ | H | H | OCOC(CH₃)₃ |
| Ia1.212 or Ib1.212 | CF₃ | H | H | OCO(CH₂)₆CH₃ |
| Ia1.213 or Ib1.213 | CF₃ | H | H | OCO(CH₂)₇CH₃ |
| Ia1.214 or Ib1.214 | CF₃ | H | H | OCO(CH₂)₁₆CH₃ |
| Ia1.215 or Ib1.215 | CF₃ | H | H | OCO(CH₂)₁₄CH₃ |
| Ia1.216 or Ib1.216 | CF₃ | H | H | OCOCH₂CH=CH₂ |
| Ia1.217 or Ib1.217 | CF₃ | H | H | OCO(CH₂)₃O(2,4-Cl₂—C₆H₃) |
| Ia1.218 or Ib1.218 | CF₃ | H | H | OCOCH(CH₃)O—(2-CH₃-4-Cl—C₆H₃) |
| Ia1.219 or Ib1.219 | CF₃ | H | H | OCOcyclopropyl |
| Ia1.220 or Ib1.220 | CF₃ | H | H | OCOcyclopentyl |
| Ia1.221 or Ib1.221 | CF₃ | H | H | OCOcyclohexyl |
| Ia1.222 or Ib1.222 | CF₃ | H | H | OCOC₆H₅ |
| Ia1.223 or Ib1.223 | CF₃ | H | H | OCO(2-tetrahydrofuryl) |
| Ia1.224 or Ib1.224 | CF₃ | H | H | OCO(2-furyl) |
| Ia1.225 or Ib1.225 | CF₃ | H | H | OCO(2-thienyl) |
| Ia1.226 or Ib1.226 | CF₃ | H | H | OCO(3-pyridyl) |
| Ia1.227 or Ib1.227 | CF₃ | H | H | OSO₂CH₃ |
| Ia1.228 or Ib1.228 | CF₃ | H | H | OSO₂CH₂CH₃ |
| Ia1.229 or Ib1.229 | Cl | H | H | F |
| Ia1.230 or Ib1.230 | Cl | H | H | Cl |
| Ia1.231 or Ib1.231 | Cl | H | H | Br |
| Ia1.232 or Ib1.232 | Cl | H | H | I |
| Ia1.233 or Ib1.233 | Cl | H | H | SCH₃ |
| Ia1.234 or Ib1.234 | Cl | H | H | SCH₂CH₃ |
| Ia1.235 or Ib1.235 | Cl | H | H | SCO(N(CH₃)₂)₂ |
| Ia1.236 or Ib1.236 | Cl | H | H | SO₂CH₃ |
| Ia1.237 or Ib1.237 | Cl | H | H | SO₂CH₂CH₃ |
| Ia1.238 or Ib1.238 | Cl | H | H | SC₆H₅ |
| Ia1.239 or Ib1.239 | Cl | H | H | S(4-CH₃—C₆H₄) |
| Ia1.240 or Ib1.240 | Cl | H | H | S(4-Cl—C₆H₄) |
| Ia1.241 or Ib1.241 | Cl | H | H | SO₂C₆H₅ |
| Ia1.242 or Ib1.242 | Cl | H | H | SO₂(4-CH₃—C₆H₄) |
| Ia1.243 or Ib1.243 | Cl | H | H | SO₂(4-Cl—C₆H₄) |
| Ia1.244 or Ib1.244 | Cl | H | H | 4-morpholinyl |
| Ia1.245 or Ib1.245 | Cl | H | H | 1-pyrrolidinyl |
| Ia1.246 or Ib1.246 | Cl | H | H | 1-(1,2,4-triazolyl) |
| Ia1.247 or Ib1.247 | Cl | H | H | 1-imidazolyl |
| Ia1.248 or Ib1.248 | Cl | H | H | 1-pyrazolyl |
| Ia1.249 or Ib1.249 | Cl | H | H | 4-oxo-1,4-dihydro-1-pyridyl |
| Ia1.250 or Ib1.250 | Cl | H | H | N(OCH₃)CH₃ |
| Ia1.251 or Ib1.251 | Cl | H | H | 2-tetrahydroisoxazolyl |
| Ia1.252 or Ib1.252 | Cl | H | H | N(CH₃)N(CH₃)₂ |
| Ia1.253 or Ib1.253 | Cl | H | H | N(CH₂CH=CH₂)N(CH₃)₂ |

TABLE 1-continued

Ia1

[Structure Ia1: cyclohexanone with carbonyl linker to quinoline bearing R², R³, R¹, R⁵ substituents]

Ib1

[Structure Ib1: cyclohexane-1,3-dione with =C(R⁵)– linker to quinoline bearing R², R³, R¹]

| No. | R¹ | R² | R³ | R⁵ |
|---|---|---|---|---|
| Ia1.254 or Ib1.254 | Cl | H | H | OPO(OCH₃)₂ |
| Ia1.255 or Ib1.255 | Cl | H | H | OPO(OCH₂CH₃)₂ |
| Ia1.256 or Ib1.256 | Cl | H | H | OPO(N(CH₃)₂)₂ |
| Ia1.257 or Ib1.257 | Cl | H | H | OPO(OC₆H₅)₂ |
| Ia1.258 or Ib1.258 | Cl | H | H | OPO(CH₃)₂ |
| Ia1.259 or Ib1.259 | Cl | H | H | OPO(CH₂CH₃)₂ |
| Ia1.260 or Ib1.260 | Cl | H | H | OPO(C₆H₅)₂ |
| Ia1.261 or Ib1.261 | Cl | H | H | OPS(OCH₃)₂ |
| Ia1.262 or Ib1.262 | Cl | H | H | OPS(OCH₂CH₃)₂ |
| Ia1.263 or Ib1.263 | Cl | H | H | OP(OCH₃)₂ |
| Ia1.264 or Ib1.264 | Cl | H | H | OP(OCH₂CH₃)₂ |
| Ia1.265 or Ib1.265 | Cl | H | H | PO(OCH₃)₂ |
| Ia1.266 or Ib1.266 | Cl | H | H | PO(OCH₂CH₃)₂ |
| Ia1.267 or Ib1.267 | Cl | H | H | PO(C₆H₅)₂ |
| Ia1.268 or Ib1.268 | Cl | H | H | OCH₃ |
| Ia1.269 or Ib1.269 | Cl | H | H | OCH₂CH₃ |
| Ia1.270 or Ib1.270 | Cl | H | H | OCH₂C₆H₅ |
| Ia1.271 or Ib1.271 | Cl | H | H | OCH₂(2-furyl) |
| Ia1.272 or Ib1.272 | Cl | H | H | OCH₂(3-furyl) |
| Ia1.273 or Ib1.273 | Cl | H | H | OCOOCH₃ |
| Ia1.274 or Ib1.274 | Cl | H | H | OCOOCH₂CH₃ |
| Ia1.275 or Ib1.275 | Cl | H | H | OCOOCH(CH₃)₂ |
| Ia1.276 or Ib1.276 | Cl | H | H | OCOOC₆H₅ |
| Ia1.277 or Ib1.277 | Cl | H | H | OCOOC(CH₃)₃ |
| Ia1.278 or Ib1.278 | Cl | H | H | OCSOC₆H₅ |
| Ia1.279 or Ib1.279 | Cl | H | H | OCSN(CH₃)₂ |
| Ia1.280 or Ib1.280 | Cl | H | H | OCON(CH₃)₂ |
| Ia1.281 or Ib1.281 | Cl | H | H | OCOSCH₃ |
| Ia1.282 or Ib1.282 | Cl | H | H | ON(CH₃)₂ |
| Ia1.283 or Ib1.283 | Cl | H | H | O-1-piperidyl |
| Ia1.284 or Ib1.284 | Cl | H | H | OCOCH₃ |
| Ia1.285 or Ib1.285 | Cl | H | H | OCOCH₂CH₃ |
| Ia1.286 or Ib1.286 | Cl | H | H | OCOCH(CH₃)₂ |
| Ia1.287 or Ib1.287 | Cl | H | H | OCOC(CH₃)₃ |
| Ia1.288 or Ib1.288 | Cl | H | H | OCO(CH₂)₆CH₃ |
| Ia1.289 or Ib1.289 | Cl | H | H | OCO(CH₂)₇CH₃ |
| Ia1.290 or Ib1.290 | Cl | H | H | OCO(CH₂)₁₆CH₃ |
| Ia1.291 or Ib1.291 | Cl | H | H | OCO(CH₂)₁₄CH₃ |
| Ia1.292 or Ib1.292 | Cl | H | H | OCOCH₂CH₂CH=CH₂ |
| Ia1.293 or Ib1.293 | Cl | H | H | OCO(CH₂)₃O(2,4-Cl₂—C₆H₃) |
| Ia1.294 or Ib1.294 | Cl | H | H | OCOCH(CH₃)O—(2-CH₃-4-Cl—C₆H₃) |
| Ia1.295 or Ib1.295 | Cl | H | H | OCOcyclopropyl |
| Ia1.296 or Ib1.296 | Cl | H | H | OCOcyclopentyl |
| Ia1.297 or Ib1.297 | Cl | H | H | OCOcyclohexyl |
| Ia1.298 or Ib1.298 | Cl | H | H | OCOC₆H₅ |
| Ia1.299 or Ib1.299 | Cl | H | H | OCO(2-tetrahydrofuryl) |
| Ia1.300 or Ib1.300 | Cl | H | H | OCO(2-furyl) |
| Ia1.301 or Ib1.301 | Cl | H | H | OCO(2-thienyl) |
| Ia1.302 or Ib1.302 | Cl | H | H | OCO(3-pyridyl) |
| Ia1.303 or Ib1.303 | Cl | H | H | OSO₂CH₃ |
| Ia1.304 or Ib1.304 | Cl | H | H | OSO₂CH₂CH₃ |
| Ia1.305 or Ib1.305 | CHF₂ | H | H | F |
| Ia1.306 or Ib1.306 | CHF₂ | H | H | Cl |
| Ia1.307 or Ib1.307 | CHF₂ | H | H | Br |
| Ia1.308 or Ib1.308 | CHF₂ | H | H | I |
| Ia1.309 or Ib1.309 | CHF₂ | H | H | SCH₃ |
| Ia1.310 or Ib1.310 | CHF₂ | H | H | SCH₂CH₃ |
| Ia1.311 or Ib1.311 | CHF₂ | H | H | SCO(N(CH₃)₂) |
| Ia1.312 or Ib1.312 | CHF₂ | H | H | SO₂CH₃ |
| Ia1.313 or Ib1.313 | CHF₂ | H | H | SO₂CH₂CH₃ |
| Ia1.314 or Ib1.314 | CHF₂ | H | H | SC₆H₅ |
| Ia1.315 or Ib1.315 | CHF₂ | H | H | S(4-CH₃—C₆H₄) |
| Ia1.316 or Ib1.316 | CHF₂ | H | H | S(4-Cl—C₆H₄) |
| Ia1.317 or Ib1.317 | CHF₂ | H | H | SO₂C₆H₅ |
| Ia1.318 or Ib1.318 | CHF₂ | H | H | SO₂(4-CH₃—C₆H₄) |
| Ia1.319 or Ib1.319 | CHF₂ | H | H | SO₂(4-Cl—C₆H₄) |
| Ia1.320 or Ib1.320 | CHF₂ | H | H | 4-morpholinyl |
| Ia1.321 or Ib1.321 | CHF₂ | H | H | 1-pyrrolidinyl |
| Ia1.322 or Ib1.322 | CHF₂ | H | H | 1-(1,2,4-triazolyl) |
| Ia1.323 or Ib1.323 | CHF₂ | H | H | 1-imidazolyl |
| Ia1.324 or Ib1.324 | CHF₂ | H | H | 1-pyrazolyl |
| Ia1.325 or Ib1.325 | CHF₂ | H | H | 4-oxo-1,4-dihydro-1-pyridyl |
| Ia1.326 or Ib1.326 | CHF₂ | H | H | N(OCH₃)CH₃ |
| Ia1.327 or Ib1.327 | CHF₂ | H | H | 2-tetrahydroisoxazolyl |
| Ia1.328 or Ib1.328 | CHF₂ | H | H | N(CH₃)N(CH₃)₃ |
| Ia1.329 or Ib1.329 | CHF₂ | H | H | N(CH₂CH=CH₂)N(CH₃)₂ |
| Ia1.330 or Ib1.330 | CHF₂ | H | H | OPO(OCH₃)₂ |
| Ia1.331 or Ib1.331 | CHF₂ | H | H | OPO(OCH₂CH₃)₂ |
| Ia1.332 or Ib1.332 | CHF₂ | H | H | OPO(N(CH₃)₂)₂ |
| Ia1.333 or Ib1.333 | CHF₂ | H | H | OPO(OC₆H₅)₂ |
| Ia1.334 or Ib1.334 | CHF₂ | H | H | OPO(CH₃)₂ |
| Ia1.335 or Ib1.335 | CHF₂ | H | H | OPO(CH₂CH₃)₂ |
| Ia1.336 or Ib1.336 | CHF₂ | H | H | OPO(C₆H₅)₂ |
| Ia1.337 or Ib1.337 | CHF₂ | H | H | OPS(OCH₃)₂ |
| Ia1.338 or Ib1.338 | CHF₂ | H | H | OPS(OCH₂CH₃)₂ |
| Ia1.339 or Ib1.339 | CHF₂ | H | H | OP(OCH₃)₂ |
| Ia1.340 or Ib1.340 | CHF₂ | H | H | OP(OCH₂CH₃)₂ |
| Ia1.341 or Ib1.341 | CHF₂ | H | H | PO(OCH₃)₂ |
| Ia1.342 or Ib1.342 | CHF₂ | H | H | PO(OCH₂CH₃)₂ |
| Ia1.343 or Ib1.343 | CHF₂ | H | H | PO(C₆H₅)₂ |
| Ia1.344 or Ib1.344 | CHF₂ | H | H | OCH₃ |
| Ia1.345 or Ib1.345 | CHF₂ | H | H | OCH₂CH₃ |
| Ia1.346 or Ib1.346 | CHF₂ | H | H | OCH₂C₆H₅ |
| Ia1.347 or Ib1.347 | CHF₂ | H | H | OCH₂(2-furyl) |
| Ia1.348 or Ib1.348 | CHF₂ | H | H | OCH₂(3-furyl) |
| Ia1.349 or Ib1.349 | CHF₂ | H | H | OCOOCH₃ |
| Ia1.350 or Ib1.350 | CHF₂ | H | H | OCOOCH₂CH₃ |
| Ia1.351 or Ib1.351 | CHF₂ | H | H | OCOOCH(CH₃)₂ |
| Ia1.352 or Ib1.352 | CHF₂ | H | H | OCOOC₆H₅ |
| Ia1.353 or Ib1.353 | CHF₂ | H | H | OCOOC(CH₃)₃ |
| Ia1.354 or Ib1.354 | CHF₂ | H | H | OCSOC₆H₅ |
| Ia1.355 or Ib1.355 | CHF₂ | H | H | OCSN(CH₃)₂ |

TABLE 1-continued

Ia1

[Structure Ia1: cyclohexenone with R5 substituent connected via C=O to quinoline bearing R3, R2, R1 substituents]

Ib1

[Structure Ib1: cyclohexane-1,3-dione with exocyclic =C(R5)– linked to quinoline bearing R3, R2, R1 substituents]

| No. | R¹ | R² | R³ | R⁵ |
|---|---|---|---|---|
| Ia1.356 or Ib1.356 | CHF₂ | H | H | OCON(CH₃)₂ |
| Ia1.357 or Ib1.357 | CHF₂ | H | H | OCOSCH₃ |
| Ia1.358 or Ib1.358 | CHF₂ | H | H | ON(CH₃)₂ |
| Ia1.359 or Ib1.359 | CHF₂ | H | H | O-1-piperidyl |
| Ia1.360 or Ib1.360 | CHF₂ | H | H | OCOCH₃ |
| Ia1.361 or Ib1.361 | CHF₂ | H | H | OCOCH₂CH₃ |
| Ia1.362 or Ib1.362 | CHF₂ | H | H | OCOCH(CH₃)₂ |
| Ia1.363 or Ib1.363 | CHF₂ | H | H | OCOC(CH₃)₃ |
| Ia1.364 or Ib1.364 | CHF₂ | H | H | OCO(CH₂)₆CH₃ |
| Ia1.365 or Ib1.365 | CHF₂ | H | H | OCO(CH₂)₇CH₃ |
| Ia1.366 or Ib1.366 | CHF₂ | H | H | OCO(CH₂)₁₆CH₃ |
| Ia1.367 or Ib1.367 | CHF₂ | H | H | OCO(CH₂)₁₄CH₃ |
| Ia1.368 or Ib1.368 | CHF₂ | H | H | OCOCH₂CH₂CH=CH₂ |
| Ia1.369 or Ib1.369 | CHF₂ | H | H | OCO(CH₂)₃O(2,4-Cl₂—C₆H₃) |
| Ia1.370 or Ib1.370 | CHF₂ | H | H | OCOCH(CH₃)O—(2-CH₃-4-Cl—C₆H₃) |
| Ia1.371 or Ib1.371 | CHF₂ | H | H | OCOcyclopropyl |
| Ia1.372 or Ib1.372 | CHF₂ | H | H | OCOcyclopentyl |
| Ia1.373 or Ib1.373 | CHF₂ | H | H | OCOcyclohexyl |
| Ia1.374 or Ib1.374 | CHF₂ | H | H | OCOC₆H₅ |
| Ia1.375 or Ib1.375 | CHF₂ | H | H | OCO(2-tetrahydrofuryl) |
| Ia1.376 or Ib1.376 | CHF₂ | H | H | OCO(2-furyl) |
| Ia1.377 or Ib1.377 | CHF₂ | H | H | OCO(2-thienyl) |
| Ia1.378 or Ib1.378 | CHF₂ | H | H | OCO(3-pyridyl) |
| Ia1.379 or Ib1.379 | CHF₂ | H | H | OSO₂CH₃ |
| Ia1.380 or Ib1.380 | CHF₂ | H | H | OSO₂CH₂CH₃ |
| Ia1.381 or Ib1.381 | Cl | CH₃ | H | F |
| Ia1.382 or Ib1.382 | Cl | CH₃ | H | Cl |
| Ia1.383 or Ib1.383 | Cl | CH₃ | H | Br |
| Ia1.384 or Ib1.384 | Cl | CH₃ | H | I |
| Ia1.385 or Ib1.385 | Cl | CH₃ | H | SCH₃ |
| Ia1.386 or Ib1.386 | Cl | CH₃ | H | SCH₂CH₃ |
| Ia1.387 or Ib1.387 | Cl | CH₃ | H | SCO(N(CH₃)₂)₂ |
| Ia1.388 or Ib1.388 | Cl | CH₃ | H | SO₂CH₃ |
| Ia1.389 or Ib1.389 | Cl | CH₃ | H | SO₂CH₂CH₃ |
| Ia1.390 or Ib1.390 | Cl | CH₃ | H | SC₆H₅ |
| Ia1.391 or Ib1.391 | Cl | CH₃ | H | S(4-CH₃—C₆H₄) |
| Ia1.392 or Ib1.392 | Cl | CH₃ | H | S(4-Cl—C₆H₄) |
| Ia1.393 or Ib1.393 | Cl | CH₃ | H | SO₂C₆H₅ |
| Ia1.394 or Ib1.394 | Cl | CH₃ | H | SO₂(4-CH₃—C₆H₄) |
| Ia1.395 or Ib1.395 | Cl | CH₃ | H | SO₂(4-Cl—C₆H₄) |
| Ia1.396 or Ib1.396 | Cl | CH₃ | H | 4-morpholinyl |
| Ia1.397 or Ib1.397 | Cl | CH₃ | H | 1-pyrrolidinyl |
| Ia1.398 or Ib1.398 | Cl | CH₃ | H | 1-(1,2,4-triazolyl) |
| Ia1.399 or Ib1.399 | Cl | CH₃ | H | 1-imidazolyl |
| Ia1.400 or Ib1.400 | Cl | CH₃ | H | 1-pyrazolyl |
| Ia1.401 or Ib1.401 | Cl | CH₃ | H | 4-oxo-1,4-dihydro-1-pyridyl |
| Ia1.402 or Ib1.402 | Cl | CH₃ | H | N(OCH₃)CH₃ |
| Ia1.403 or Ib1.403 | Cl | CH₃ | H | 2-tetrahydroisoxazolyl |
| Ia1.404 or Ib1.404 | Cl | CH₃ | H | N(CH₃)N(CH₃)₂ |
| Ia1.405 or Ib1.405 | Cl | CH₃ | H | N(CH₂CH=CH₂)N(CH₃)₂ |
| Ia1.406 or Ib1.406 | Cl | CH₃ | H | OPO(OCH₃)₂ |
| Ia1.407 or Ib1.407 | Cl | CH₃ | H | OPO(OCH₂CH₃)₂ |
| Ia1.408 or Ib1.408 | Cl | CH₃ | H | OPO(N(CH₃)₂)₂ |
| Ia1.409 or Ib1.409 | Cl | CH₃ | H | OPO(OC₆H₅)₂ |
| Ia1.410 or Ib1.410 | Cl | CH₃ | H | OPO(CH₃)₂ |
| Ia1.411 or Ib1.411 | Cl | CH₃ | H | OPO(CH₂CH₃)₂ |
| Ia1.412 or Ib1.412 | Cl | CH₃ | H | OPO(C₆H₅)₂ |
| Ia1.413 or Ib1.413 | Cl | CH₃ | H | OPS(OCH₃)₂ |
| Ia1.414 or Ib1.414 | Cl | CH₃ | H | OPS(OCH₂CH₃)₂ |
| Ia1.415 or Ib1.415 | Cl | CH₃ | H | OP(OCH₃)₂ |
| Ia1.416 or Ib1.416 | Cl | CH₃ | H | OP(OCH₂CH₃)₂ |
| Ia1.417 or Ib1.417 | Cl | CH₃ | H | PO(OCH₃)₂ |
| Ia1.418 or Ib1.418 | Cl | CH₃ | H | PO(OCH₂CH₃)₂ |
| Ia1.419 or Ib1.419 | Cl | CH₃ | H | PO(C₆H₅)₂ |
| Ia1.420 or Ib1.420 | Cl | CH₃ | H | OCH₃ |
| Ia1.421 or Ib1.421 | Cl | CH₃ | H | OCH₂CH₃ |
| Ia1.422 or Ib1.422 | Cl | CH₃ | H | OCH₂C₆H₅ |
| Ia1.423 or Ib1.423 | Cl | CH₃ | H | OCH₂(2-furyl) |
| Ia1.424 or Ib1.424 | Cl | CH₃ | H | OCH₂(3-furyl) |
| Ia1.425 or Ib1.425 | Cl | CH₃ | H | OCOOCH₃ |
| Ia1.426 or Ib1.426 | Cl | CH₃ | H | OCOOCH₂CH₃ |
| Ia1.427 or Ib1.427 | Cl | CH₃ | H | OCOOCH(CH₃)₂ |
| Ia1.428 or Ib1.428 | Cl | CH₃ | H | OCOOC₆H₅ |
| Ia1.429 or Ib1.429 | Cl | CH₃ | H | OCOOC(CH₃)₃ |
| Ia1.430 or Ib1.430 | Cl | CH₃ | H | OCSOC₆H₅ |
| Ia1.431 or Ib1.431 | Cl | CH₃ | H | OCSN(CH₃)₂ |
| Ia1.432 or Ib1.432 | Cl | CH₃ | H | OCON(CH₃)₂ |
| Ia1.433 or Ib1.433 | Cl | CH₃ | H | OCOSCH₃ |
| Ia1.434 or Ib1.434 | Cl | CH₃ | H | ON(CH₃)₂ |
| Ia1.435 or Ib1.435 | Cl | CH₃ | H | O-1-piperidyl |
| Ia1.436 or Ib1.436 | Cl | CH₃ | H | OCOCH₃ |
| Ia1.437 or Ib1.437 | Cl | CH₃ | H | OCOCH₂CH₃ |
| Ia1.438 or Ib1.438 | Cl | CH₃ | H | OCOCH(CH₃)₂ |
| Ia1.439 or Ib1.439 | Cl | CH₃ | H | OCOC(CH₃)₃ |
| Ia1.440 or Ib1.440 | Cl | CH₃ | H | OCO(CH₂)₆CH₃ |
| Ia1.441 or Ib1.441 | Cl | CH₃ | H | OCO(CH₂)₇CH₃ |
| Ia1.442 or Ib1.442 | Cl | CH₃ | H | OCO(CH₂)₁₆CH₃ |
| Ia1.443 or Ib1.443 | Cl | CH₃ | H | OCO(CH₂)₁₄CH₃ |
| Ia1.444 or Ib1.444 | Cl | CH₃ | H | OCOCH₂CH₂CH=CH₂ |
| Ia1.445 or Ib1.445 | Cl | CH₃ | H | OCO(CH₂)₃O(2,4-Cl₂—C₆H₃) |
| Ia1.446 or Ib1.446 | Cl | CH₃ | H | OCOCH(CH₃)O—(2-CH₃-4-Cl—C₆H₃) |
| Ia1.447 or Ib1.447 | Cl | CH₃ | H | OCOcyclopropyl |
| Ia1.448 or Ib1.448 | Cl | CH₃ | H | OCOcyclopentyl |
| Ia1.449 or Ib1.449 | Cl | CH₃ | H | OCOcyclohexyl |
| Ia1.450 or Ib1.450 | Cl | CH₃ | H | OCOC₆H₅ |
| Ia1.451 or Ib1.451 | Cl | CH₃ | H | OCO(2-tetrahydrofuryl) |
| Ia1.452 or Ib1.452 | Cl | CH₃ | H | OCO(2-furyl) |
| Ia1.453 or Ib1.453 | Cl | CH₃ | H | OCO(2-thienyl) |

TABLE 1-continued

Ia1

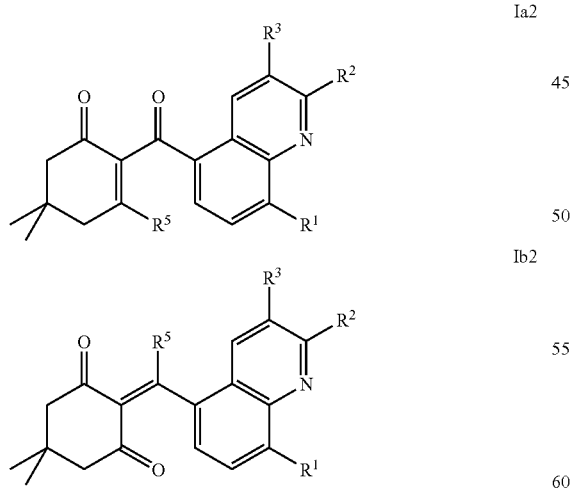

Ib1

| No. | R¹ | R² | R³ | R⁵ |
|---|---|---|---|---|
| Ia1.454 or Ib1.454 | Cl | CH₃ | H | OCO(3-pyridyl) |
| Ia1.455 or Ib1.455 | Cl | CH₃ | H | OSO₂CH₃ |
| Ia1.456 or Ib1.456 | Cl | CH₃ | H | OSO₂CH₂CH₃ |

Extraordinary preference is furthermore given to the following cyclohexenonequinolinoyl derivatives of the formula I:

the compounds of the formulae Ia2 and Ib2, in particular the compounds Ia2.1 to Ia2.456 and the compounds Ib2.1 to Ib2.456, which differ from the compounds Ia1.1 to Ia1.456 and Ib1.1 to Ib1.456, respectively, in that $(R^6)_1$ is "5,5-dimethyl".

Ia2

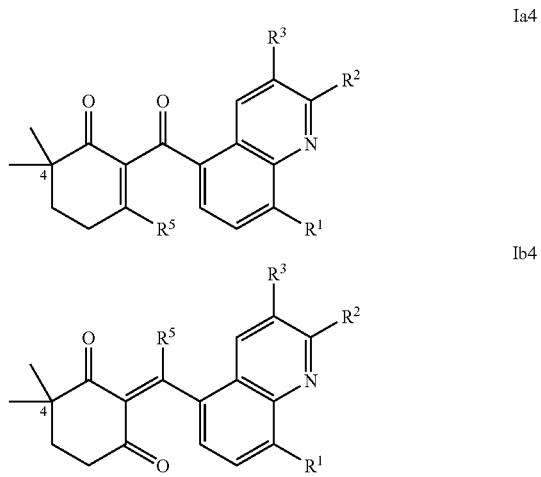

Ib2 the compounds of the formulae Ia3 and Ib3, in particular the compounds Ia3.1 to Ia3.456 and the compounds Ib3.1 to Ib3.456, which differ from the compounds Ia1.1 to Ia1.456 and Ib1.1 to Ib1.456, respectively, in that $(R^6)_1$ is "5-methyl".

Ia3

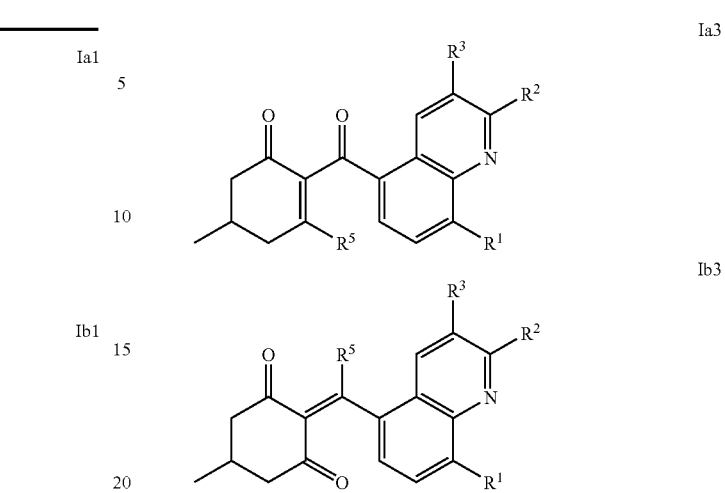

Ib3 the compounds of the formulae Ia4 and Ib4, in particular the compounds Ia4.1 to Ia4.456 and the compounds Ib4.1 to Ib4.456, which differ from the compounds Ia1.1 to Ia1.456 and Ib1.1 to Ib1.456, respectively, in that $(R^6)_1$ is "4,4-dimethyl".

Ia4

Ib4 the compounds of the formulae Ia5 and Ib5, in particular the compounds Ia5.1 to Ia5.456 and the compounds Ib5.1 to Ib5.456, which differ from the compounds Ia1.1 to Ia1.456 and Ib1.1 to Ib1.456, respectively, in that $(R^6)_1$ is "6,6-dimethyl".

Ia5

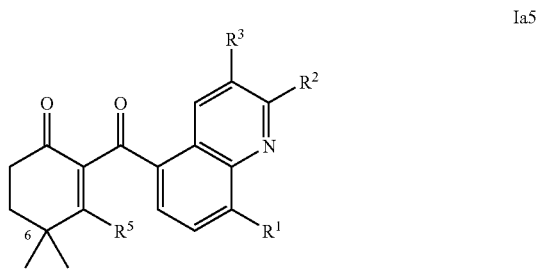

-continued

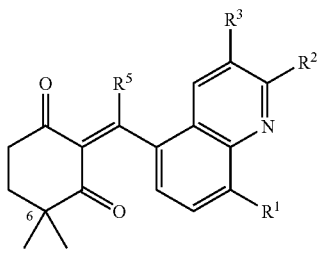
Ib5 the compounds of the formulae Ia6 and Ib6, in particular the compounds Ia6.1 to Ia6.456 and the compounds Ib6.1 to Ib6.456, which differ from the compounds Ia1.1 to Ia1.456 and Ib1.1 to Ib1.456, respectively, in that $(R^6)_1$ is "4,4,6,6-tetramethyl-5-oxo".

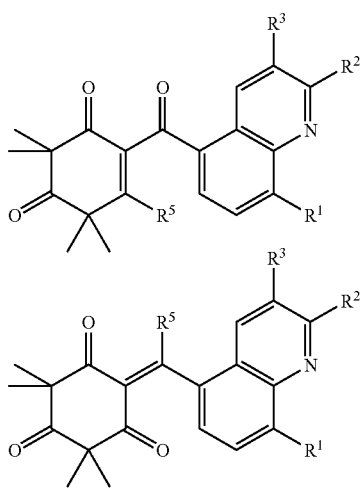
Ia6

Ib6 the compounds of the formulae Ia7 and Ib7, in particular the compounds Ia7.1 to Ia7.456 and the compounds Ib7.1 to Ib7.456, which differ from the compounds Ia1.1 to Ia1.456 and Ib1.1 to Ib1.456, respectively, in that $(R^6)_1$ is "6-methyl".

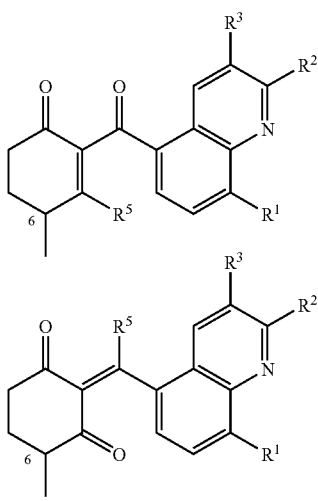
Ia7

Ib7 the compounds of the formulae Ia8 and Ib8, in particular the compounds Ia8.1 to Ia8.456 and the compounds Ib8.1 to Ib8.456, which differ from the compounds Ia1.1 to Ia1.456 and Ib1.1 to Ib1.456, respectively, in that $(R^6)_1$ is "5-hydroxy-4,4,6,6-tetramethyl".

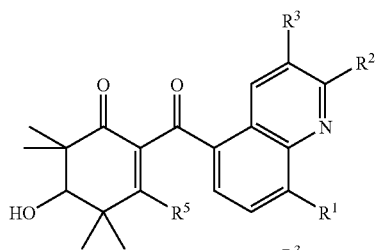
Ia8

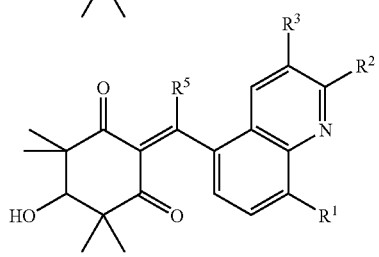
Ib8

The cyclohexenonequinolinoyl derivatives of the formula I can be obtained by various routes, for example by the following processes:

A. Preparation of compounds of the formula I where $R^5$=halogen by reaction of cyclohexanedione derivatives of the formula III with halogenating agents:

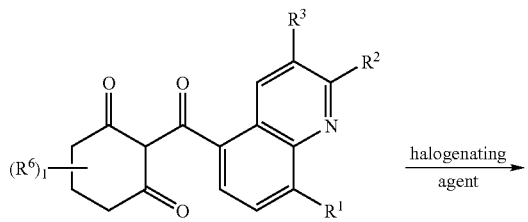

Suitable halogenating agents are, for example, phosgene, diphosgene, triphosgene, thionyl chloride, oxalyl chloride, phosphorus chloride, phosphorus pentachloride, mesyl chloride, chloromethylene-N, N-dimethylammonium chloride, oxalyl bromide, phosphorus oxybromide etc.

B. Preparation of compounds of the formula I where $R^5$=$OR^7$, $OSO_2R^8$, $OPR^8R^9$, $OPSR^8R^9$ or $OPSR^8R^9$ by reaction of cyclohexane dione derivatives of the formula III with alkylating, sulfonylating or phosphonylating agents IVα, IVβ, IVβ, IVδ or IVε.

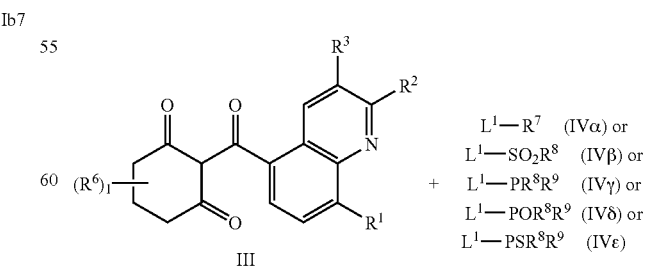

L¹ is a nucleophilically replaceable leaving group, such as halogen, for example chlorine or bromine, hetaryl, for example imidazolyl, carboxylate, for example acetate, or sulfonate, for example mesylate or triflate, etc.

The compounds of the formula IVα, IVβ, IVγ, IVδ or IVε can be employed directly such as, for example, in the case of the carbonyl halides, or generated in situ, for example activated carboxylic acids (using carboxylic acid and dicyclohexyl carbodiimide, etc.).

C. Preparation of compounds of the formula I where $R^5=OR^7$, $SR^7$, $POR^8R^9$, $NR^{10}R^{11}$, $ONR^{11}R^{12}$, N-linked heterocyclyl or O—(N-linked heterocyclyl) by reaction of compounds of the formula I where $R^5$=halogen, $OSO_2R^8$ (Iα) with compounds of the formula Vα, Vβ, Vγ, Vδ, Vε, Vη or Vθ, if appropriate in the presence of a base or with prior formation of salt.

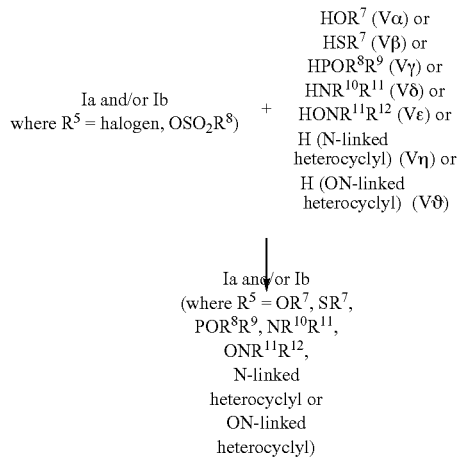

D. Preparation of compounds of the formula I where $R^5=SOR^8$, $SO_2R^8$ by reaction of compounds of the formula I where $R^5=SR^8$ (Iβ) with an oxidizing agent.

Suitable oxidizing agents are, for example, m-chloroperbenzoic acid, peroxy acetic acid, trifluoroperoxy acetic acid, hydrogen peroxide, if appropriate in the presence of a catalyst such as tungstate.

The following conditions apply to the abovementioned reactions: The starting materials are generally employed in equimolar amounts. However, it will also be advantageous to employ an excess of one or the other component.

If appropriate, it may be advantageous to carry out the reactions in the presence of a base. Here, the starting materials and the base are advantageously employed in equimolar amounts. An excess of base, for example 1.5 to 3 molar equivalents, based on Ia and/or Ib (where $R^5$=halogen or $OSO_2R^8$) or III may in certain cases be advantageous.

Suitable bases are tertiary alkyl amines, such as triethylamine, aromatic amines, such as pyridine, alkali metal carbonates, for example sodium carbonate or potassium carbonate, alkali metal bicarbonates, such as sodium bicarbonate and potassium bicarbonate, alkali metal alkoxides, such as sodium methoxide, sodium ethoxide, potassium tert-butoxide or alkali metal hydrides, for example sodium hydride. Preference is given to using triethylamine or pyridine.

Suitable solvents are, for example, chlorinated hydrocarbons, such as methylene chloride or 1,2-dichloroethane, aromatic hydrocarbons, for example toluene, xylene or chlorobenzene, ethers, such as diethyl ether, methyl-tert-butyl ether, tetrahydrofuran or dioxane, polar aprotic solvents, such as acetonitrile, dimethyl formamide or dimethyl sulfoxide, or esters, such as ethyl acetate, or mixtures of these.

The reaction temperature is generally in the range of from 0° C. to the boiling point of the reaction mixture.

Work-up to give the product can be carried out in a manner known per se.

Depending on the reaction conditions, the compounds Ia, Ib or mixtures of these can be formed. The latter can be separated by classical separation methods, such as, for example, crystallization, chromatography, etc.

The cyclohexanedione derivatives of the formula III are known or can be prepared by processes known per se (for example DE-A 19 532 311), for example by reacting cyclohexanones of the formula VI with an activated benzoic acid VIIa or a benzoic acid VIIb, which is preferably activated in situ, to give the acylation product which is subsequently rearranged.

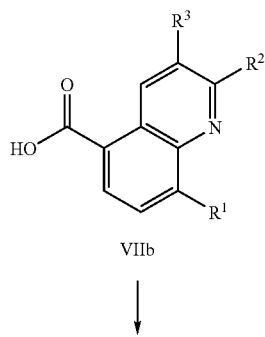

VIIb

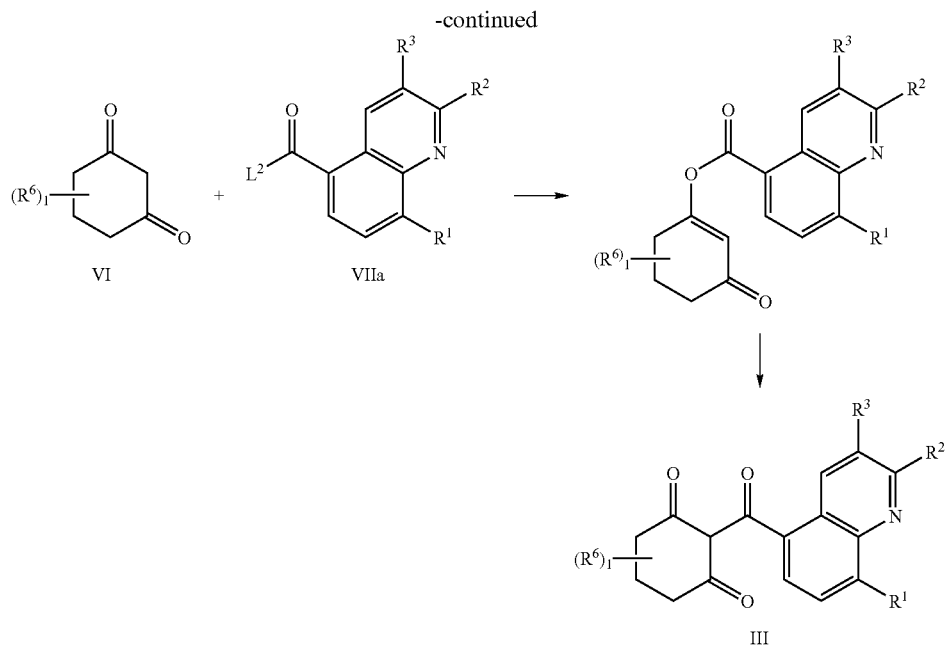

L² is a nucleophilically replaceable leaving group, such as halogen, for example bromine or chlorine, hetaryl, for example imidazolyl or pyridyl, carboxylate, for example acetate or trifluoroacetate, etc.

The activated benzoic acid VIIa can be employed directly, such as in the case of the benzoyl halides, or be generated in situ, for example using dicyclohexyl carbodiimide, triphenylphosphine/azodicarboxylic ester, 2-pyridine disulfide/triphenyl phosphine, carbonyldiimidazole, etc.

If appropriate, it may be advantageous to carry out the acylation reaction in the presence of a base. Here, the starting materials and the auxiliary base are advantageously employed in equimolar amounts. A slight excess of the auxiliary base, for example from 1.2 to 1.5 molar equivalents, based on VII, may be advantageous in certain cases.

Suitable auxiliary bases are tertiary alkyl amines, pyridine or alkali metal carbonates. Suitable solvents are, for example, chlorinated hydrocarbons, such as methylene chloride or 1,2-dichloroethane, aromatic hydrocarbons, such as toluene, xylene or chlorobenzene, ethers, such as diethyl ether, methyl tert-butyl ether, tetrahydrofuran or dioxane, polar aprotic solvents, such as acetonitrile, dimethylformamide or dimethyl sulfoxide, or esters, such as ethyl acetate, or mixtures of these.

If the activated carboxylic acid component employed is a benzoyl halide, it may be advantageous to cool the reaction mixture to 0–10° C. on addition of this reaction partner. The mixture is subsequently stirred at 20–100° C., preferably at 25–50° C., until the reaction is complete. Work-up is carried out in a customary manner, for example the reaction mixture is poured into water and the product of value is extracted. Solvents which are suitable for this purpose are, in particular, methylene chloride, diethyl ether and ethyl acetate. The organic phase is dried and the solvent is removed, after which the crude ester can be employed without any further purification for the rearrangement.

The rearrangement of the esters to the compounds of the formula is advantageously carried out at 20–100° C. in a solvent and in the presence of a base and, if appropriate, with the aid of a cyano compound as catalyst.

Suitable solvents are, for example, acetonitrile, methylene chloride, 1,2-dichloroethane, dioxane, ethyl acetate, toluene or mixtures of these. Preferred solvents are acetonitrile and dioxane.

Suitable bases are tertiary amines, such as triethylamine, aromatic amines, such as pyridine, or alkali metal carbonates, such as sodium carbonate or potassium carbonate, which are preferably employed in an equimolar amount, or up to a four-fold excess, based on the ester. Preference is given to using triethylamine or alkali metal carbonate, preferably in twice the equimolar amount, based on the ester.

Suitable cyano compounds are inorganic cyanides, such as sodium cyanide or potassium cyanide, and organic cyano compounds, such as acetone cyanohydrin or trimethylsilyl cyanide. They are employed in an amount from 1 to 50 mol percent, based on the ester. Preference is given to using acetone cyanohydrin or trimethylsilyl cyanide, for example in an amount from 5 to 15, preferably 10, mol percent, based on the ester.

Work-up can be carried out in a manner known per se. For example, the reaction mixture is acidified with dilute mineral acid, such as 5% strength hydrochloric acid, or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified and the resulting precipitate is filtered off with suction and/or extracted with methylene chloride or ethyl acetate, dried and concentrated.

The benzoyl halides of the formula VIIa (where L²=Cl, Br) can be prepared in a manner known per se by reaction of the benzoic acids of the formula VIIb with halogenating agents, such as thionyl chloride, thionyl bromide, phosgene, diphosgene, triphosgene, oxalyl chloride, oxalyl bromide.

The benzoic acids of the formula VIIb can be prepared in a known manner from the corresponding esters by acidic or basic hydrolysis. The latter are known from the literature or can be prepared in a manner known per se.

8-Difluoromethyl-5-alkoxycarbonyl-quinolines can be obtained from the corresponding 8-aldehyde derivatives by fluorination. A suitable fluorinating agent is, inter alia, DAST. The formyl quinoline is obtained by oxidation of the corresponding bromomethyl quinoline.

Furthermore, it is possible to obtain 8-difluoromethoxy-5-alkoxycarbonyl-quinolines from the corresponding 8-hydroxy derivatives by reaction with chlorodifluoromethane. This reaction is preferably carried out in the presence of a base, such as potassium hydroxide or sodium hydroxide, in an aprotic solvent. The 8-hydroxy-5-alkoxycarbonylquinolines are obtained from 8-hydroxy-5-hydroxycarbonyl-quinoline by esterification reactions which are known per se.

PREPARATION EXAMPLES

2-[(8-Chloroquinolin-5-yl)carbonyl]-1-chloro-4,4,6,6-tetramethyl-cyclohex-1-ene-3,5-dione (Compound 2.22) and 2-[(8-chloroquinolin-5-yl)chloromethylidene]-4,4,6,6-tetramethylcyclohexane-1,3,5-trione (Compound 3.1)

4.0 g (10.8 mmol) of 2-(8-chloroquinolin-5-yl)carbonyl-4,4,6,6-tetramethylcyclohexane-1,3,5-trione were dissolved in 40 ml of dichloromethane, and 4.1 g (32.4 mmol) of oxalyl chloride and 1.5 ml of dimethylformamide were added. The mixture was stirred at 25° C. for 1.5 hours, after which the solvent was removed. This gave 3.9 g of colorless crystals. Silica gel chromatography (mobile phase: toluene/methyl-tert-butyl ether) gave:

2-[(8-chloroquinolin-5-yl)carbonyl]-1-chloro-4,4,6,6-tetramethylcyclohex-1-ene-3,5-dione: Yield 0.65 g (colorless crystals); m.p.: 180° C.;

2-[(8-chloroquinolin-5-yl)chloromethylidene-4,4,6,6-tetramethyl-cyclohexane-1,3,5-trione: Yield: 0.35 g (colorless crystals); m.p.: 156° C.

2-[(8-Chloroquinolin-5-yl)-1-(4'-oxo-1',4'-dihydropyrid-1'-yl)-4,4,6,6-tetramethyl-cyclohex-1-ene-3,5-dione (Compound 2.46) and 2-[(8-chloroquinolin-5-yl)-(4'-oxo-1',4'-dihydropyrid-1'-yl)-methylidene]-4,4,6,6-tetramethyl-cyclohexane-1,3,5-trione (Compound 3.5)

1.0 g (2.6 mmol) of a mixture of the compounds 2.22 and 3.1 was dissolved in 25 ml of methylene chloride, 0.82 g (8.7 mmol) of 4-hydroxypyridine were added and the mixture was stirred at 40° C. for 8 hours. Insoluble components were subsequently filtered off, the solvent was removed and the residue was chromatographed over silica gel (mobile phase: methylene chloride/methanol). This gave:

2-[(8-chloroquinolin-5-yl)-4'-oxo-1',4'-dihydropyridin-1'-yl)methylidene-4,4,6,6-tetramethylcyclohexane-1,3,5-trione: Yield 0.40 g (colorless oil);

2-[(8-chloroquinolin-5-yl)carbonyl]-1-(4'-oxo-1',4'-dihydro-40 pyrid-1'-yl)-4,4,6,6-tetramethylcyclohex-1-ene-3,5-dione: Yield 0.25 g (colorless crystals); m.p.>210° C.

2-(8-fluoroquinolin-5-yl)carbonyl-1,5-di(ethoxycarbonyloxy)-4,4,6,6-tetramethyl-cyclohex-1-ene-3,5-dione (Compound 3.20) 0.12 g (4 mmol) of sodium hydride was dissolved in 10 ml of tetrahydrofuran, 0.36 g (1 mmol) of 2-[(8-fluoroquinolin-5-yl)carbonyl]-4,4,6,6-tetramethyl-1-hydroxy-cyclohexane-3,5-dione in 5 ml of tetrahydrofuran was added dropwise at room temperature and the mixture was stirred at 40° C. for 1 hour. At room temperature, 0.43 g (4 mmol) of ethyl chloroformate were subsequently added dropwise, and the mixture was heated under reflux for 3 hours. After cooling, water was added and the mixture was extracted with ethyl acetate, the organic phase was washed with 2% strength potassium carbonate solution and water and dried and the solvent was removed. This gave 0.45 g of a colorless oil).

2-[(8-Chloroquinolin-5-yl)carbonyl]-1-[(dimethylamino) carbonyl-thio]-4,4,6,6-tetramethyl-cyclo-hex-1-ene-3,5-dione (Compound 2.45) and 2-{(8-chloroquinolin-5-yl)-[(dimethylamino)carbonylthio]-methylidene}-4,4,6,6-tetramethylcyclohexane-1,3,5-trione (Compound 3.4)

0.50 g (1.3 mmol) of 2-[(8-chloroquinolin-5-yl)carbonyl]4,4,6,6-tetramethyl-cyclohexane-1,3,5-trione was dissolved in 15 ml of tetrahydrofuran, 0.52 g (5.2 mmol) of triethylamine was added and 0.32 g (2.6 mmol) of dimethylaminothiocarbonyl chloride in 5 ml of tetrahydrofuran was added dropwise. The mixture was stirred at room temperature for 30 hours, the solvent was removed, and the residue was taken up in the ethyl acetate, washed with 5% strength potassium carbonate solution and water, dried, concentrated and chromatographed over silica gel using cyclohexane/ethyl acetate. This gave 2-[(8-chloroquinolin-5-yl)carbonyl]-1-[(dimethylamino) carbonylthio]-4,4,6,6-tetramethyl-cyclohex-1-ene-3,5-dione: Yield 0.5 g (colorless crystals); m.p. 138° C.;

2-{(8-chloroquinolin-5-yl)-[(dimethylamino)carbonyl-thio] methyl-i dene}-4,4,6,6-tetramethylcyclohexane-1,3,5-trione: Yield: 0.2 g (colorless crystals) m.p. 75° C.

2-[(8-difluoromethylquinolin-5-yl)carbonyl]-1-chloro-4,4,6,6-tetramethyl-cyclohex-1-ene-3,5-dione (Compound 2.31)

Step a) Methyl 8-formyl-5-quinolinecarboxylate 28.8 g (103 mmol) of 8-(bromomethyl)-5-quinolinecarboxylate were dissolved in 200 ml of acetonitrile, 36.1 g (309 mmol) of N-methylmorpholine N-oxide were added, the mixture was stirred at 25° C. for 7 hours and the solvent was then removed. Silica gel chromatography (mobile phase: cyclohexane/ethyl acetate) gave 12.0 g of methyl 8-formyl-5-quinolinecarboxylate (colorless crystals), m.p.: 128° C.

Step b) 8-difluoromethyl-5-quinolinecarboxylate 0.5 g (2.3 mmol) of methyl 8-formyl-5-quinolinecarboxylate was dissolved in 50 ml of dichloroethane and, at −20° C., 1.1 g (6.8 mmol) of diethylaminosulfur trifluoride (DAST) were added dropwise. The mixture was stirred at −20° C. for 30 min and then armed to 25° C., and 50 ml of water were added dropwise. The aqueous phase was extracted with methylene chloride, the combined organic phases were washed with sodium bicarbonate solution and dried and the solvent was removed. Yield: 0.7 g of colorless crystals;

$^1$H-NMR (δ in ppm, d$^6$-DMSO): 9.28 (d, 1H); 9.04 (s, 1H); 8.36 (d, 1H); 8.11 (d, 1H); 7.90 (t, 1H); 7.80 (brd s, 1H); 3.96 (s, 3H).

Step c) 8-difluoromethyl-5-quinolinecarboxylic acid 0.5 g (2.0 mmol) of methyl 8-difluoromethyl-5-quinolinecarboxylate was dissolved in 5 ml of ethanol, 0.43 g (10.5 mmol) of sodium hydroxide and 1 ml of water were added, and the mixture was stirred at 25° C. for 20 hours. The solvents were subsequently removed, the residue was taken up in water, washed twice with methylene chloride and adjusted to pH 1 using 10 N hydrochloric acid, and the precipitate was filtered off with suction. Drying gave 0.5 g of 8-difluoromethyl-5-quinolinecarboxylic acid (colorless crystals);
$^1$H-NMR (δ in ppm, d$^6$-DMSO): 9.35 (d, 1H); 9.04 (s, 1H); 8.38 (d, 1H); 8.10 (d, 1H); 7.92 (t, 1H); 7.78 (brd s, 1H).

Step d) 2-[(8-difluoromethylquinolin-5-yl)carbonyl]-4,4,6,6-tetramethylcyclohexane-1,3,5-trione 0.26 g (1.4 mmol) of 2,2,4,4-tetramethylcyclohexane-1,3,5-trione was dissolved in 10 ml of acetonitrile, 0.34 g (1.4 mmol) of 8-difluoromethyl-5-quinolinecarboxylic acid and 0.38 g (1.9 mmol) of dicyclohexylcarbodiimide were added and the mixture was stirred at 25° C. for 17 hours. 0.57 g (5.6 mmol) of triethylamine and 5 drops of trimethylsilyl cyanide were then added to the suspension, and stirring was continued at 25° C. for a further 25 hours. 50 ml of 5% strength potassium carbonate solution were subsequently added, the mixture was filtered, the filtrate was washed with methyl tert-butyl ether, the aqueous phase was adjusted to pH 2 using concentrated hydrochloric acid and the precipitate was filtered off, washed with water and dried. Yield: 0.25 g (colorless crystals);
$^1$H-NMR (δ in ppm, CDCl$_3$): 17.5 (s, 1H); 9.02 (q, 1H); 8.24 (d, 1H); 8.06 (d, 1H); 7.82 (t, 1H); 7.50 (m, 2H); 1.60 (s, 6H); 1.36 (s, 6H).

Step e) 2-[(8-Difluoromethylquinolin-5-yl)carbonyl]-1-chloro-4,4,6,6-tetramethyl-cyclohex-1-ene-3,5-dione (Compound 2.31)

0.25 g (0.65 mmol) of 2-(8-difluoromethylquinolin-5-yl) carbonyl-4,4,6,6-tetramethyl-cyclohexane-1,3,5-trione was dissolved in 15 ml of dichloromethane and 0.25 g (1.95 mmol) of oxalyl chloride and 7 drops of dimethylformamide were added. The mixture was stirred at 25° C. for 17 hours, after which the solvent was removed. This gave 0.2 g of colorless crystals.

Preparation of the Precursor 2-[(8-difluoromethoxyquinolin-5-yl)carbonyl]-4,4,6,6-tetramethylcyclohexane-1,3,5-trione Step a) Methyl 8-hydroxy-5-quinolincarboxylate 16.25 g (86 mmol) of 8-hydroxy-5-quinolinecarboxylic acid were dissolved in 70 ml of methanol, 3 ml of concentrated sulfuric acid were added and the mixture was heated under reflux for 25 hours. The solvent was then removed and the residue was taken up in ice-water, adjusted to a pH of 8 using sodium carbonate solution and filtered hot. The residue was extracted with methyl-tert-butyl ether for 7 hours on a jacketed Soxhlet extractor, and the solvent was subsequently removed from the extract. This gave 6.8 g of a brown powder;
$^1$H-NMR (δ in ppm, d$^6$-DMSO): 9.38 (d, 1H); 8.90 (d, 1H); 8.26 (d, 1H); 7.71 (dd, 1H); 7.15 (d, 1H); 3.93 (s, 3H).

Step b) Methyl 8-difluoromethoxy-5-quinolinecarboxylate 1.0 g (5.0 mmol) of methyl 8-hydroxy-5-quinolinecarboxylate was dissolved in 20 ml of dimethylformamide, 0.76 g (5.5 mmol) of potassium carbonate was added and 14 g of chlorodifluoromethane were introduced at 40° C. over a period of 2 hours. Solid components were then filtered off, the solvent was removed and the residue was washed with water and dried. This gave 0.75 g of a brown powder;
$^1$H-NMR (δ in ppm, CDCl$_3$): 9.45 (d, 1H); 9.00 (d, 1H); 8.30 (d, 1H); 7.61 (dd, 1H); 7.49 (d, 1H); 7.18 (t, 1H); 3.99 (s, 3H).

Step c) 8-difluoromethoxy-5-quinolinecarboxylic acid 0.7 g (2.8 mmol) of methyl 8-difluoromethoxy-5-quinolinecarboxylate was suspended in 15 ml of water and 0.4 g (10 mmol) of sodium hydroxide was added. The mixture was stirred at 25° C. for 20 hours and then filtered off, and the filtrate was washed with methyl tert-butyl ether. The aqueous phase was adjusted to pH 3 using concentrated hydrochloric acid and filtered off, and the residue was dried. This gave 0.45 g of a colorless powder;
$^1$H-NMR (δ in ppm, d$^6$-DMSO): 13.5 (br, 1H); 9.39 (d, 1H); 9.03 (d, 1H); 8.32 (d, 1H); 7.78 (dd, 1H); 7.62 (d, 1H); 7.60 (t, 1H).

Step d) 2-[(8-difluoromethoxyquinolin-5-yl)carbonyl]-4,4,6,6-tetramethylcyclohexane-1,3,5-trione 0.4 g (1.7 mmol) of 8-difluoromethoxy-5-quinolinecarboxylic acid was dissolved in 20 ml of acetonitrile, 0.4 g (1.9 mmol) of N,N-dicyclohexylcarbodiimide and 0.3 g (1.7 mmol) of 2,2,4,4-tetramethylcyclohexane-1,3,5-trione were added and the mixture was stirring at 25° C. for 20 hours. 0.4 g (4.0 mmol) of triethylamine and 2 drops of trimethylsilyl cyanide were then added, and stirring was continued at 30–35° C. for a further 3 hours. The precipitate was filtered off, and the filtrate was concentrated, 20 ml of 5% strength potassium carbonate solution were added and the mixture was washed with methyl tert-butyl ether. The aqueous phase was subsequently adjusted to pH 3 using concentrated hydrochloric acid and extracted with ethyl acetate. The solvent was removed and the residue was chromatographed over silica gel (mobile phase: methylene chloride/methanol). This gave 0.2 g of a colorless powder;
35 $^1$H-NMR (δ in ppm, CDCl$_3$): 16.5 (br, 1H); 9.02 (d, 1H); 8.30 (d, 1H); 7.51 (m, 2H); 7.21 (d, 1H); 7.17 (t, 1H); 1.60 (s, 6H); 1.35 (s, 6H).

In addition to the cyclohexenone quinolinoyl derivatives of the formula I described above, further derivatives which were prepared or are preparable in a similar manner or in a manner known per se are listed in Tables 2 and 3:

TABLE 2

Structure Ia: cyclohexanone-carbonyl-quinoline with substituents R1 (8-position), R2, R3 (quinoline), R5 (3-position of cyclohexenone), (R6)1 on cyclohexanone ring.

| No. | R$^1$ | R$^2$ | R$^3$ | R$^5$ | (R$^6$)$_1$ | m.p. [° C.] or $^1$H-NMR [ppm] |
|---|---|---|---|---|---|---|
| 2.1 | F | H | H | OCOC$_6$H$_5$ | 4,4,6,6-(CH$_3$)$_4$-5-oxo | 178 |
| 2.2 | F | H | H | OCOC(CH$_3$)$_3$ | 4,4,6,6-(CH$_3$)$_4$-5-oxo | 9.22(d, 1H); 9.03(d, 1H); 7.98(q, 1H); 7.62(q, 1H); 7.39(t, 1H); 1.49 (s, 6H); 1.40(s, 6H); 1.11(s, 9H) |
| 2.3 | Cl | H | H | OCOC$_6$H$_5$ | 4,4,6,6-(CH$_3$)$_4$-5-oxo | >200 |
| 2.4 | Cl | H | H | OCOC(CH$_3$)$_3$ | 4,4,6,6-(CH$_3$)$_4$-5-oxo | 9.20(dd, 2H); 8.85(q, 2H); 7.60(q, 1H); 1.40(s, 12H); 1.12(s, 9H) |
| 2.5 | CH$_3$ | H | H | OPS(OCH$_2$CH$_3$)$_2$ | 4,4,6,6-(CH$_3$)$_4$-5-oxo | 9.50(d, 1H); 8.98(d, 1H); 8.06(d, 1H); 7.60(m, 2H); 3.95(m, 4H); 2.90 (s, 3H); 1.65(s, 6H); 1.51(s, 6H) |
| 2.6 | CH$_3$ | H | H | OCOSCH$_3$ | 4,4,6,6-(CH$_3$)$_4$-5-oxo | 128 |
| 2.7 | CH$_3$ | H | H | OCSN(CH$_3$)$_2$ | 4,4,6,6-(CH$_3$)$_4$-5-oxo | 163 |
| 2.8 | CH$_3$ | H | H | OCOC$_6$H$_5$ | 4,4,6,6-(CH$_3$)$_4$-5-oxo | 9.05(d, 1H); 9.85(d, 1H); 7.92(d, 1H); 7.72(d, 1H); 7.51(d, 1H); 7.48 (t, 1H); 7.35(q, 1H); 7.28(t, 2H); 2.79(s, 3H); 1.62(s, 6H); 1.55(s, 6H) |
| 2.9 | CH$_3$ | H | H | OPO[N(CH$_3$)]$_2$ | 4,4,6,6-(CH$_3$)$_4$-5-oxo | 9.41(d, 1H); 8.95(d, 1H); 8.07(d, 1H); 7.58(q, 1H); 7.50(q, 1H); 2.88 (s, 3H); 2.45(s, 6H); 2.42(s, 6H); 1.65(s, 6H); 1.48(s, 6H) |
| 2.10 | CH$_3$ | H | H | OCO(CH$_2$)$_3$O(2,4-Cl2-C$_6$H$_3$) | 4,4,6,6-(CH$_3$)$_4$-5-oxo | oil |
| 2.11 | CH$_3$ | H | H | OCOCH(CH$_3$)O(2-CH$_3$-4-Cl—C$_6$H$_3$) | 4,4,6,6-(CH$_3$)$_4$-5-oxo | oil |
| 2.12 | CH$_3$ | H | H | OCOC(CH$_3$)$_3$ | 4,4,6,6-(CH$_3$)$_4$-5-oxo | 9.20(d, 1H); 8.85(d, 1H); 7.80(d, 1H); 7.51(d, 1H); 7.48(q, 1H); 2.85 (s, 3H); 1.55(s, 6H); 1.50(s, 6H); 1.08(s, 9H) |
| 2.13 | F | H | H | OCOC(CH$_3$)$_3$ | 4,4,6-(CH$_3$)$_3$ | oil |
| 2.14 | Cl | H | H | OCOCH$_2$CH$_3$ | 4,4,6,6-(CH$_3$)$_4$-5-oxo | 9.13(d, 1H); 9.02(d, 1H); 7.85(s, 2H); 7.58(q, 2H); 2.40(q, 2H); 1.60 (s, 6H); 1.50(s, 6H); 1.05(t, 3H) |
| 2.15 | F | H | H | OCOSCH$_3$ | 4,4,6,6-(CH$_3$)$_4$-5-(OH) | 190–192 |
| 2.16 | Cl | H | H | OCOSCH$_3$ | 4,4,6,6-(CH$_3$)$_4$-5-oxo | 84 |
| 2.17 | F | H | H | OCOSCH$_3$ | 4,4,6,6-(CH$_3$)$_4$-5-oxo | 72 |
| 2.18 | CH$_3$ | H | H | OCH$_3$ | 4,4,6,6-(CH$_3$)$_4$-5-oxo | 9.44(d, 1H); 9.03(d, 1H); 7.88(d, 1H); 7.59(m, 2H); 3.92(s, 3H); 2.90 (s, 3H); 1.50(s, 6H); 1.38(s, 6H) |
| 2.19 | F | H | H | OSO$_2$CH$_3$ | 4,4,6,6-(CH$_3$)$_4$-5-(OH) | 9.30(d, 1H); 9.02(d, 1H); 7.93(q, 1H); 7.61(q, 1H); 7.40(q, 1H); 3.01 (s, 3H); 1.57(s, 3H); 1.53(s, 3H); 1.32(s, 3H); 1.28(s, 3H) |
| 2.20 | F | H | H | OCOOCH$_2$CH$_3$ | 4,4,6,6-(CH$_3$)$_4$-5-(OCOOCH$_2$CH$_3$) | 9.18(d, 1H); 9.02(s, 1H); 7.92(q, 1H); 7.65(q, 1H); 7.41(q, 1H); 4.32 (q, 2H); 4.11(q, 1H); 1.45(s, 3H); 1.40(s, 3H); 1.38(s, 3H); 1.30(s, 3H); 1.22(s, 3H); 1.15(s, 3H) |
| 2.21 | F | H | H | OCH$_3$ | 4,4,6,6-(CH$_3$)$_4$-5-oxo | 9.45(d, 1H); 9.03(d, 1H); 7.96(q, 1H); 7.68(q, 1H); (7.40(t, 1H); 3.88(s, 3H); 1.50(s, 6H); 1.39(s, 6H) |
| 2.22 | Cl | H | H | Cl | 4,4,6,6-(CH$_3$)$_4$-5-oxo | 180 |
| 2.23 | F | H | H | Cl | 4,4,6,6-(CH$_3$)$_4$-5-oxo | 152 |
| 2.24 | Cl | H | H | S(4-CH$_3$—C$_6$H$_4$) | 4,4,6,6-(CH$_3$)$_4$-5-oxo | 119 |
| 2.25 | S(4-CH$_3$—C$_6$H$_4$) | H | H | S(4-CH$_3$—C$_6$H$_4$) | 4,4,6,6-(CH$_3$)$_4$-5-oxo | 132–135 |
| 2.26 | Cl | H | H | Cl | 4,4,6,6-(CH$_3$)$_4$-5-oxo | |
| 2.27 | O(tetra-hydro-furan-3-yl) | H | H | Cl | 4,4,6,6-(CH$_3$)$_4$-5-oxo | 9.65(d, 1H); 9.05(d, 1H); 8.83(d, 1H); 7.66(q, 1H); 6.95(d, 1H); 5.23 (m, 1H); 4.21(d, 2H); 4.05(m, 2H); 2.39(m, 2H); 1.62(s, 6H); 1.48(s, 6H) |
| 2.28 | CH$_3$ | H | H | Cl | 4,4,6,6-(CH$_3$)$_4$-5-oxo | 194 |
| 2.29 | F | H | H | Cl | 4,4,6-(CH$_3$)$_3$ | oil |
| 2.30 | CH$_3$ | H | H | Br | 4,4,6,6-(CH$_3$)$_4$-5-oxo | oil |

TABLE 2-continued

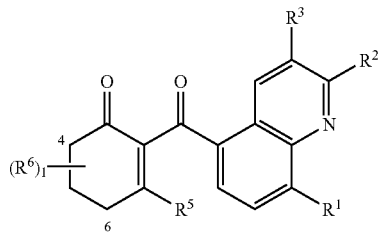

Ia

| No. | R¹ | R² | R³ | R⁵ | (R⁶)₁ | m.p. [° C.] or ¹H-NMR [ppm] |
|---|---|---|---|---|---|---|
| 2.31 | CHF₂ | H | H | Cl | 4,4,6,6-(CH₃)₄-5-oxo | 9.40(d, 1H); 9.05(d, 1H); 8.05(d, 1H); 7.86(t, 1H); 7.80(d, 1H); 7.65 (q, 1H); 1.59(s, 6H); 1.48(s, 6H) |
| 2.32 | CF₃ | H | H | Cl | 4,4,6,6-(CH₃)₄-5-oxo | oil |
| 2.33 | CF₃ | CH₃ | H | Cl | 5,5-(CH₃)₂ | 9.15(d, 1H); 8.10(d, 1H); 7.75(d, 1H); 7.52(d, 1H); 3.02(s, 2H); 2.91 (s, 2H); 2.80(s, 3H); 1.20(s, 6H) |
| 2.34 | CH₃ | H | H | N(CH₃)OCH₃ | 4,4,6,6-(CH₃)₄-5-oxo | oil |
| 2.35 | CH₃ | H | H | SCH₃ | 4,4,6,6-(CH₃)₄-5-oxo | 9.50(d, 1H); 9.02(d, 1H); 7.80(d, 1H); 7.50(m, 3H); 2.90(s, 3H); 2.30 (s, 3H); 1.50(s, 6H); 1.35(s,3H); 1.25(s, 3H) |
| 2.36 | Cl | H | H | 1-pyrazolyl | 4,4,6,6-(CH₃)₄-5-oxo | 9.30(d, 1H); 9.05(d, 1H); 7.80(d, 1H); 7.75(d, 1H); 7.61(q, 1H); 7.52 (d, 1H); 7.40(s, 1H); 6.11(s, 1H); 1.65(s, 3H); 1.60(s, 3H); 1.50(s, 6H) |
| 2.37 | Cl | H | H | N(CH₃)OCH₃ | 4,4,6,6-(CH₃)₄-5-oxo | 190 |
| 2.38 | CH₃ | H | H | 1-pyrolidinyl | 4,4,6,6-(CH₃)₄-5-oxo | oil |
| 2.39 | CH₃ | H | H | 4-morpholinyl | 4,4,6,6-(CH₃)₄-5-oxo | 205 |
| 2.40 | Cl | H | H | 4-morpholinyl | 4,4,6,6-(CH₃)₄-5-oxo | 205 |
| 2.41 | CH₃ | H | H | Cl | 4,4,6,6-(CH₃)₄-5-oxo | 194 |
| 2.42 | CH₃ | H | H | 1-pyrazolyl | 4,4,6,6-(CH₃)₄-5-oxo | 150 |
| 2.43 | CF₃ | H | H | 4-morpholinyl | 4,4,6,6-(CH₃)₄-5-oxo | oil |
| 2.44 | CHNOCH₃ | H | H | Cl | 4,4,6,6-(CH₃)₄-5-oxo | oil |
| 2.45 | Cl | H | H | SCON(CH₃)₂ | 4,4,6,6-(CH₃)₄-5-oxo | 138 |
| 2.46 | Cl | H | H | 4-oxo-1,4-dihydro-pyrid-1-yl | 4,4,6,6-(CH₃)₄-5-oxo | >210 |
| 2.47 | F | H | H | Cl | 4,6-(CH₃)₂-4-SCH₃ | oil |
| 2.48 | CH₃ | H | H | SCON(CH₃)₂ | 4,4,6,6-(CH₃)₄-5-oxo | 166 |
| 2.49 | CH₃ | H | H | OP(OCH₂CH₃)₂ | 4,4,6,6-(CH₃)₄-5-oxo | 9.65(d, 1H); 8.97(d, 1H); 7.79(d, 1H); 7.60(m, 2H); 4.00(m, 4H); 2.91 (s, 3H); 1.71(s, 6H); 1.51(s, 6H) |
| 2.50 | OCH₃ | H | H | Cl | 4,4,6,6-(CH₃)₄-5-oxo | 9.65(d, 1H); 9.01(d, 1H); 7.83(d, 1H); 7.65(q, 1H); 7.02(d, 1H); 4.18 (s, 3H); 1.65(s, 6H); 1.55(s, 6H) |
| 2.51 | F | H | H | OCOS(CH₂)₇CH₃ | 4,4,6,6-(CH₃)₄-5-oxo | 9.20((d, 1H); 9.02(d, 1H); 7.89 (q, 1H); 7.60(q, 1H); 7.40(t, 1H); 2.62(t, 2H); 1.55(s, 6H); 1.48(s, 6H); 1.1–1.5(m, 12H); 0.85(t, 3H) |
| 2.52 | F | H | H | Cl | 4,6-(ethan-1,2-diyl)¹⁾ | 9.55(d, 1H); 9.02(d, 1H); 7.78 (q, 1H); 7.65(q, 1H); 7.40(t, 1H); 3.24(m, 1H); 3.17(m, 1H); 2.41(d, 1H); 1.8–2.4(m, 5H) |
| 2.53 | SCH₃ | H | H | OCOSCH₃ | 4,4,6,6-(CH₃)₄-5-oxo | 147 |
| 2.54 | F | H | H | OCOSCH₂CH₃ | 4,4,6,6-(CH₃)₄-5-oxo | 107 |
| 2.55 | Br | H | H | OCOC(CH₃)₃ | 4,4,6,6-(CH₃)₄-5-oxo | 134 |
| 2.56 | Br | H | H | OCO(C₆H₅) | 4,4,6,6-(CH₃)₄-5-oxo | 228 |
| 2.57 | Cl | H | H | F | 4,4,6,6-(CH₃)₄-5-oxo | 181 |
| 2.58 | F | H | H | SO₂CH₃ | 4,4,6,6-(CH₃)₄-5-oxo | 206 |
| 2.59 | F | H | H | SOCH₃ | 4,4,6,6-(CH₃)₄-5-oxo | 190 |
| 2.60 | SCH₂F | H | H | F | 4,4,6,6-(CH₃)₄-5-oxo | 9.50(d, 1H); 9.00(d, 1H); 7.81 (s, 2H); 7.65(q, 1H); 6.01(d, 2H); 1.60(s, 6H); 1.51(s, 6H) |
| 2.61 | F | H | H | SC₆H₅ | 4,4,6,6-(CH₃)₄-5-oxo | 65 |
| 2.62 | F | H | H | SO₂C₆H₅ | 4,4,6,6-(CH₃)₄-5-oxo | 111 |
| 2.63 | F | H | H | SCH₃ | 4,4,6,6-(CH₃)₄-5-oxo | 143 |
| 2.64 | CHF₂ | H | H | F | 4,4,6,6-(CH₃)₄-5-oxo | 183 |
| 2.65 | Cl | CHF₂ | H | F | 4,4,6,6-(CH₃)₄-5-oxo | 173 |
| 2.66 | F | H | H | F | 4,4,6,6-(CH₃)₄-5-oxo | 153 |

¹⁾R⁴ = 4-Oxo-(bicyclo[3.2.1]oct-2-en-3-yl)carbonyl

TABLE 3

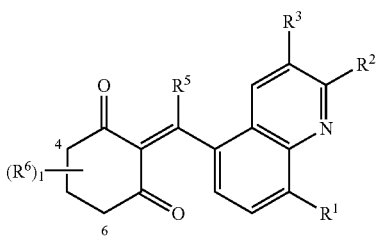

Ib

| No. | R¹ | R² | R³ | R⁵ | R⁶ | m.p. [° C.] or ¹H-NMR [ppm] |
|---|---|---|---|---|---|---|
| 3.1 | Cl | H | H | Cl | 4,4,6,6-(CH₃)₄-5-oxo | 156 |
| 3.2 | CH₃ | H | H | 1-(1,2,4-triazolyl) | 4,4,6,6-(CH₃)₄-5-oxo | 9.00(d, 1H); 8.09(s, 1H); 7.82(d, 1H); 7.72(s, 1H); 7.68(d, 1H); 7.47 (d, 1H); 7.35(q, 1H); 2.95(s, 3H); 1.55(s, 6H); 1.30(s, 6H) |
| 3.3 | Cl | H | H | 4-morpholinyl | 4,4,6,6-(CH₃)₄-5-oxo | 9.15(d, 1H); 8.32(d, 1H); 7.82(d, 1H); 7.60(q, 1H); 7.45(d, 1H); 4.05 (m, 2H); 3.68(m, 4H); 3.35(m, 1H); 3.25(m, 1H); 1.30(s, 6H); 1.22(s, 6H) |
| 3.4 | Cl | H | H | SCON(CH₃)₂ | 4,4,6,6-(CH₃)₄-5-oxo | 75 |
| 3.5 | Cl | H | H | 4-oxo-1,4-dihydro-pyrid-1-yl | 4,4,6,6-(CH₃)₄-5-oxo | 9.02(d, 1H); 8.42(d, 1H); 7.80(2d, 3H); 7.50(q, 1H); 7.38(d, 1H); 6.72 (d, 2H); 1.50(s, 12H) |
| 3.6 | Cl | H | H | N(CH₃)₂ | 4,4,6,6-(CH₃)₄-5-oxo | 190 |

The compounds of the formula I and their agriculturally useful salts are suitable, both in the form of isomer mixtures and in the form of the pure isomers, as herbicides. The herbicidal compositions comprising compounds of the formula I control vegetation on non-crop areas very efficiently, especially at high rates of application. They act against broad-leaved weeds and harmful grasses in crops such as wheat, rice, maize, soya and cotton without causing any significant damage to the crop plants. This effect is mainly observed at low rates of application.

Depending on the application method used, the compounds of the formula I, or the compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N.rustica*), *Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

In addition, the compounds of the formula I may also be used in crops which tolerate the action of herbicides owing to breeding, including genetic engineering methods.

The compounds of the formula I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for broadcasting or granules, by means of spraying, atomizing, dusting, broadcasting or watering. The use forms depend on the intended aims; in any case, they should guarantee a very fine distribution of the active compounds according to the invention.

The herbicidal compositions comprise a herbicidally effective amount of at least one compound of the formula I or of an agriculturally useful salt of I, and auxiliaries which are customary for the formulation of crop protection agents.

Essentially, suitable inert auxiliaries include: mineral oil fractions of medium to high boiling point, such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, or strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the cyclohexenonequinolinoyl derivatives of the formula I, either as such or dissolved in an oil or solvent, can be homogenized in water by means of a wetting agent, tackifier, dispersant or emulsifier. Alternatively, it is possible to prepare concentrates comprising active substance, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose. Powders, materials for broadcasting and dusts can be prepared by mixing or grinding the active substances together with a solid carrier.

Granules, e.g. coated granules, impregnated granules and homogeneous granules, can be prepared by binding the active compounds to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the compounds of the formula I in the ready-to-use preparations can be varied within wide ranges. In general, the formulations comprise from about 0.001 to 98% by weight, preferably 0.01 to 95% by weight of at least one active compound. The active compounds are employed in a purity of from 90% to 100%, preferably 95% to 100% (according to the NMR spectrum).

The following formulation examples illustrate the production of such preparations:

I. 20 parts by weight of the compound No. 2.2 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. 2.4 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the compound No. 2.16 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the compound No. 2.18 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the compound No. 2.22 are mixed with 97 parts by weight of finely divided kaolin. This gives a dust which comprises 3% by weight of the active compound.

VI. 20 parts by weight of the compound No. 2.46 are mixed intimately with 2 parts by weight of the calcium salt of dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. 3.1 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII. 1 part by weight of the compound No. 3.4 is dissolved in a mixture composed of 80 parts by weight of cyclohexanone and 20 parts by weight of Wettol® EM 31 (nonionic emulsifier based on ethoxylated castor oil). This gives a stable emulsion concentrate.

The compounds of the formula I or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into contact as little as possible, if at all, with the leaves of the sensitive crop plants, while the active compounds reach the leaves of undesirable plants growing underneath, or the bare soil surface (post-directed, lay-by).

The application rates of the compound of the formula I are from 0.001 to 3.0, preferably 0.01 to 1.0 kg/ha of active substance (a.s.), depending on the control target, the season, the target plants and the growth stage.

To widen the activity spectrum and to achieve synergistic effects, the cyclohexenonequinolinoyl derivatives of the formula I may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds of the formula I, alone or else concomitantly in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

Use Examples

The herbicidal activity of the cyclohexenonequinolinoyl derivatives of the formula I was demonstrated by the following greenhouse experiments:

The culture containers used were plastic pots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this was adversely affected by the active compounds.

For the post-emergence treatment, the test plants were first grown to a height of 3 to 15 cm, depending on the plant habit, and only then treated with the active compounds which had been suspended or emulsified in water. The test plants were for this purpose either sown directly and grown in the same containers, or they were first grown separately as seedlings and transplanted into the test containers a few days prior to treatment. The application rate for the post-emergence treatment was 0.25 or 0.125 kg of a.s. (active substance)/ha.

Depending on the species, the plants were kept at 10–25° C. or 20–35° C. The test period extended over 2 to 4 weeks. During this time, the plants were tended, and their response to the individual treatments was evaluated.

The evaluation was carried out using a scale from 0 to 100. 100 means no emergence of the plants, or complete destruction of at least the aerial parts and 0 means no damage, or normal course of growth.

The plants used in the greenhouse experiments are composed of the following species:

| Scientific Name | Common Name |
|---|---|
| Abutilon theophrasti | velvet leaf |
| Chenopodium album | lambsquarters |
| Galium aparine | catchweed bedstraw |
| Ipomoea spp. | morning glory |
| Setaria faberi | giant foxtail |
| Setaria viridis | green foxtail |
| Solanum nigrum | black nightshade |

At application rates of 0.25 and 0.125 kg of a.s./ha, the compounds 2.2, 2.4 and 2.16, applied post-emergence, showed very good activity against harmful plants such as giant foxtail, green foxtail and black nightshade. Furthermore, the compounds 2.2 and 2.4 controlled velvet leaf and morning glory very efficiently. Compound 2.16 additionally showed excellent activity against the weeds lambsquarters and catchweed bedstraw.

What is claimed is:
1. A cyclohexenonequinolinoyl compound of the formula I

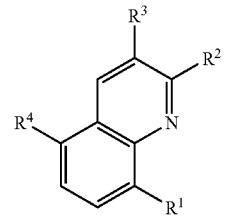

where:
$R^1$ is hydrogen, nitro, halogen, cyano, $C_1$–$C_6$-alkyl, $C_1$–$C_6$-haloalkyl, $C_1$–$C_6$-alkoxyiminomethyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N—($C_1$–$C_6$-alkyl)aminosulfonyl, N, N-di-($C_1$–$C_6$-alkyl) aminosulfonyl N—($C_1$–$C_6$-alkylsulfonyl)amino, N—($C_1$–$C_6$-haloalkylsulfonyl)amino, N—($C_1$–$C_6$-alkyl)-N-($C_1$–$C_6$-alkylsulfonyl)amino, N—($C_1$–$C_6$-alkyl)-N-($C_1$–$C_6$-haloalkylsulfonyl)amino, phenoxy, or phenylthio the four last-mentioned radicals may be partially or fully halogenated and/or may carry one to two of the following substituents:
nitro, cyano, $C_1$–$C_4$-alkyl, $C_1$–$C_4$-haloalkyl, $C_1$–$C_4$-alkoxy or $C_1$–$C_4$-haloalkoxy;
$R^2$, $R^3$ are hydrogen, $C_1$–$C_6$-alkyl, $C_1$–$C_6$-haloalkyl or halogen;
$R^4$ is a compound IIa or IIb

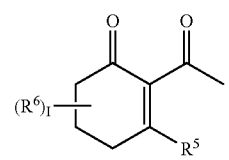

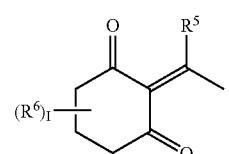

where
$R^5$ is halogen, $OR^7$, $SR^7$, $SOR^8$, $SO_2R^8$, $OSO_2R^8$, $POR^8R^9$, $OPR^8R^9$, $OPOR^8R^9$, $OPSR^8R^9$, $NR^{10}R^{11}$, $ONR^{11}R^{12}$
$R^6$ is nitro, halogen, cyano, $C_1$–$C_6$-alkyl, $C_1$–$C_6$-haloalkyl, di-($C_1$–$C_6$-alkoxy)methyl, di-($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkoxycarbonyloxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl;

or two radicals, which are linked to the same carbon, together form an —O—$(CH_2)_m$—O—, —O—$(CH_2)_m$—S—, —S—$(CH_2)_m$—S—, —O—$(CH_2)_n$— or —S—$(CH_2)_n$— chain which is unsubstituted or substituted by one to three radicals from the following group: halogen, cyano, $C_1$–$C_4$-alkyl, $C_1$–$C_4$-haloalkyl or $C_1$–$C_4$alkoxycarbonyl;

or two radicals, which are linked to the same carbon, together form a —$(CH_2)_p$ chain which possibly is interrupted by oxygen or sulfur and/or is unsubstituted or substituted by one to four radicals from the following group:

halogen, cyano, $C_1$–$C_4$-alkyl, $C_1$–$C_4$-haloalkyl or $C_1$–$C_4$alkoxycarbonyl;

or two radicals, which are linked to the same carbon, together form a methylidene group which is unsubstituted or substituted by one or two radicals from the following group:

halogen, hydroxyl, formyl, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

or two radicals, which are linked to the same carbon, together with this carbon form a carbonyl group;

or two radicals, which are linked to different carbons, together form a —$(CH_2)_n$ chain which is unsubstituted or substituted by one to three radicals from the following group: halogen, $C_1$–$C_6$-alkyl, $C_1$–$C_6$-alkoxy, hydroxyl or $C_1$–$C_6$-alkoxycarbonyl;

$R^7$ is $C_1$–$C_6$-alkyl, $C_3$–$C_1$-alkenyl, $C_3$–$C_6$-haloalkenyl, $C_3$–$C_6$-alkynyl, $C_3$–$C_6$-haloalkynyl, $C_3$–$C_6$-cyloalkyl, $C_1$–$C_{20}$-alkylcarbonyl, $C_2$–$C_6$-alkenylcarbonyl, $C_2$–$C_6$-alkynylcarbonyl, $C_3$–$C_6$-cyloalkylcarbonyl, $C_1$–$C_6$-alkoxycarbonyl, $C_3$–$C_6$-alkenyloxycarbonyl, $C_3$–$C_6$-alkynyloxycarbonyl, $(C_1$–$C_{20}$-alkylthio)carbonyl, $C_1$–$C_6$-alkylaminocarbonyl, $C_3$–$C_6$-alkenylaminocarbonyl, $C_3$–$C_6$-alkynylaminocarbonyl, N,N-di-$(C_1$–$C_6$-alkyl)aminocarbonyl, N—$(C_3$–$C_6$-alkenyl)-N-$(C_1$–$C_6$-alkyl) aminocarbonyl N—$(C_3$–$C_6$alkynyl)-N-$(C_1$–$C_6$-alkyl) aminocarbonyl, N—$(C_1$–$C_6$-alkoxy)-N-$(C_1$–$C_6$-alkyl) aminocarbonyl, N—$(C_3$–$C_6$-alkenyl)-N-$(C_1$–$C_6$-alkoxy) aminocarbonyl, N—$(C_3$–$C_6$-alkynyl)-N-$(C_1$–$C_6$-alkoxy) aminocarbonyl, di-$(C_1$–$C_6$-alkyl)-aminothiocarbonyl, $C_1$–$C_6$-alkylcarbonyl-$C_1$–$C_6$-alkyl, $C_1$–$C_6$-alkoxyimino-$C_1$–$C_6$-alkyl, N—$(C_1$–$C_6$-alkylamino) imino-$C_1$–$C_6$-alkyl or N,N-di-$(C_1$–$C_6$-alkylamino)imino-$C_1$–$C_6$-alkyl, it being possible for the above-mentioned alkyl, cycloalkyl and alkoxy radicals to be partially or fully halogenated and/or to carry one to three of the following groups: cyano, $C_1$–$C_4$-alkoxy, $C_1$–$C_4$-alkylthio, di-$(C_1$–$C_4$-alkyl)amino, $C_1$–$C_4$-alkylcarbonyl, $C_1$–$C_4$-alkoxy-$C_1$–$C_4$-alkoxycarbonyl, di-$(C_1$–$C_4$-alkyl)amino-$C_1$–$C_4$-alkoxycarbonyl, hydroxycarbonyl, $C_1$–$C_4$-alkylaminocarbonyl, di-$(C_1$–$C_4$-alkyl)aminocarbonyl, aminocarbonyl, $C_1$–$C_4$-alkylcarbonyloxy or $C_3$–$C_6$-cycloalkyl; phenyl, phenyl-$C_1$–$C_6$-alkyl, phenylcarbonyl-$C_1$–$C_6$-alkyl, phenylcarbonyl, phenoxycarbonyl, phenoxythiocarbonyl, phenoxy-$C_1$–$C_1$-alkylcarbonyl, phenylaminocarbonyl, N—$(C_1$–$C_6$-alkyl)-N-(phenyl)aminocarbonyl, or phenyl-$C_2$–$C_8$-alkenylcarbonyl, the phenyl radical of the 10 last-mentioned substituents may be partially or fully halogenated and/or may carry one to three of the following radicals:

nitro, cyano, $C_1$–$C_4$-alkyl, $C_1$–$C_4$-halogenalkyl, $C_1$–$C_4$-alkoxy or $C_1$–$C_4$-haloalkoxy;

$R^8,R^9$ are $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, amino, $C_1$–$C_6$-alkylamino, $C_1$–$C_6$-haloalkylamino, di-$(C_1$–$C_8$-alkyl)amino or di-$(C_1$–$C_6$-haloalkyl)amino, it being possible for the abovementioned alkyl, cycloalkyl and alkoxy radicals to be partially or fully halogenated and/or to carry one to three of the following groups:

cyano, $C_1$–$C_4$-alkoxy, $C_1$–$C_4$-alkylthio, di-$(C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-$(C_1$–$C_4$-alkyl)amino-$C_1$–$C_4$-alkoxycarbonyl, hydroxycarbonyl, $C_1$–$C_4$-alkylaminocarbonyl, di-$(C_1$–$C_4$alkyl)aminocarbonyl, aminocarbonyl, $C_1$–$C_4$-alkylcarbonyloxy or $C_3$–$C_6$-cycloalkyl;

phenyl, phenyl-$C_1$–C-alkyl, phenoxy, the phenyl radical of the last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{10}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di-$(C_1$–$C_6$-alkyl)amino or $C_1$–$C_6$-alkylcarbonylamino, where the abovementioned alkyl, cycloalkyl and alkoxy radicals may be partially or fully halogenated and/or may carry one to three radicals from the following group:

cyano, $C_1$–$C_4$-alkoxy, $C_1$–$C_4$-alkylthio, di-$(C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-$(C_1$–$C_4$-alkyl)amino-$C_1$–$C_4$-alkoxycarbonyl, hydroxycarbonyl, $C_1$–$C_4$-alkylaminocarbonyl, di-$(C_1$–$C_4$-alkyl)aminocarbonyl, aminocarbonyl, $C_1$–$C_4$-alkylcarbonyloxy or $C_3$–$C_6$-cycloalkyl;

phenyl, or phenyl-$C_1$–$C_6$-alkyl, where the phenyl radical of the two last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{11},R^{12}$ are $C_1$–$C_6$-alkyl, $C_3$–$C_6$-alkenyl, $C_3$–$C_6$-alkynyl or $C_1$–$C_6$-alkylcarbonyl;

l is 0 to 6;

m is 2 to 4;

n is 1 to 5;

p is 2 to 5;

and their agriculturally useful salts.

2. A cyclohexenonequinolinoyl compound of the formula I as claimed in claim 1 where $R^1$ is halogen, $C_1$–$C_6$-alkyl, $C_1$–$C_6$-haloalkyl, $C_1$–$C_6$-alkoxy, $C_1$–$C_6$-alkylthio, or phenylthio, the last-mentioned radical may be partially or fully halogenated and/or may carry one to two of the substituents mentioned below:

nitro, cyano, $C_1$–$C_4$-alkyl, $C_1$–$C_4$-haloalkyl, $C_1$–$C_4$-alkoxy or $C_1$–$C_4$-haloalkoxy;

$R^5$ is halogen, $OR^7$, $SR^7$, $SOR^8$, $SO_2R^8$, $OSO_2R^8$, $OPR^8R^9$, $OPOR^8R^9$ $OPSR^8R^9$, $NR^{10}R^{11}$ or N-bonded heterocyclyl.

3. A cyclohexenonequinolinoyl compound of the formula I as claimed in claim 1, where
$R^5$ is halogen, $OR^7$, $NR^{10}R^{11}$ or N-bonded heterocyclyl.

4. A cyclohexenonequinolinoyl compound of the formula I as claimed in claim 1, where
$R^7$ is $C_1$–$C_6$-alkyl, $C_1$–$C_{20}$alkylcarbonyl, $C_1$–$C_6$-alkoxycarbonyl, ($C_1$–$C_{20}$-alkylthio)carbonyl, N,N-di-($C_1$–$C_6$-alkyl)aminocarbonyl, phenyl, phenylcarbonyl or phenoxy-$C_1$–$C_6$-alkylcarbonyl, it being possible for the phenyl radical of the three last-mentioned substituents to be partially or fully halogenated and/or to carry one to three of the following radicals:
nitro, cyano, $C_1$–$C_4$-alkyl, $C_1$–$C_4$-haloalkyl, $C_1$–$C_4$-alkoxy or $C_1$–$C_4$-haloalkoxy;
$R^{10}$ is $C_1$–$C_6$-alkyl or $C_1$–$C_6$-alkoxy;
$R^{11}$ is $C_1$–$C_6$-alkyl.

5. A cyclohexenonequinolinoyl compound of the formula I as claimed in claim 1, where
$R^6$ is nitro, halogen, cyano, $C_1$–$C_6$-alkyl, $C_1$–$C_6$-haloalkyl, di-$C_1$-$C_6$-alkoxy)methyl, di-($C_1$–$C_6$-alkylthio)methyl, ($C_1$–$C_6$-alkoxy)($C_1$–$C_6$-alkylthio)-methyl, hydroxyl, $C_1$–$C_6$-alkoxy, $C_1$–$C_6$-haloalkoxy, $C_1$–$C_6$-alkoxycarbonyloxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl;
or
two radicals, which are linked to the same carbon, together form an —O—$(CH_2)_m$—O—, —O—$(CH_2)_m$—S—, —S—$(CH_2)_m$—S—, —O—$(CH_2)_n$— or —S—$(CH_2)_n$— chain which is unsubstituted or substituted by one to three radicals from the following group:
halogen, cyano, $C_1$–$C_4$-alkyl, $C_1$–$C_4$-haloalkyl or $C_1$–$C_4$-alkoxycarbonyl;
or
two radicals, which are linked to the same carbon, together form a —$(CH_2)_p$ chain which may be interrupted by oxygen or sulfur and which is unsubstituted or substituted by one to four radicals from the following group:
halogen, cyano, $C_1$–$C_4$-alkyl, $C_1$–$C_4$-haloalkyl or $C_1$–$C_4$-alkoxycarbonyl;
or
two radicals, which are linked to the same carbon, together with this carbon form a carbonyl group.

6. A process for preparing compounds of the formula I as claimed in claim 1 where $R^5$=halogen, which comprises reacting a cyclohexanedione derivative of the formula III,

III where the variables $R^1$ to $R^3$, and I are each as defined in claim 1, with a halogenating agent.

7. A process for preparing compounds of the formula I as claimed in claim 1 where $R^5$=$OR^7$, $OSO_2R^8$, $OPR^8R^9$, $OPOR^8R^9$ or $OPSR^8R^9$, which comprises reacting a cyclohexanedione derivative of the formula III,

III where the variables $R^1$ to $R^3$, and I are each as defined in claim 1, with a compound of the formula IVα, IVβ, IVγ, Ivδ or IVε, $L^1$—$R^7$ (IVα)

$L^1$—$SO_2R^8$ (IVβ)

$L^1$—$PR^8R^9$ (IVγ)

$L^1$—$POR^8R^9$ (IVδ)

$L^1$—$PSR^8R^9$ (IVε)

where the variables $R^7$ to $R^9$ are each as defined in claim 1 and $L^1$ is a nucleophilically replaceable leaving group.

8. A process for preparing compounds of the formula I as claimed in claim 1 where $R^5$=$OR^7$, $SR^7$, $POR^8R^9$, $NR^{10}R^{11}$, $ONR^{11}R^{12}$, or N-linked heterocyclyl, which comprises reacting a compound of the formula I α(≡I where $R^5$=halogen, $OSO_2R^8$), and/or I where $R^5$=halogen or $OSO_2R^8$
where the variables $R^1$ to $R^3$, $R^5$ and I are each as defined in claim 1, with a compound of the formula Vα, Vβ, Vγ, Vδ, Vε, Vη, Vθ, $HOR^7$ (Vα)

$HSR^7$ (Vβ)

$HPOR^8R^9$ (Vγ)

HNR¹⁰R¹¹ (Vδ)

HONR¹¹R¹² (Vε)

H(N-linked heterocyclyl) Vη where the variables $R^7$ to $R^{12}$ are each as defined in claim 1, if appropriate in the presence of a base.

9. A process for preparing compounds of the formula I as claimed in claim 1, where $R^5$=SOR$^8$, SO$_2$R$^8$, which comprises reacting a compound of the formula Iβ (≡I where $R^5$=SR$^8$),

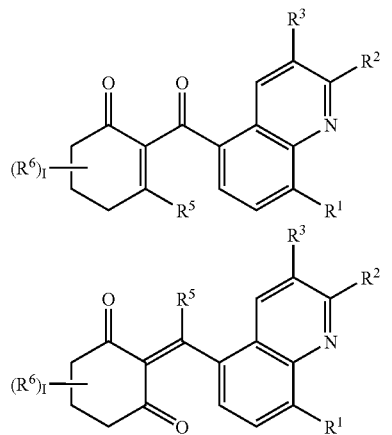

and/or

I where $R^5$=SR$^6$ where the variables $R^1$ to $R^8$ and I are each as defined in claim 1, with an oxidizing agent.

10. A composition, comprising a herbicidally effective amount of at least one cyclohexenonequinolinoyl compound of the formula I or an agriculturally useful salt of formula I as claimed in claim 1 and auxiliaries which are conventionally used for formulating crop protection agents.

11. A process for preparing a composition as claimed in claim 10, which comprises mixing a herbicidally effective amount of at least one cyclohexenonequinolinoyl derivative of the formula I or an agriculturally useful salt of formula I and auxiliaries which are conventionally used for formulating crop protection agents.

12. A method for controlling undesirable vegetation, which comprises allowing a herbicidally effective amount of at least one cyclohexenonequinolinoyl derivative of the formula I or an agriculturally useful salt of formula I as claimed in claim 1 to act on plants, their habitat and/or on seeds.

13. A cyclohexenonequinolinoyl compound of the formula I

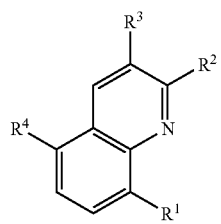

I where:

$R^1$ is hydrogen, nitro, halogen, cyano, $C_1$–$C_6$-alkyl, $C_1$–$C_6$-haloalkyl, $C_1$–$C_6$-alkoxyiminomethyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, aminosulfonyl, N—($C_1$–$C_6$-alkyl)aminosulfonyl, N, N-di-($C_1$–$C_6$-alkyl) aminosulfonyl, N—($C_1$–$C_6$-alkylsulfonyl)amino, N—($C_1$–$C_6$-haloalkylsulfonyl)amino, N—($C_1$–$C_6$-alkyl)-N-($C_1$–$C_6$-alkylsulfonyl)amino, N—($C_1$–$C_6$-alkyl)-N-($C_1$–$C_6$-haloalkylsulfonyl)amino, phenoxy, or phenylthio, the two last-mentioned radicals may be partially or fully halogenated and/or may carry one to two of the following substituents:

nitro, cyano, $C_1$–$C_4$-alkyl, $C_1$–$C_4$-haloalkyl, $C_1$–$C_4$-alkoxy or $C_1$–$C_4$-haloalkoxy;

$R^2$, $R^3$ are hydrogen, $C_1$–$C_6$-alkyl, $C_1$–$C_6$-haloalkyl or halogen;

$R^4$ is a compound IIa

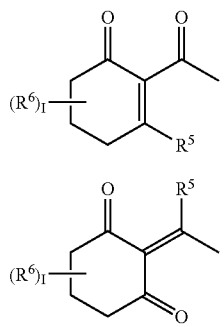

where $R^5$ is halogen, OR$^7$, SR$^7$, SOR$^8$, SO$_2$R$^8$, OSO$_2$R$^8$, POR$^8$R$^9$, OPR$^8$R$^9$, OPOR$^8$R$^9$, OPSR$^8$R$^9$, NR$^{10}$R$^{11}$, ONR$_{11}$R$^{12}$, N-linked heterocyclyl $R^6$ is nitro, halogen, cyano, $C_1$–$C_6$-alkyl, $C_1$–$C_6$-haloalkyl, di-($C_1$–$C_6$-alkoxy)methyl, di-($C_1$–$C_6$-alkylthio)methyl, ($C_1$–$C_6$-alkoxy)($C_1$–$C_6$-alkylthio)methyl, hydroxyl, $C_1$–$C_6$-alkoxy, $C_1$–$C_6$-haloalkoxy, $C_1$–$C_6$-alkoxycarbonyloxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, $C_1$–$C_6$-alkylcarbonyl, $C_1$–$C_6$-haloalkylcarbonyl, $C_1$–$C_6$-alkoxycarbonyl or $C_1$–$C_6$-haloalkoxycarbonyl;

or two radicals, which are linked to the same carbon, together form an —O—(CH$_2$)$_m$—O—, —O—(CH$_2$)$_m$—S—, —S—(CH$_2$)$_m$—S—, —O—(CH$_2$)$_n$- or —S—(CH$_2$)$_n$ chain which is unsubstituted or substituted by one to three radicals from the following group:

halogen, cyano, $C_1$–$C_4$-alkyl, $C_1$–$C_4$-haloalkyl or $C_1$–$C_4$alkoxycarbonyl;

or two radicals, which are linked to the same carbon, together form a —(CH$_2$)P chain which may be interrupted by oxygen or sulfur and/or is unsubstituted or substituted by one to four radicals from the following group:

halogen, cyano, $C_1$–$C_4$-alkyl, $C_1$–$C_4$-haloalkyl or $C_1$–$C_4$-alkoxycarbonyl;

or two radicals which are linked to the same carbon, together form a methylidene group which is unsubstituted or substituted by one or two radicals from the following group:

halogen, hydroxyl, formyl, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

or two radicals, which are linked to the same carbon, together with this carbon form a carbonyl group;

or two radicals, which are linked to different carbons, together form a —$(CH_2)_n$ chain which is unsubstituted or substituted by one to three radicals from the following group: halogen, $C_1$–$C_6$-alkyl, $C_1$–$C_6$-alkoxy, hydroxyl or $C_1$–$C_6$-alkoxycarbonyl;

$R^7$ is $C_1$–$C_6$,-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cyloalkyl, $C_1$–$C_{20}$-alkylcarbonyl, $C_2$–$C_6$-alkenylcarbonyl, $C_2$–$C_6$-alkynylcarbonyl, $C_3$–$C_6$-cyloalkylcarbonyl, $C_1$–$C_6$-alkoxycarbonyl, $C_3$–$C_6$-alkenyloxycarbonyl, $C_3$–$C_6$-alkynyloxycarbonyl, ($C_1$–$C_{20}$-alkylthio)carbonyl, $C_1$–$C_6$-alkylaminocarbonyl, $C_3$–$C_6$-alkenylaminocarbonyl, $C_3$–$C_6$-alkynylaminocarbonyl, N,N-di-($C_1$–$C_6$-alkyl)aminocarbonyl, N—($C_3$–$C_8$-alkenyl)-N-($C_1$–$C_6$-alkyl) aminocarbonyl, N—($C_3$–$C_6$-alkynyl)-N-($C_1$–$C_6$-alkyl) aminocarbonyl, N—($C_1$–$C_6$-alkoxy)-N-($C_1$–$C_6$-alkyl) aminocarbonyl, N—($C_3$–$C_6$-alkenyl)-N-($C_1$–$C_6$-alkoxy) aminocarbonyl N—($C_3$–$C_6$-alkynyl)-N-($C_1$–$C_6$-alkoxy) aminocarbonyl, di-($C_1$–$C_6$-alkyl)-aminothiocarbonyl, $C_1$–$C_6$-alkylcarbonyl-$C_1$–$C_6$-alkyl, $C_1$–$C_6$-alkoxyimino-$C_1$–$C_6$-alkyl, N—($C_1$–$C_6$-alkylamino) imino-$C_1$–$C_6$-alkyl or N,N-di-($C_1$–$C_6$-alkylamino)imino-$C_1$–$C_6$-alkyl, it being possible for the above-mentioned alkyl, cycloalkyl and alkoxy radicals to be partially or fully halogenated and/or to carry one to three of the following groups: cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino-$C_1$–$C_4$-alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_8$-cycloalkyl;

phenyl, phenyl-$C_1$–$C_6$-alkyl, phenylcarbonyl-$C_1$–$C_6$-alkyl, phenylcarbonyl, phenoxycarbonyl, phenoxythiocarbonyl, phenoxy-$C_1$–$C_6$-alkylcarbonyl, phenylaminocarbonyl, N—($C_1$–$C_6$-alkyl)-N-(phenyl) aminocarbonyl, or phenyl-$C_2$–$C_6$-alkenylcarbonyl, the phenyl radical of the 10 last-mentioned substituents may be partially or fully halogenated and/or may carry one to three of the following radicals;

nitro, cyano, $C_1$–$C_4$-alkyl, $C_1$–$C_1$-halogenalkyl, $C_1$–$C_4$-alkoxy or $C_1$–$C_4$-haloalkoxy;

$R^8$,$R^9$ are $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, amino, $C_1$–$C_6$-alkylamino, $C_1$–$C_6$-haloalkylamino, di-($C_1$–$C_6$-alkyl) amino or di-($C_1$–$C_6$-haloalkyl)amino, the abovementioned alkyl, cycloalkyl and alkoxy radicals may be partially or fully halogenated and/or may carry one to three of the following groups:

cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino-$C_1$–$C_4$-alkoxycarbonyl, hydroxycarbonyl, $C_1$–$C_4$-alkylaminocarbonyl, di-($C_1$–$C_4$alkyl)aminocarbonyl, aminocarbonyl, $C_1$–$C_4$-alkylcarbonyloxy or $C_3$–$C_6$-cycloalkyl;

phenyl, phenyl-$C_1$–$C_6$-alkyl phenoxy, the phenyl radical of the last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{10}$ is $C_1$–$C_6$-alkyl, $C_3$–$C_6$-alkenyl, $C_3$–$C_6$-haloalkenyl, $C_3$–$C_6$-alkynyl, $C_3$–$C_6$-haloalkynyl, $C_3$–$C_6$-cycloalkyl, hydroxyl, $C_1$–$C_6$-alkoxy, $C_3$–$C_6$-alkenyloxy, $C_3$–$C_6$-alkynyloxy, amino, $C_1$–$C_6$-alkylamino, di-($C_1$–$C_6$-alkyl)amino or $C_1$–$C_6$-alkylcarbonylamino, it being possible for the abovementioned alkyl, cycloalkyl and alkoxy radicals to be partially or fully halogenated and/or to carry one to three radicals from the following group:

cyano, $C_1$–$C_4$-alkoxy, $C_1$–$C_4$-alkylthio, di-($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, di-($C_1$–$C_4$-alkyl)amino$C_1$–$C_4$alkoxycarbonyl, hydroxycarbonyl, $C_1$–$C_4$-alkylaminocarbonyl, di-($C_1$–$C_4$-alkyl)aminocarbonyl, aminocarbonyl, $C_1$–$C_4$-alkylcarbonyloxy or $C_3$–$C_6$-cycloalkyl;

phenyl or phenyl-$C_1$–$C_6$-alkyl, the phenyl radical of the two last-mentioned substituents may be partially or fully halogenated and/or may carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{11}R^{12}$ are $C_1$–$C_6$-alkyl, $C_3$–$C_6$-alkenyl, $C_3$–$C_6$-alkynyl or $C_1$–$C_6$-alkylcarbonyl;

l is 0 to 6;

m is 2 to 4;

n is 1 to 5;

p is 2 to 5;

and their agriculturally useful salts.

14. A cycycloyhexenonequinolinoyl compound of the formula I as claimed in claim 13, where $R^1$ is halogen, $C_1$–$C_6$-alkyl, $C_1$–$C_6$-haloalkyl, $C_1$–$C_6$-alkoxy, $C_1$–$C_6$-alkylthio, or phenylthio, it being possible for the last-mentioned radical to be partially or fully halogenated and/or to carry one to two of the substituents mentioned below: nitro, cyano, $C_1$–$C_4$-alkyl, $C_1$–$C_4$-haloalkyl, $C_1$–$C_4$-alkoxy or $C_1$–$C_4$-haloalkoxy;

$R^5$ is halogen, $OR^7$, $SR^7$, $SOR^8$, $SO_2R^8$, $OSO_2R^8$, $OPR^8R^9$, $OPOR_8R^9$ $OPSR^8R^9$, $NR^{10}R^{11}$ or N-bonded heterocyclyl.

15. A cyclohexenonequinolinoyl compound of the formula I as claimed in claim 13, where $R^5$ is halogen, $OR^7$, $NR^{10}R^{11}$ or N-bonded heterocyclyl.

16. A cyclohexenonequinolinoyl compound of the formula I as claimed in claim 13, where $R^7$ is $C_1$–$C_6$-alkyl, $C_1$–$C_{20}$-alkylcarbonyl, $C_1$–$C_6$-alkoxycarbonyl, ($C_1$–$C_{20}$-alkylthio)carbonyl, N,N-di-($C_1$–$C_6$-alkyl)aminocarbonyl, phenyl, phenylcarbonyl or phenoxy-$C_1$–$C_6$-alkylcarbonyl, it being possible for the phenyl radical of the three last-mentioned substituents to be partially or fully halogenated and/or to carry one to three of the following radicals:

nitro, cyano, $C_1$–$C_4$-alkyl, $C_1$–$C_4$-haloalkyl, $C_1$–$C_4$-alkoxy or $C_1$–$C_4$-haloalkoxy;

$R^{10}$ is $C_1$–$C_6$-alkyl or $C_1$–$C_6$-alkoxy;

$R^{11}$ is $C_1$–$C_6$-alkyl.

17. A process for preparing compounds of the formula I as claimed in claim 13 where $R^5$=halogen, which comprises reacting a cyclohexanedione derivative of the formula III,

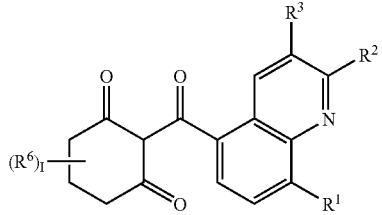
III where the variables $R^1$ to $R^3$ and I are each as defined in claim 13, with a halogenating agent.

18. A process for preparing compounds of the formula I as claimed in claim 13 where $R^5$=$OR^7$, $OSO_2R^8$, $OPR^8R^9$, $OPOR_8R^9$ or $OPSR^8R^9$, which comprises reacting a cyclohexanedione derivative of the formula III,

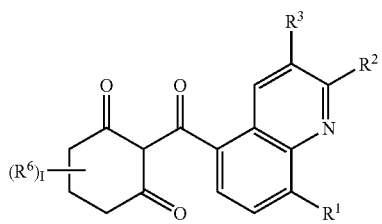
III where the variables $R^1$ to $R^3$, and I are each as defined in claim 13, with a compound of the formula IVα, IVβ, IVγ, IVδ or IVε,

| $L^1$—$R^7$ | (IVα) |
| $L^1$—$SO_2R^8$ | (IVβ) |
| $L^1$—$PR^8R^9$ | (IVγ) |
| $L^1$—$POR^8R^9$ | (IVγ) |
| $L^1$—$PSR^8R^9$ | (IVε) | where the variables $R^7$ to $R^9$ are each as defined in claim 13 and $L^1$ is a nucleophilically replaceable leaving group.

19. A process for preparing compounds of the formula I as claimed in claim 13 where $R^5$=$OR^7$, $SR^7$, $POR^8R^9$, $NR^{10}R^{11}$, $ONR^{11}R^{12}$, or N-linked heterocyclyl, which comprises reacting a compound of the formula I α(≡I where $R^5$=halogen, $OSO_2R^8$),

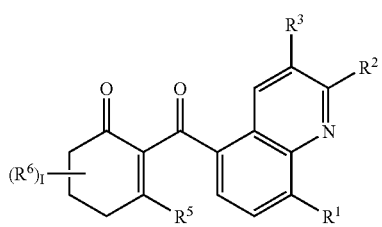
and/or

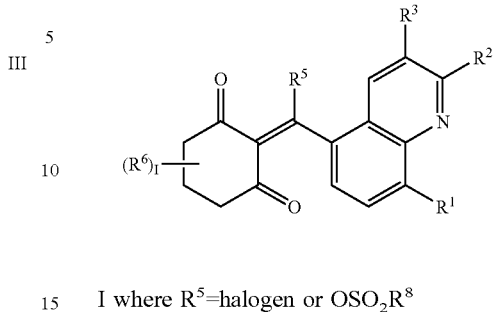

I where $R^5$=halogen or $OSO_2R^8$ where the variables $R^1$ to $R^3$, and I are each as defined in claim 13, with a compound of the formula Vα, Vβ, Vγ, Vγ, Vδ, Vε, Vη,

| $HOR^7$ | (Vα) |
| $HSR^7$ | (Vβ) |
| $HPOR^8R^9$ | (Vγ) |
| $HNR^{10}R^{11}$ | (Vδ) |
| $HONR^{11}R^{12}$ | (Vε) |

H(N-linked heterocyclyl) Vη where the variables $R^7$ to $R^{12}$ are each as defined in claim 13, if appropriate in the presence of a base.

20. A process for preparing compounds of the formula I as claimed in claim 13 where $R^5$=$SOR^8$, $SO_2R^8$, which comprises reacting a compound of the formula Iβ (≡I where $R^5$=$SR^8$),

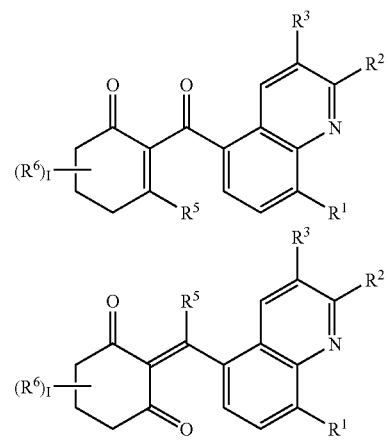
and/or

I where $R^5$=$SR^6$ where the variables $R^1$ to $R^5$, $R^7$, $R^8$ and I are each as defined in claim 13, with an oxidizing agent.

21. A composition, comprising a herbicidally effective amount of at least one cyclohexenonequinolinoyl compound of the formula I or an agriculturally useful salt of formula I as claimed in claim 13 and conventional crop protection formulation auxiliaries.

22. A process for preparing a composition as claimed in claim 21, which comprises mixing a herbicidally effective amount of at least one cyclohexenonequinolinoyl derivative of the formula I or an agriculturally useful salt of formula I and conventional crop protection formulation auxiliaries.

23. A method for controlling undesirable vegetation, which comprises allowing a herbicidally effective amount of at least one cyclohexenonequinolinoyl compound of the formula I or an agriculturally useful salt of formula I as claimed in claim 13 to act on plants, their habitat and/or on seeds.

* * * * *

UNITED STATES PATENT AND TRADEMARK OFFICE
CERTIFICATE OF CORRECTION

PATENT NO. : 7,030,063 B1 Page 1 of 1
APPLICATION NO. : 09/763704
DATED : April 18, 2006
INVENTOR(S) : Witschel et al.

It is certified that error appears in the above-identified patent and that said Letters Patent is hereby corrected as shown below:

In Claim 1, col. 63, indicated line 38:
the wording "$C_3$-$C_1$-alkenyl" should read --$C_3$-$C_6$-alkenyl--

In Claim 8, col. 66, indicated line 60:
the wording "$R^1$ to $R^3$, $R^5$ and l" should read --$R^1$ to $R^3$, $R^6$ and l--

In Claim 8, col. 66, indicated line 62:
the wording "$V\Theta$," should be deleted In Claim 13, col. 69, indicated lines 28 and 29:
the expression "N-($C_3$-$C_8$-alkenyl)-N-$C_1$-$C_6$-alkyl)aminocarbonyl"
should read --N-($C_3$-$C_6$-alkenyl)-N-$C_1$-$C_6$-alkyl)aminocarbonyl--

Signed and Sealed this

Second Day of October, 2007

JON W. DUDAS
*Director of the United States Patent and Trademark Office*